United States Patent
Johnson, Jr. et al.

(10) Patent No.: US 6,632,825 B2
(45) Date of Patent: Oct. 14, 2003

(54) ANTIPICORNAVIRAL COMPOUNDS AND COMPOSITIONS, THEIR PHARMACEUTICAL USES, AND MATERIALS FOR THEIR SYNTHESIS

(75) Inventors: Theodore O. Johnson, Jr., San Diego, CA (US); Shao Song Chu, Encinitas, CA (US); Brian Walter Eastman, San Diego, CA (US); Ye Hua, La Jolla, CA (US); Hiep The Luu, San Diego, CA (US); Siegfried Heinz Reich, Solana Beach, CA (US); Donald James Skalitzky, San Diego, CA (US); Yi Yang, San Diego, CA (US); Thomas F. Hendrickson, Encinitas, CA (US); Fora P. Chan, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 19 days.

(21) Appl. No.: 09/882,345

(22) Filed: Jun. 13, 2001

(65) Prior Publication Data

US 2002/0061916 A1 May 23, 2002

Related U.S. Application Data

(60) Provisional application No. 60/211,424, filed on Jun. 14, 2000.

(51) Int. Cl.$^7$ .................. A61K 31/44; A61P 43/00; C07D 241/36

(52) U.S. Cl. .............. 514/306; 514/343; 514/367; 514/387; 514/414; 514/422; 546/278.4; 546/138; 548/162; 548/306.1; 548/525; 548/535; 548/492

(58) Field of Search ................ 546/278.4, 138; 548/492, 306.1, 162, 525, 535; 514/343, 306, 414, 387, 367, 422

(56) References Cited

U.S. PATENT DOCUMENTS

| | | | |
|---|---|---|---|
| 5,374,623 A | 12/1994 | Zimmerman et al. | 514/17 |
| 5,498,616 A | 3/1996 | Mallamo et al. | 514/300 |
| 5,856,530 A | 1/1999 | Webber | 549/478 |
| 5,962,487 A | 10/1999 | Webber et al. | 514/378 |
| 6,020,371 A | 2/2000 | Dragovich et al. | 514/514 |
| 6,331,554 B1 | 12/2001 | Dragovich et al. | 514/357 |

FOREIGN PATENT DOCUMENTS

| | | |
|---|---|---|
| EP | 0 201844 | 11/1986 |
| EP | 0 632051 | 6/1994 |
| WO | WO 92/22570 | 12/1992 |
| WO | WO 94/04172 | 3/1994 |
| WO | WO 95/15749 | 6/1995 |
| WO | WO 95/23222 | 8/1995 |
| WO | WO 95/31433 | 11/1995 |
| WO | WO 96/30395 | 10/1996 |
| WO | WO 97/31937 | 9/1997 |
| WO | WO 97/43305 | 11/1997 |
| WO | WO 97/49668 | 12/1997 |
| WO | WO 98/43950 | 10/1998 |
| WO | WO 99/31122 | 6/1999 |
| WO | WO 99/57135 | 11/1999 |
| WO | WO 00/78708 | 12/2000 |
| WO | WO 01/10894 | 2/2001 |
| WO | WO 01/14329 | 3/2001 |
| WO | WO 01/14576 | 3/2001 |
| WO | WO 01/40189 | 6/2001 |

OTHER PUBLICATIONS

Van Der Bent, Arie et al., "Synthesis and biological evaluation of lorglumide–like hybrid cholecystokinin—A receptor antagonists", CA 121:34962.

Dragovich et al., "Structure–based Design of Irreversible, Tripeptidyl Human Rhinovirus 3C Protease Inhibitors Containing N–methyl Amino Acids", Bioorg. & Med. Chem. Let. (1999), vol. 9, No. 15, pp. 2189–2194.

Liu et al., "Structure–Activity Relationships for Inhibition of Papain by Peptide Michael Acceptors", J. Med. Chem., 35, 1067–1075 (1992).

Dragovich, et al., "Structure–Based Design, Synthesis, and Biological Evaluation of Irreversible Human Rhinovirus 3C Protease Inhibitors. 3. Structure–Activity Studies of Ketomethylene–Containing Peptidomimetics", J. Med. Chem. (1999) vol. 42, No. 7, pp. 1203–1212.

Dragovich, et al., "Structure–Based Design, Synthesis, and Biological Evaluation of Irreversible Human Rhinovirus 3C Protease Inhibitors. 3. Structure–Activity Studies of Ketomethylene–Containing Peptidomimetics", J. Med. Chem. (1999) vol. 42, No. 7, pp. 1213–1224.

Dragovich, et al., "Solid–phase Synthesis of Irreversible Human Rhinovirus 3C Protease Inhibitors. Part 1: Optimization of Tripeptides Incorporating N–terminal Amides", Bioorg. & Med. Chem. (1999)(7), pp. 589–598.

(List continued on next page.)

Primary Examiner—Joseph K. McKane
Assistant Examiner—Andrea D. Small
(74) Attorney, Agent, or Firm—Karl Neidert; Bryan C. Zielinski; Peter Richardson

(57) ABSTRACT

Compounds of the formula:

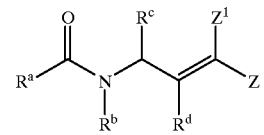

where the formula variables are as defined in the disclosure, advantageously inhibit or block the biological activity of the picornaviral 3C protease. These compounds, as well as pharmaceutical compositions containing these compounds, are useful for treating patients or hosts infected with one or more picornaviruses, such as RVP. Intermediates and synthetic methods for preparing such compounds are also described.

11 Claims, No Drawings

OTHER PUBLICATIONS

Bowden et al., "Organophosphorus Chemistry. Part XIV. Reaction of Phosphorodiamidous Chlorides with Sulphonamides: a New Route to Diazadiphosphetidines", *J. Chem. Soc.* Perkin Transactions I Organic and Bio–organic Chemistry (1973) 516–520.

Dragovich, et al., "Structure–Based Design, Synthesis, and Biological Evaluation of Irreversible Human Rhinovirus 3C Protease Inhibitors. 1. Michael Acceptor Structure–Activity Studies", *J. Med. Chem.* (1998) vol. 41, No. 15, pp. 2806–2818.

Hartke, et al., "α,β–ungesattigte Thion– und Dithioester durch Kondensationsreaktionen", *Leibigs, Ann. Chem.* (1989), pp. 321–330.

Herold et al., "*A Versatile and Stereocontrolled Synthesis of Hydroxyethylene Dipeptide Isosteres*", J. Org. Chem. (1989) vol. 54, No. 5, pp. 1178–1185.

Hanzlik et al., "*Structure–Activity Relationships for Inhibition of Papain by Peptide Michael Acceptors*", J. Med. Chem. (1992) vol. 35, No. 6, pp. 1067–1075.

DeJohn, et al., "Functionalization of Substituted 2(1H)– and 4(1H)–Pyridones, III. The Preparation of Substituted 6–Vinyl–1,2–dihydro–2–oxo– and 1,4–Dihydro–4–oxo–3–pyridinecarboxylic Acids through the Chemistry of Pyridone Dianions", *J. Heterocyclic Chem.* (1983) vol. 20, No. 5, pp. 1295–1302.

Fasseur et al., "Studies on Pyrrolidones, Synthesis and N–Alkylation of β–Enaminoesters Derived from Pyroglutamic Acid", *J. Heterocyclic Chem.* (1992) vol. 29, No. 5, pp. 1285–1291.

Straub, et al., "Synthesis of the Angiotensin Converting enzyme Inhibitor (–)–A58365A via an Isomunchnone cycloaddition Reaction", *Org. Lett.* (1999) vol. 1, No. 1, pp. 83–85.

Fang et al., "Total Synthesis of the Angiotensin–Converting Enzyme Inhibitor A58365A: On the Use of Pyroglutamate as a Chiral Educt", *Tetrahedron Lett.* (1989) vol. 30, No. 28, pp. 3621–3624.

Crossley et al., "Convenient Route to γ–nitro–α–amino acids: conjugate addition of nitroalkanes to dehydroalanine derivatives", *J. Chem. Soc. Perkin Trans. I* (1998) No. 6, pp. 1113–1121.

Bellus, "Incorporation of Sulfur Dioxide into the Products of Reaction of Shiff Bases with Halo– or Alkylthio–ketones in Liquid $SO_2$", *Helvetica Chimica Acta* (1975) vol. 58, No. 271, pp. 2509–2511.

Kong et al., "*Synthesis and Evaluation of Peptidyl Michael Acceptors That Inactivate Human Rhinovirus 3C Protease and Inhibit Virus Replication*", J. Med. Chem. (1998) vol. 41, No. 14, pp. 2579–2587.

Webber et al., "*Tripeptide Aldehyde Inhibitors of Human Rhinovirus 3C Protease: Design, Synthesis, Biological Evaluation, and Cocrystal Structure Solution of P1 Glutamine Isosteric Replacements*", J. Med. Chem. (1998) vol. 41, No. 15, pp. 2786–2805.

Luly et al., "*A Synthesis of Protected Aminoalkyl Epoxides from α–Amino Acids*", J. Org. Chem. (1987) vol. 52, No. 8, pp. 1487–1492.

Ikuta et al., "Synthesis and Anti–inflamatory Activities of 3–(3,5–Di–text–butyl–4–hydroxybenzylidene) pyrolidin–2–ones", J. Med. Chem. (1987), vol. 30, pp. 1995–1998.

Hartke, "A Simple Route to 2–Alkenethiole O–Esters and 2–Alkenedithioic Esters" [Thiono– and Dithioesters, 37], *Synthesis* (1985) pp. 960–961.

Baldwin,, "Diarylmethylene–Tetracyanoethylene Cycloadditions", *J. Org.Chem.* (1971) vol. 36, No. 10, pp. 1441–1443.

Weislow, et al., "New Soluble–Formazan Assay for HIV–1 Cytopathic Effects: Application to High–Flux Screening of Synthetic and Natural Products for AIDS–Antiviral Activity", *J. Natl. Cancer* (1989) vol. 81, No. 8, pp. 577–586.

Diana et al., "Picornavirus Inhibitors: Trifluoromethyl Substitutions Provides a Global Protective Effect against Hepatic Metabolism", *J. Med. Chem.* (1995), vol. 38, pp. 1355–1371.

Palmer et al., "Vinyl Sulfones as Mechanism—Based Cysteine Protease Inhibitors", J. Med. Chem. (1995), vol. 38, pp. 3193–3196.

Dragovich, et al., "*Structure–Based Design, Synthesis, and Biological Evaluation of Irreversible Human Rhinovirus 3C Protease Inhibitors. 2. Peptide Structure–Activity Studies*", Med Chem. (1998) vol. 41, No. 15, pp. 2819–2834.

Bradbury et al., "*An Efficient Synthesis of the γ–Lactone Corresponding to a Hydroxylethylene Dipeptide Isostere Using Stereoselective Bromolactonisation of a Chiral Acyloxazolidinone*", Tetrahedron Letters (1989) vol. 30, No. 29, pp. 3845–3848.

Chida et al., "*Total Synthesis and Absolute Configuration of Bengamide A*", J. Chem. Soc., Chem. Commun. (1992) pp. 1064–1066.

Dondoni et al., "*Thiazole–Based Stereoselective Routes to Leucine and Phenylalanine Hydroxyethylene Dipeptide Isostere Inhibitors of Renin and HIV–1 Aspartic Protease*", J. Org. Chem. (1995) vol. 60, No. 24, pp. 7927–7933.

Birch, et al., "*Purification of Recombinant Human Rhinovirus 14 3C Protease Expressed in Escherichia coli*," Protein Expr. Pur. (1995) vol. 6(5) 609–618.

McWilliams et al., "*Tandem Asymmetric Transformations: An Asymmetric 1,2–Migration from a Higher Order Zincate Coupled with a Stereoselective Homoaldol Reaction*", J. Am. Chem. Soc. (1996) vol. 118, No. 47, pp. 11970–11971.

Kruse, et al., "*New Methods for the Synthesis of 2–ArylPyrroles*", Heterocycles (1987) vol. 26, No. 12, pp. 3141–3151.

Bailey, et al., "*Ethyl Pyrrole–2–Carboxylate*", Org. Synth. (1971) vol. 51, 100–102.

Gonzalez–Muniz et al., "*Synthesis of 2–Substituted 8–Amino–3–oxoindolizoline–2–carboxylic Acid Derivatives as Peptide Conformation Mimetics*". Tetrahedron (1992) vol. 48, No. 24, pp. 5191–5198.

Garcia–Lopez, et al., "*A Simple and Versatile Route to Ketomethylene Dipeptide Analogs*", Tetrahedron (1988) vol. 29, No. 13, pp. 1577–1580.

Garcia–Lopez, et al., "*Synthesis of Ketomethylene Dipeptides Containing Basic Amino Acid Analogues at C–Terminus*", Tetrahedron (1988), vol. 44, No. 16, 5131–5138.

Charlton, et al., "*Asymmetric synthesis of lignans using oxazolidinones as chiral auxiliaries*", NRC–CNRC Canadian Journal of Chemistry (1997), vol. 75, No. 8, pp. 1076–1083.

Silverstein, et al., "*2–Pyrrolealdehyde*", Org. Synth. (1963) Coll. vol. IV, 831–833.

Hoffman, R.V., Tao, J. "*A Simple, Stereoselective Synthesis of Ketomethylene Dipeptide Isosteres*", Tetrahedron (1997) vol. 53, No. 21, pp. 7119–7126.

Sunberg, et al., "3–(3–Pyrrolyl) thiopyrrolidones as Precursors of Benzo [1,2–b:4,3–b']dipyrroles. Synthesis of Structures Related to the Phosphodiesterase Inhibitors PDE–I and PDE–II", J. Org. Chem. (1985) vol. 50, No. 4, pp. 425–432.

Kaldor et al., "Glutamine–Derived Aldehydes for the Inhibition of Human Rhinovirus 3C Protease", Bioorganic & Medicinal Chemistry Letters, vol. 5, No. 17 (1995) pp. 2021–2026.

Murray et al., "The enantiospecific synthesis of novel lysine analogues incorporating a pyrrolidine containing side chain", Tetrahedron Letters, vol. 39 (1998) pp. 6721–6724.

Webber et al., "Design, Synthesis, and Evaluation of Nonpeptidic Inhibitors of Human Rhinovirus 3C Protease", J. Med. Chem. (1996) vol. 39, No. 26, pp. 5072–5082.

Jones et al., "A Short Stereocontrolled Synthesis of Hydroxyethylene Dipeptide Isosteres", J. Org. Chem. (1993) vol. 58, No. 8, pp. 2286–2290.

Pegorier et al., "A General Stereocontrolled Synthesis of Hydroxyethylene Dipeptide Isosteres", Tetrahedron Letters (1995) vol. 36, No. 16, pp. 2753–2756.

Wuts et al., "Synthesis of the Hydroxyethylene Isostere of Leu–Val", J. Org. Chem. (1992) vol. 57, No. 25, pp. 6696–6700.

Hanzlik et al., "Vinylogous Amino Acid Esters: A New Class of Inactivators for Thiol Proteases", J. Med. Chem. (1984), vol. 27, No. 6, pp. 711–712.

Wipf et al., "$S_N2'$—Reactions of Pepticle Aziridenes. A Cuprate– Based Approach to (E)–Alkene Isosters", J. Org. Chem. 1994, vol. 59, No. 17, pp. 4875–4886.

Ming Tao et al., "Inhibition of CalPain by Peptidyl Heterocycles", Bio–org. & Med. Chem. Lett. 1996, vol. 6, No. 24, pp. 3009–3012.

Moss et al., "Peptidomimetic Inhibitors of Herpes Simplex Virus Ribonucleotide Reductase with Improved Vivo Anti-Viral Activity", J. Med. Chem. 1996, vol. 39, No. 21, pp. 4173–4180.

Venkatraman et al., "Synthesis of Potential Inhibitors for Human Rhinovirus 3C Protease", The Second Winter Conference on Medicinal and Bioorganic Chemistry, Steamboat Springs, CO, Jan . 26–31, 1997.

Jackson et al., Preparation of Enantiomerically Pure Protected 4–Oxo–α–amino Acids and 3–Arly–α–amino Acids from Serine, J. Org. Chem. (1992), vol. 57, No. 12 pp. 3397–3404.

ANTIPICORNAVIRAL COMPOUNDS AND COMPOSITIONS, THEIR PHARMACEUTICAL USES, AND MATERIALS FOR THEIR SYNTHESIS

This application claims benefit of U.S. Provisional Patent Application No. 60/211,424, filed Jun. 14, 2000.

BACKGROUND OF THE INVENTION

1. Field of the Invention

The invention relates to compounds that advantageously inhibit the enzymatic activity of picornaviral 3C proteases, especially rhinovirus 3C proteases (RVPs), and that retard viral growth in cell culture. The invention also relates to the use of such compounds in pharmaceutical compositions and therapeutic treatments for rhinoviral infections. The invention further relates to processes for synthesizing such compounds and intermediate compounds useful in such syntheses.

2. Related Background Art

The picornaviruses are a family of tiny non-enveloped positive-stranded RNA-containing viruses that infect humans and other animals. These viruses include the human rhinoviruses, human polioviruses, human coxsackieviruses, human echoviruses, human and bovine enteroviruses, encephalomyocarditis viruses, meningitis virus, foot and mouth viruses, hepatitis A virus, and others. The human rhinoviruses are a major cause of the common cold. To date, there are no effective therapies that cure the common cold, only treatments that relieve the symptoms.

Picornaviral infections may be treated by inhibiting the proteolytic 3C enzymes. These enzymes are required for the natural maturation of the picornaviruses. They are responsible for the autocatalytic cleavage of the genomic, large polyprotein into the essential viral proteins. Members of the 3C protease family are cysteine proteases, where the sulfhydryl group most often cleaves the glutamine-glycine amide bond. Inhibition of 3C proteases is believed to block proteolytic cleavage of the polyprotein, which in turn can retard the maturation and replication of the viruses by interfering with viral particle production. Therefore, inhibiting the processing of this cysteine protease with selective molecules that are specifically recognized should represent an important and useful approach to treat and cure viral infections of this nature and, in particular, the common cold.

Some inhibitors of the enzymatic activity of picornaviral 3C proteases (i.e., antipicornaviral compounds) have been recently discovered. See, for example: U.S. Pat. Nos. 5,856,530; 5,962,487; U.S. patent application Ser. No. 08/991,282, filed Dec. 16, 1997, by Dragovich et al.; and U.S. patent application Ser. No. 09/301,977, filed Apr. 29, 1999, by Dragovich et al. See also: Dragovich et al., "Structure-Based Design, Synthesis, and Biological Evaluation of Irreversible Human Rhinovirus 3C Protease Inhibitors . . . ," *J. Med. Chem.* (1999), Vol. 42, No. 7, 1203–1212, 1213–1224; and Dragovich et al., "Solid-phase Synthesis of Irreversible Human Rhinovirus 3C Protease Inhibitors . . . ," *Bioorg. & Med. Chem.* (1999), Vol. 7, 589–598. There is still a desire, however, to discover compounds that are especially potent antipicornaviral agents.

SUMMARY OF THE INVENTION

The present invention relates to compounds of the general formula I:

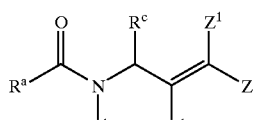

wherein:

$R^a$ may be selected from an aryl, heteroaryl, alkyl, alkenyl, amino, cycloalkyl or heterocycloalkyl group, provided that $R^a$ is not pyrrolidinyl, where the aryl, heteroaryl, alkyl, alkenyl, amino, cycloalkyl or heterocycloalkyl group is unsubstituted or substituted with one or more suitable substituents;

$R^c$ is a substituent having the formula:

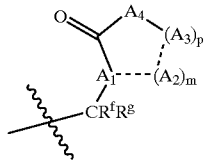

wherein:

$R^f$ and $R^g$ are each independently H or lower alkyl;

m is 0 or 1;

p is an integer of from 0 to 5;

$A_1$ is CH or N;

when p is 1, 2, 3, 4, or 5, $A_2$ is $C(R^h)(R^i)$, $N(R^j)$, S, S(O), $S(O)_2$, or O, and when p is 0, $A_2$ is $C(R^h)(R^i)(R^j)$, $N(R^i)(R^j)$, $S(R^i)$, $S(O)(R^i)$, $S(O)_2(R^i)$, or $O(R^i)$, where each $R^h$, $R^i$ and $R^j$ is independently H or a lower alkyl group;

each $A_3$ present is independently $C(R^h)(R^i)$, $N(R^j)$, S, S(O), $S(O)_2$, or O; where each $R^h$, $R^i$ and $R^j$ is independently H or lower alkyl;

when p is 1, 2, 3, 4, or 5, $A_4$ is $N(R^k)$, $C(R^h)(R^i)$, or O; and when p is 0 (i.e., $A_3$ is not present), $A_4$ is $N(R^k)(R^l)$, $C(R^h)(R^i)(R^j)$, and $O(R^i)$, where each $R^h$, $R^i$ and $R^j$ is independently H or lower alkyl, each $R^k$ is H, alkyl, aryl, or acyl, and each $R^l$ is H, alkyl, or aryl;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present (i.e., m=1) and a hydrogen atom when $A_2$ is absent (i.e., m=0);

$R^d$ is H, halogen, hydroxyl or an alkyl, alkoxy or alkylthio group, where the alkyl, alkoxy or alkylthio group is unsubstituted or substituted with one or more suitable substituents;

$R^b$ is H or an alkyl group, unsubstituted or substituted with one or more suitable substituents;

Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)$R^n$ —CO$_2R^n$—CN, —C(O)NR"$R^o$, —C(O)NR"O$R^o$, —C(S)$R^n$, —C(S)O$R^n$—C(S)NR"$R^o$, —C(=NR")$R^o$, —C(=NR")O$R^o$, —NO$_2$, —SO$R^o$, —SO$_2R^n$, —SO$_2$NR"$R^o$, —SO$_2$(NR")(O$R^o$), —SONR", —SO$_3R^n$, —PO(O$R^n$)$_2$, —PO(O$R^n$)(O$R^o$), —PO(NR"$R^o$)(O$R^p$), —PO(NR"$R^o$)(NR$^pR^q$), —C(O)NR"NR$^oR^p$, —C(S)NR"NR$^oR^p$, where $R^n$, $R^o$, $R^p$ and $R^q$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the $R^n$, $R^o$, $R^p$ and $R^q$, taken together with the atoms to which they are bonded, form a heterocycloalkyl group, which may be optionally substituted, or Z and $R^d$, together with the atoms to which they are bonded, form a cycloalkyl or heterocycloalkyl group, where Z and $R^d$ are as defined above except for moieties that cannot form the cycloalkyl or heterocycloalkyl group, or Z and $Z^1$, together with the atoms to which they are bonded, form a cycloalkyl or heterocycloalkyl group, where Z and $Z^1$ are as defined above (except for moieties that cannot form the cycloalkyl or heterocycloalkyl group); and In another embodiment of the compounds of the above Formula I, $A_1$ is CH or N; $A_2$ is $C(R^h)(R^i)$, $N(R^j)$, S, S(O), $S(O)_2$, or O; where each $R^h$, $R^i$ and $R^j$ is independently H or lower alkyl; each $A_3$ present is independently $C(R^h)$ $(R^i)$, $N(R^j)$, S, S(O), $S(O)_2$, or O; where each $R^h$, $R^i$ and $R^j$ is independently H or lower alkyl; when p is 1, 2, 3, 4, or 5, $A_4$ is $N(R^k)$, $C(R^h)(R^i)$, or O; and when p is 0 (i.e., $A_3$ is not present), $A_4$ is $N(R^k)(R^l)$, $C(R^h)(R^i)(R^j)$, and $O(R^l)$, where each $R^h$, $R^i$ and $R^j$ is independently H or lower alkyl, each $R^k$ is H, alkyl, aryl, or acyl, and each $R^l$ is H, alkyl, or aryl; provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present (i.e., m=1) and a hydrogen atom when $A_2$ is absent (i.e., m=0); and Z and $Z^1$ are each independently H, F, a unsubstituted or substituted alkyl group, cycloalkyl group, heterocycloalkyl group, aryl group or heteroaryl group, —C(O)$R^n$, —$CO_2R^n$, —CN, —C(O)$NR^nR^o$, —C(O)$NR^nOR^o$, —C(S)$R^n$, —C(S)$NR^nR^o$, —$NO_2$, —$SOR^o$, —$SO_2R^n$, —$SO_2NR^nR^o$, —$SO_2(NR^n)(OR^o)$, —$SONR^n$, —$SO_3R^n$, —$PO(OR^n)_2$, —$PO(OR^n)(OR^o)$, —PO$(NR^nR^o)(OR^p)$, —$PO(NR^nR^o)(NR^pR^q)$, —C(O)$NR^nNR^oR^p$, —C(S)$NR^nNR^oR^p$, where each $R^n$, $R^o$, $R^p$ and $R^q$ are independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the $R^n$, $R^o$, $R^p$ and $R^q$, taken together with the atoms to which they are bonded, form a heterocycloalkyl group, which may be optionally substituted, form a heterocycloalkyl group, provided that Z and $Z^1$ are not both H; or Z and $R^d$, together with the atoms to which they are bonded, form a cycloalkyl or heterocycloalkyl group, where Z and $R^d$ are as defined above except for moieties that cannot form the cycloalkyl or heterocycloalkyl group; or Z and $Z^1$, together with the atoms to which they are bonded, form a cycloalkyl or heterocycloalkyl group, where Z and $Z^1$ are as defined above except for moieties that cannot form the cycloalkyl or heterocycloalkyl group.

One embodiment of this invention relates to compounds useful for inhibiting the activity of picornaviral 3C proteases having the following general formula:

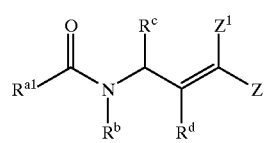

II wherein $R^{a1}$ is a cycloalkyl, heterocycloalkyl, aryl or heteroaryl group, provided that $R^{a1}$ is not a substituted pyrrolidinyl, where the cycloalkyl, heterocycloalkyl, aryl or heteroaryl group is unsubstituted or substituted with one or more suitable substituents; and $R^b$, $R^c$, $R^d$, Z and $Z^1$ are as defined above.

Another embodiment of this invention relates to compounds useful for inhibiting the activity of picornaviral 3C proteases having the following general formula:

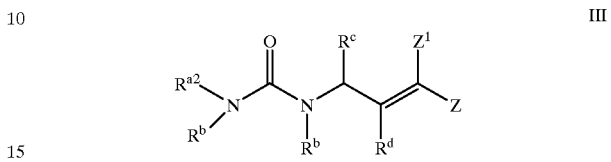

III wherein $R^{a2}$ is an alkyl, aryl or heteroaryl group, where the alkyl, aryl or heteroaryl group is unsubstituted or substituted with one or more suitable substituents; and $R^b$, $R^c$, $R^d$, Z and $Z^1$ are as defined above.

This invention also relates to compounds useful for inhibiting the activity of picornaviral 3C proteases having the following general formula:

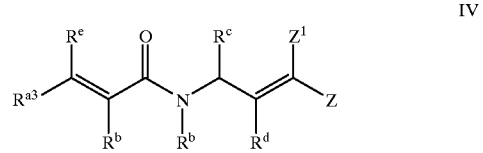

IV wherein $R^{a3}$ is an aryl, heterocycloalkyl, heteroaryl or arylaminocarbonyl group, where the aryl, heterocycloalkyl, heteroaryl or arylaminocarbonyl group is unsubstituted or substituted with one or more suitable substituents;

$R^e$ is H, halogen, hydroxyl, or an alkyl, alkoxy or alkylthio group, where the alkyl, alkoxy or alkylthio group is unsubstituted or substituted with one or more suitable substituents; and $R^b$, $R^c$, $R^d$, Z and $Z^1$ are as defined above.

This invention relates to compounds useful for inhibiting the activity of picornaviral 3C proteases having the general formula:

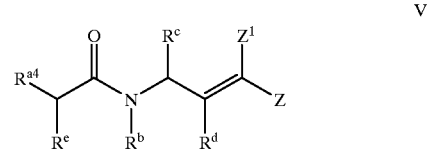

V wherein $R^{a4}$ is an aryloxy, heteroaryloxy, alkyloxy, cycloalkyloxy, heterocycloalkyloxy, aryl, cycloalkyl, or heteroaryl group, where the aryloxy, heteroaryloxy, alkyloxy, cycloalkyloxy, heterocycloalkyloxy, aryl, cycloalkyl, or heteroaryl group is unsubstituted or substituted with one or more suitable substituents; and $R^b$, $R^c$, $R^d$, $R^e$, Z and $Z^1$ are as defined above.

In addition to compounds of the Formulae I–V, antipicornaviral agents of the invention include prodrugs, pharmaceutically active metabolites, and pharmaceutically acceptable salts and solvates of such compounds.

DETAILED DESCRIPTION OF THE INVENTION

In accordance with a convention used in the art,

is used in structural formulas herein to depict the bond that is the point of attachment of the substituent to the backbone structure. Where chiral carbons are included in chemical structures, unless a particular orientation is depicted, both stereoisomeric forms are intended to be encompassed.

As used herein, the term "alkyl" represents a straight- or branched-chain saturated or unsaturated hydrocarbon, containing 1 to 10 carbon atoms, that may be unsubstituted or substituted by one or more of the substituents described below. Exemplary alkyl substituents include, but are not limited to, methyl (Me), ethyl (Et), propyl, isopropyl, butyl, isobutyl, t-butyl, ethenyl, propenyl, butenyl, pentenyl, ethynyl, butynyl, propynyl, pentynyl, hexynyl and the like. The term "lower alkyl" refers to an alkyl group containing from 1 to 4 carbon atoms.

"Cycloalkyl" represents a group comprising a non-aromatic monocyclic, bicyclic, or tricyclic hydrocarbon containing from 3 to 14 carbon atoms that may be unsubstituted or substituted by one or more of the substituents described below and may be saturated or partially unsaturated, mono- or poly-carbocyclic ring, preferably having 5–14 ring carbon atoms. Exemplary cycloalkyls include monocyclic rings having from 3–7, preferably 3–6, carbon atoms, such as cyclopropyl, cyclobutyl, cyclopentyl, cyclohexyl, cycloheptyl and the like, that may be fully saturated or partially unsaturated. Illustrative examples of cycloalkyl groups include the following:

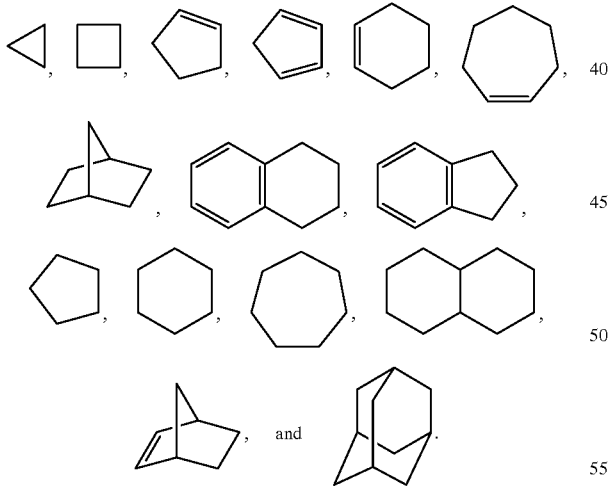

"Heterocycloalkyl" represents a group comprising a non-aromatic, monovalent monocyclic, bicyclic, or tricyclic radical, which may be unsubstituted or substituted by one or more of the substituents described below and may be saturated or partially unsaturated, containing 3 to 18 ring atoms and which includes 1 to 5 hetero atoms selected from nitrogen, oxygen and sulfur, and to which may be fused one or more cycloalkyl groups, aryl groups, or heteroaryl groups. Illustrative examples of heterocycloalkyl groups include, but are not limited to, azetidinyl, pyrrolidyl, piperidyl, piperazinyl, morpholinyl, chromenyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like. Illustrative examples of heterocycloalkyl groups include the following moieties:

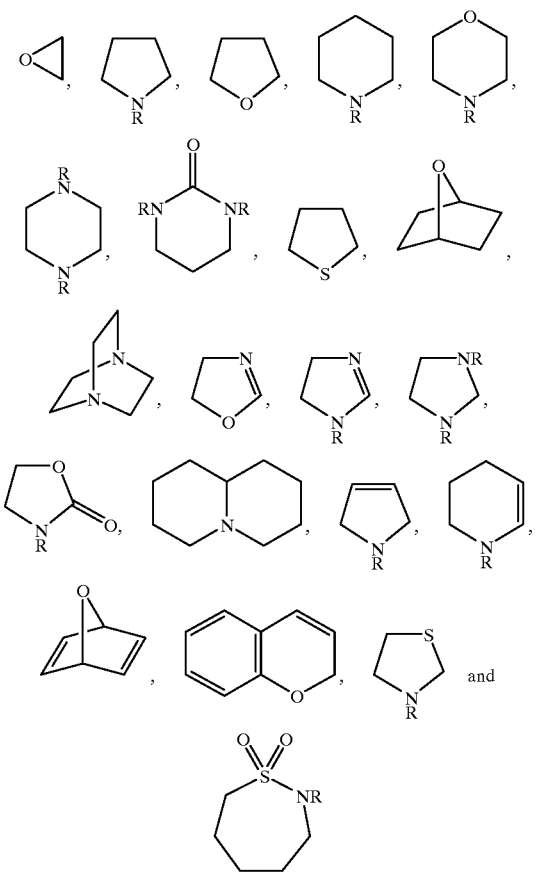

wherein R is alkyl, aryl, cycloalkyl, heterocycloalkyl, hydroxyl or represents a formula of a compound of this invention.

"Aryl" represents a group comprising an aromatic, monovalent monocyclic, bicyclic, or tricyclic radical containing from 6 to 18 carbon ring atoms, which may be unsubstituted or substituted by one or more of the substituents described below. Illustrative examples of aryl groups include the following moieties:

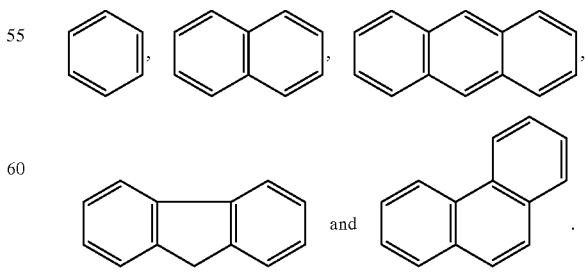

"Heteroaryl" represents a group comprising an aromatic monovalent monocyclic, bicyclic, or tricyclic radical, containing 5 to 18 ring atoms, including 1 to 5 heteroatoms selected from nitrogen, oxygen and sulfur, which may be unsubstituted or substituted by one or more of the substituents described below. As used herein, the term "heteroaryl" is also intended to encompass the N-oxide derivative (or N-oxide derivatives, if the heteroaryl group contains more than one nitrogen such that more than one N-oxide derivative may be formed) of the nitrogen-containing heteroaryl groups described herein. Illustrative examples of heteroaryl groups include, but are not limited to, thienyl, pyrrolyl, imidazolyl, pyrazolyl, furyl, isothiazolyl, furazanyl, isoxazolyl, thiazolyl, triazolyl, pyridyl, pyrazinyl, pyrimidinyl, pyridazinyl, triazinyl, benzo[b]thienyl, naphtho[2,3-b]thianthrenyl, isobenzofuranyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, benzofuranyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl. Illustrative examples of N-oxide derivatives of heteroaryl groups include, but are not limited to, pyridyl N-oxide, pyrazinyl N-oxide, pyrimidinyl N-oxide, pyridazinyl N-oxide, triazinyl N-oxide, isoquinolyl N-oxide, and quinolyl N-oxide. Further examples of heteroaryl groups include the following moieties:

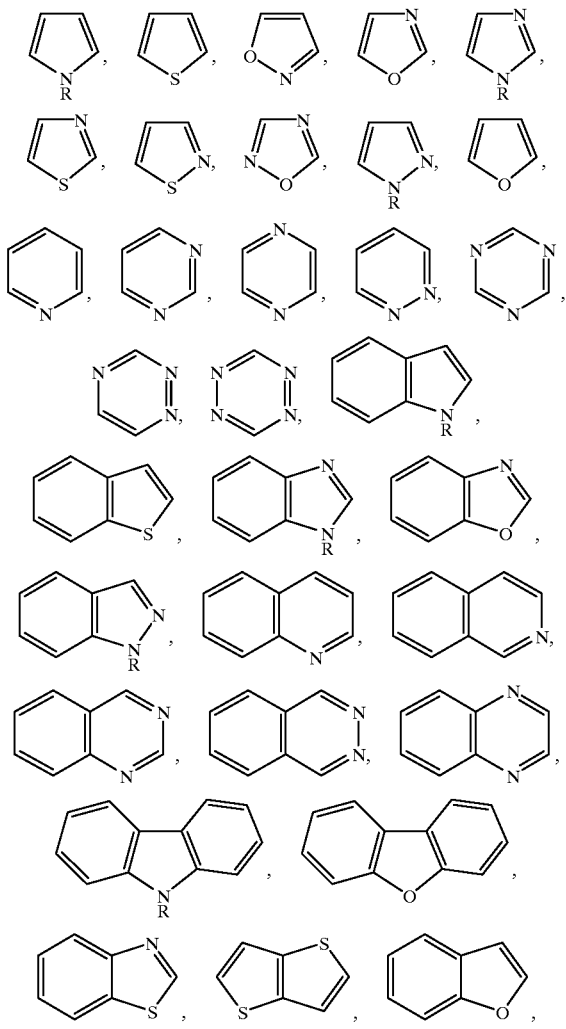

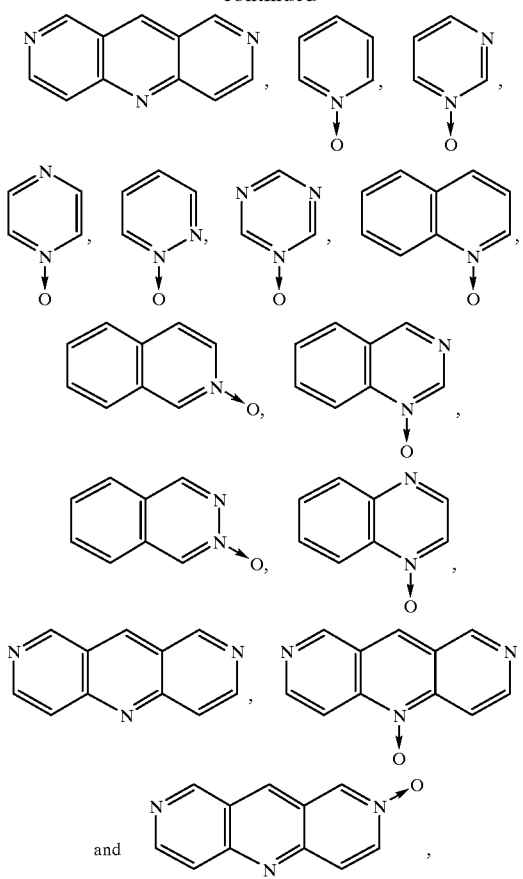

wherein R is alkyl, aryl, cycloalkyl, heterocycloalkyl, hydroxyl or represents a formula of a compound of this invention.

As indicated herein, the alkyl, cycloalkyl, aryl, heterocycloalkyl and heteroaryl groups may be optionally substituted by one or more substituents. The term "optionally substituted" is intended to expressly indicate that the specified group is unsubstituted or substituted by one or more suitable substituents. Various groups may be unsubstituted or substituted (i.e., they are optionally substituted) as indicated. The term "substituent" or "suitable substituent" is intended to mean any suitable substituent that may be recognized or selected, such as through routine testing, by those skilled in the art.

The term "suitable substituent" represents a substituent that is optionally present on any of the above alkyl, aryl, cycloalkyl, heterocycloalkyl or heteroaryl groups, described herein, and is selected from alkyl (except for alkyl) haloalkyl, haloaryl, halocycloalkyl, haloheterocycloalkyl, aryl, cycloalkyl, heterocycloalkyl, heteroaryl, nitro, amino, hydroxamino, cyano, halo, hydroxyl, alkoxy, alkylenedioxy, aryloxy, cycloalkoxy, heterocycloalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, arylthio, and heteroarylthio groups, where any of the alkyl, alkylene, aryl, cycloalkyl, heterocycloalkyl, heteroaryl moieties present in the above substituents may be further substituted with one or more substituents selected from nitro, amino, cyano, halo, haloalkyl, haloaryl, hydroxyl, keto, hydroxamino, alkylamino, dialkylamino, mercapto, and unsubstituted alkyl, aryl, cycloalkyl, heterocycloalkyl, heteroaryl, alkoxy, aryloxy, alkylthio or arylthio groups and where any of the aryl or heteroaryl moieties may be substituted with alkylenedioxy. Preferred "suitable substituents" include halo, nitro, alkyl, cycloalkyl, heterocycloalkyl, aryl, heteroaryl, arylalkyl, heteroarylalkyl, —C(O)R$^r$, —C(O)OR$^r$, —OC(O)R$^r$, —OR$^r$, —SR$^r$, —C(O)NR$^s$R$^t$, and —NR$^s$R$^t$, where each R$^r$, R$^s$, and R$^t$ are independently selected from H, alkyl, cycloalkyl, heterocycloalkyl, aryl, and heteroaryl, and each alkyl, aryl, or heteroaryl substituent may optionally be further substituted with one or two substituents selected from unsubstituted lower alkyl, unsubstituted lower alkoxy, nitro, halo, hydroxy or phenyl, where the phenyl group is unsubstituted or substituted with one or more substituents independently selected from alkyl, haloalkyl, alkylenedioxy, nitro, amino, hydroxamino, alkylamino, dialkylamino, halo, hydroxyl, alkoxy, haloalkoxy, aryloxy, mercapto, alkylthio or arylthio groups.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3$^{rd}$ ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

The terms "halogen" and "halo" represent chloro, fluoro, bromo or iodo substituents. "Heterocycle" is intended to mean a heteroaryl or heterocycloalkyl group. "Acyl" is intended to mean a —C(O)—R radical, where R is an alkyl, cycloalkyl, aryl, heterocycloalkyl or heteroaryl group. "Acyloxy" is intended to mean an —OC(O)—R radical, where R is an alkyl, cycloalkyl, aryl, heterocycloalkyl or heteroaryl group. "Thioacyl" is intended to mean a —C(S)—R radical, where R is an alkyl, cycloalkyl, aryl, heterocycloalkyl or heteroaryl group. "Sulfonyl" is intended to mean an —SO$_2$— biradical. "Sulfenyl" is intended to mean an —SO— biradical. "Sulfo" is intended to mean an —SO$_2$H radical. "Sulfoxide" is intended to mean a —SO$_3$$^-$ radical. "Hydroxy" is intended to mean the radical —OH. "Amine" or "Amino" is intended to mean the radical —NH$_2$. "Alkylamino" is intended to mean the radical —NHR$_a$, where R$_a$ is an alkyl group. "Dialkylamino" is intended to mean the radical —NR$_a$R$_b$, where R$_a$ and R$_b$ are each independently an alkyl group, and is intended to include heterocycloalkyl groups, where R$_a$ and R$_b$, taken together, form a heterocyclic ring that includes the amine nitrogen. "Hydroxamino" is intended to mean the radical —N—OH. "Alkoxy" is intended to mean the radical —OR$_a$, where R$_a$ is an alkyl group. Exemplary alkoxy groups include methoxy, ethoxy, propoxy, and the like. "Lower alkoxy" groups have alkyl moieties having from 1 to 4 carbons. "Alkylenedioxy" is intended to mean the divalent radical —OR$_a$O— which is bonded to adjacent atoms on an aryl or heteroaryl moiety (e.g., adjacent atoms on a phenyl or naphthyl ring), where R$_a$ is a lower alkyl group. "Alkoxycarbonyl" is intended to mean the radical —C(O)OR$_a$, where R$_a$ is an alkyl group. "Alkylsulfonyl" is intended to mean the radical —SO$_2$R$_a$, where R$_a$ is an alkyl group. "Alkylaminocarbonyl" is intended to mean the radical —C(O)NHR$_a$, where R$_a$ is an alkyl group. "Dialkylaminocarbonyl" is intended to mean the radical —C(O)NR$_a$R$_b$, where R$_a$ and R$_b$ are each independently an alkyl group. "Mercapto" is intended to mean the radical —SH. "Alkylthio" is intended to mean the radical —SR$_a$, where R$_a$ is an alkyl group. "Carboxyl" is intended to mean the radical —C(O)OH. "Keto" or "oxo" is intended to mean the radical =O. "Thioketo" is intended to mean the radical =S. "Carbamoyl" is intended to mean the radical —C(O)NH$_2$. "Cycloalkylalkyl" is intended to mean the radical -alkyl-cycloalkyl, where alkyl and cycloalkyl are defined as above, and is exemplified by the bonding arrangement present in the groups —CH$_2$-cyclohexane or —CH$_2$-cyclohexene. "Arylalkyl" is intended to mean the radical -alkylaryl, where alkyl and aryl are defined as above, and is exemplified by the bonding arrangement present in a benzyl group. "Aminocarbonylalkyl" is intended to mean the radical -alkylC(O) NH$_2$ and is exemplified by the bonding arrangement present in the group —CH$_2$CH$_2$C(O)NH$_2$. "Alkylaminocarbonylalkyl" is intended to mean the radical -alkylC(O)NHR$_a$, where R$_a$ is an alkyl group and is exemplified by the bonding arrangement present in the group —CH$_2$CH$_2$C(O)NHCH$_3$. "Alkylcarbonylaminoalkyl" is intended to mean the radical -alkylNHC(O)-alkyl and is exemplified by the bonding arrangement present in the group —CH$_2$NHC(O)CH$_3$. "Dialkylaminocarbonylalkyl" is intended to mean the radical -alkylC(O)NR$_a$R$_b$, where R$_a$ and R$_b$ are each independently an alkyl group. "Aryloxy" is intended to mean the radical —OR$_c$, where R$_c$ is an aryl group. "Heteroaryloxy" is intended to mean the radical —OR$_d$, where R$_d$ is a heteroaryl group. "Arylthio" is intended to mean the radical —SR$_c$, where R$_c$ is an aryl group. "Heteroarylthio" is intended to mean the radical —SR$_d$, where R$_d$ is a heteroaryl group. The alkyl, cycloalkyl, aryl, heterocycloalkyl and heteroaryl groups and the substituents containing these groups, as defined hereinabove, may be optionally substituted by at least one other substituent. The term "optionally substituted" is intended to expressly indicate that the specified group is unsubstituted or substituted by one or more suitable substituents. Various groups may be unsubstituted or substituted (i.e., they are optionally substituted) as indicated.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

All compounds of this invention contain at least one chiral center and may exist as single stereoisomers (e.g., single enantiomers or diastereomers), any mixture of stereosisomers (e.g., any mixture of enantiomers or diastereomers) or racemic mixtures thereof. All such single stereoisomers, mixtures and racemates are intended to be encompassed within the broad scope of the present invention. Where the stereochemistry of the chiral carbons present in the chemical structures illustrated herein is not specified, the chemical structure is intended to encompass compounds containing either stereoisomer of each chiral carbon. When used describe a particular compound, the term "optically pure" is used herein to indicate that the compound is substantially enantiomerically or diastereomerically pure. Compounds that are substantially enantiomerically pure contain at least 90% of a single isomer and preferably contain at least 95% of a single isomer. Compounds that are substantially diastereomerically pure contain at least 90% of a single isomer of each chiral carbon center present in the diastereomer, and preferably contain at least 95% of a single isomer of each chiral carbon. More preferably, when an optically active compound is desired, it contains at least 97.5% of a single isomer and, most preferably, at least 99% of the single isomer. Compounds identified herein as single stereoisomers are meant to describe compounds that are present in a form that contains at least 90% of a single isomer. The terms "racemate" and "racemate mixture" refer to a mixture of equal amounts of enantiomeric compounds, which encompass mixtures of enantiomers and mixtures of enantiomeric diastereomers.

The compounds of this invention may be obtained in stereochemically (e.g., enantiomerically or diastereomerically) pure or substantially stereochemically pure form. Such compounds may be obtained synthetically, according to the procedures described herein using optically pure or substantially optically pure materials. Alternatively, these compounds may be obtained by resolution/separation of a mixture of stereoisomers, including racemic mixtures, using conventional procedures. Exemplary methods that may be useful for the resolution/separation of stereoisomeric mixtures include chromatography and crystallization/re-crystallization. Other useful methods may be found in "Enantiomers, Racemates, and Resolutions," J. Jacques et al., 1981, John Wiley and Sons, New York, N.Y., the disclosure of which is incorporated herein by reference. Preferred stereoisomers of the compounds of this invention are described herein.

The compounds of this invention may also exhibit the phenomenon of tautomerism. The structural formulae herein may depicted one of the possible tautomeric forms but it should be understood that the invention nonetheless encompasses all tautomeric forms of the compound.

The invention also relates to prodrugs, pharmaceutically acceptable salts, pharmaceutically active metabolites, and pharmaceutically acceptable solvates of compounds of the Formula I, II, III, IV and V.

In the compounds of each of the above-described Formulas I to V, $R^c$ is defined to provide structures where m is 1 and p is 1–5 (i.e., both $A_2$ and $A_3$ are present), m is 0 and p is 0 (i.e., both $A_2$ and $A_3$ are absent), m is 0 and p is 1–5 (i.e., $A_2$ is absent and $A_3$ is present) and m is 1 and p is 0 (i.e., $A_2$ is present and $A_3$ is absent). Accordingly, one of ordinary skill in the are will recognize that when both $A_2$ and $A_3$ are present (m is 1 and p is 1–5), the dotted line between $A_1$ and $A_2$ represents a bond and the dotted line between $A_2$ and $A_3$ represents a bond and when both $A_2$ and $A_3$ are absent (m is 0 and p is 0); $A_2$, $A_3$ and the dotted line between these substituents are not present), the remaining dotted line in the structure between $A_1$ and $A_2$ represents a hydrogen (e.g., $A_1$ is $CH_2$ or NH). In embodiments of this invention when $A_2$ is absent and $A_3$ is present (m is 0 and p is 1–5), the dotted line between $A_1$ and $A_2$ represents a hydrogen and the dotted line between $A_2$ and $A_3$ represents a hydrogen (e.g., $A_1$ is $CH_2$ or NH and $A_3$ is $CH(R^h)(R^i)$, $NH(R^j)$, SH, S(O)H, $S(O)_2H$, or OH); and when $A_2$ is present and $A_3$ is absent (m is 1 and p is 0), the dotted line between $A_1$ and $A_2$ represents a bond and $A_2$ is $C(R^h)(R^i)(R^j)$, $N(R^i)(R^j)$, $S(R^i)$, $S(O)(R^i)$, $S(O)_2(R^i)$, or $O(R^i)$ or the dotted line between $A_2$ and $A_3$ represents a hydrogen and $A_2$ is $CH(R^h)(R^i)$, $NH(R^j)$, SH, S(O)H, $S(O)_2H$, or OH. In preferred embodiments of the compounds of each of the above-described Formulas, m is 1 and p is 1 or 2 or m is 0 and p is 0 or m is 1 and p is 0. More preferably, when m is 1 and p is 1 or 2, $A_2$ and $A_3$ are both $C(R^h)(R^i)$. More preferably, m is 1 and p is 1.

In especially preferred embodiments of formulas I to V, $R^c$ is selected from —$CH_2CH_2C(O)NH_2$; —$CH_2CH_2C(O)NH$-alkyl; —$CH_2NHC(O)CH_3$; and

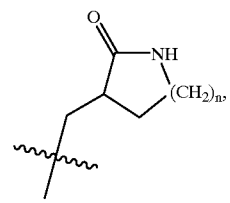

where n is 1 or 2. More preferably, $R^c$ is —$CH_2CH_2C(O)NH_2$ or

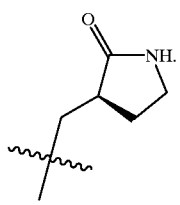

Especially preferred embodiments of this invention are those compounds where $R^c$ is

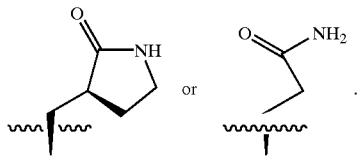 or 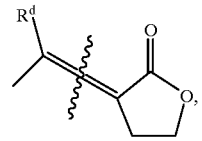

In the compounds of formulas I to V, $R^d$ and each $R^b$ are preferably H. In the compounds of formulas IV and V, $R^e$ is preferably H or $(C_1-C_6)$ alkyl.

In each of the formulas I to V, Z and $Z^1$ are each independently H, alkyl, where the alkyl is unsubstituted or substituted with one or more suitable substituents, $-CO_2{}^n$, where $R^n$ is as defined above, or Z and $Z^1$, taken together with the atom to which they are attached, form a heterocycloalkyl group, as defined above, which may be optionally substituted. In one useful embodiment of the compounds of this invention, Z and/or $Z^1$ may be $-C(S)OR^n$, where $R^n$ is as defined above. Such compounds may be prepared using procedures described in K. Hartke, et al., Leibigs Ann. Chem., 321–330 (1989) and K. Hartke, et al., Synthesis, 960–961 (1985). More preferably, the heterocycloalkyl group may optionally contain O, N, S and/or P and may be substituted by one or more of oxo (keto) or thioketo. In another preferred embodiment of this invention, Z and $Z^1$ are each independently selected from H, lower alkyl which is unsubstituted or substituted with one or more suitable substituents, $-CO_2H$, $-CO_2$-alkyl and $-CO_2$-cycloalkyl, or taken together with the atom to which they are attached form a heterocycloalkyl group, which is optionally substituted with one or more of keto or thioketo. In other preferred embodiments of this invention, Z and $Z^1$ are not both H. Most preferably, $Z^1$ is H or lower alkyl and Z is a $-CO_2H$, $-CO_2$-alkyl, $-CO_2$-alkylaryl, $-CO_2$-alkylheteroaryl, $-CO_2$-cycloalkyl group, where the lower alkyl, -alkyl, -cycloalkyl, -alkylaryl and -alkylheteroaryl moieties thereof are unsubstituted or substituted with one or more suitable substituents, or $Z^1$ and Z taken together with the atom to which they are attached form a heterocycloalkyl group, which may be optionally substituted. Exemplary Z groups include, but are not limited to: substituted and unsubstituted $-CO_2$-alkyl groups, which include straight- and branched-chain alkyl groups such as ethoxycarbonyl, t-butoxycarbonyl, isopropoxycarbonyl and (2,2-dimethylpropyl)-oxycarbonyl, where the ethoxy, t-butoxy, isopropoxy, and (2,2-dimethylpropyl)-oxy moieties thereof are unsubstituted or substituted with one or more suitable substituents; and include substituted and unsubstituted straight and branched-chain arylalkyl and heteroarylalkyl groups, such as benzyloxycarbonyl and pyridylmethyleneoxycarbonyl, where the benzyl and pyridylmethylene moieties thereof are unsubstituted or substituted with one or more suitable substituents; and include substituted and unsubstituted $-CO_2$-cycloalkyl groups such as cyclobutyloxycarbonyl, cyclopentyloxycarbonyl, cyclohexyloxycarbonyl and cycloheptyloxycarbonyl groups, where the cyclobutyl, cyclopentyl, cyclohexyl and cycloheptyl moieties thereof are unsubstituted or substituted with one or more suitable substituents, or $Z^1$ and Z taken together with the atom to which they are attached form

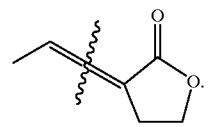

in Formulas I to V.

In another embodiment of this invention, $Z^1$ is H and Z is $-CO_2CH_2CH_3$, $-CO_2(CH(CH_3)_2)$, $-CO_2(C(CH_3)_3)$, $-CO_2CH_2(C(CH_3)_3)$, $-CO_2(cyclo-C_5H_9)$ or $Z^1$ and Z taken together with the atom to which they are attached form In yet another embodiment of this invention, $Z^1$ is H and Z is $-CO_2CH_2CH_3$.

Specific embodiments of this invention comprise compounds having formula II, wherein $R^{a1}$ is a $(C_3-C_8)$ cycloalkyl, heterocycloalkyl, aryl or heteroaryl group, wherein the $(C_3-C_8)$cycloalkyl, heterocycloalkyl, aryl or heteroaryl group is unsubstituted or substituted with one or more substituents independently selected from $(C_1-C_4)$ alkyl, aryl$(C_1-C_4)$alkyl, aryl, $(C_3-C_8)$cycloalkyl, heterocycloalkyl, heteroaryl, halo, hydroxyl, nitro, amino, $(C_1-C_4)$alkylamino, di-$(C_1-C_4)$alkylamino, aryl$(C_1-C_4)$ alkoxy, aryloxy$(C_1-C_4)$alkyl, alkylenedioxy (as a substituent for aryl or heteroaryl), aryloxy, $(C_3-C_8)$cycloalkoxy, heteroaryloxy, $(C_1-C_4)$haloalkyl, $(C_1-C_4)$alkoxy, $(C_1-C_4)$ haloalkoxy, hydroxamino, $(C_1-C_4)$alkoxycarbonyl, $(C_1-C_4)$ alkylcarbonylamino, $(C_1-C_4)$alkylcarbonyl, mercapto, alkylthio or arylthio, where the $(C_1-C_4)$alkyl and $(C_3-C_8)$ cycloalkyl moieties thereof are optionally substituted by one or more of $(C_1-C_4)$alkyl (except for alkyl), halo, $(C_1-C_4)$ haloalkyl, $(C_1-C_4)$alkoxy, $(C_1-C_4)$haloalkoxy and the heterocycloalkyl, aryl or heteroaryl moieties thereof are unsubstituted or are optionally substituted by one or more substituents independently selected from alkyl, haloalkyl, alkylenedioxy, nitro, amino, hydroxamino, alkylamino, dialkylamino, halo, hydroxyl, alkoxy, haloalkoxy, aryloxy, mercapto, alkylthio or arylthio groups; preferably, $R^{a1}$ is a pyrazolyl, indolyl, chromenyl, benzofuranyl, benzothienyl, benzimidazolyl, triazolyl, quinolyl, thiazolidinyl, quinoxalinyl, phenyl or naphthyl group, where the pyrazolyl, indolyl, chromenyl, benzofuranyl, benzothienyl, benzimidazolyl, triazolyl, quinolyl, thiazolidinyl, quinoxalinyl, phenyl or naphthyl group is unsubstituted or substituted with one or more substituents independently selected from $(C_1-C_4)$alkyl, aryl$(C_1-C_4)$alkyl, aryl, halo, hydroxyl, nitro, amino, $(C_1-C_4)$alkylamino, di-$(C_1-C_4)$ alkylamino, $(C_1-C_4)$alkoxy, aryl$(C_1-C_4)$alkoxy, aryloxy $(C_1-C_4)$alkyl, methylenedioxy, aryloxy, $(C_1-C_4)$haloalkyl, $(C_1-C_4)$haloalkoxy, $(C_1-C_4)$alkoxycarbonyl, $(C_1-C_4)$ alkylcarbonylamino, or $(C_1-C_4)$alkylcarbonyl, where the $(C_1-C_4)$alkyl moieties thereof are optionally substituted by one or more of halo, $(C_1-C_4)$alkoxy or $(C_1-C_4)$haloalkoxy and the aryl moieties thereof are unsubstituted or are optionally substituted by one or more substituents independently selected from alkyl, haloalkyl, alkylenedioxy, nitro, amino, alkylamino, dialkylamino, halo, hydroxyl, alkoxy, haloalkoxy or aryloxy groups; more preferably, $R^{a1}$ is a is a pyrazolyl, indolyl, N-methylindolyl, chromenyl, benzofuranyl, benzothienyl, benzimidazolyl, N-methylbenzimidazolyl, triazolyl, quinolyl, thiazolidinyl, quinoxalinyl, phenyl or naphthyl group, where the pyrazolyl, indolyl, chromenyl, benzofuranyl, benzothienyl, benzimidazolyl, triazolyl, quinolyl, thiazolidinyl, quinoxalinyl, phenyl or naphthyl group is unsubstituted or substituted with one or more substituents independently selected from methyl, ethyl, benzyl, phenethyl, phenyl, naphthyl, halo, hydroxyl, nitro, amino, methylamino, di-methylamino, methoxy, benzyloxy, methylenedioxy, $(C_1-C_4)$haloalkyl, $(C_1-C_4)$haloalkoxy, methoxycarbonyl, methylcarbonylamino, benzoyloxymethylene (phenylcarbonyloxymethyl-)or methylcarbonyl;

$R^d$ and each $R^b$ are independently H or $C_1-C_4$ alkyl; preferably $R^d$ and each $R^b$ are H; or a prodrug, pharmaceutically acceptable salt, pharmaceutically active metabolite, or pharmaceutically acceptable solvate of said compound.

Other specific embodiments of this invention comprise the compounds having the formula III, wherein $R^{a2}$ is a $(C_1-C_4)$alkyl, aryl or heteroaryl group, wherein the $(C_1-C_4)$ alkyl, $(C_3-C_8)$cycloalkyl, heterocycloalkyl, aryl and heteroaryl group is unsubstituted or substituted with one or more suitable substituents; preferably, $R^{a2}$ is a $(C_1-C_4)$alkyl, phenyl or naphthyl group, where the $(C_1-C_4)$alkyl group is unsubstituted or substituted with one or more substituents independently selected from halo, $C_1-C_4$ alkoxy, $C_1-C_4$ haloalkoxy, $C_1-C_4$ alkoxycarbonyl, and the phenyl or naphthyl group is unsubstituted or substituted with one or more substituents independently selected from halo, $C_1-C_4$ alkyl, $C_1-C_4$ haloalkyl, $C_1-C_4$ alkoxy, $C_1-C_4$ haloalkoxy, methylenedioxy and phenoxy; in specific embodiments, $R^{a2}$ is a naphthyl, phenoxyphenyl, 3,5-dimethoxy-phenyl, 3,5-dimethylphenyl or an ethoxycarbonyl-substituted branched $(C_1-C_6)$ alkyl moiety (derived from the ethyl ester of valine);

$R^d$ and each $R^b$ are independently H or $C_1-C_4$ alkyl; preferably $R^d$ and each $R^b$ are H; or a prodrug, pharmaceutically acceptable salt, pharmaceutically active metabolite, or pharmaceutically acceptable solvate of said compound.

Additional specific embodiments of this invention comprise compounds having the formula IV, wherein $R^{a3}$ is a aryl, heterocycloalkyl, heteroaryl or arylaminocarbonyl group, wherein the aryl, heterocycloalkyl, heteroaryl or arylaminocarbonyl group is unsubstituted or substituted with one or more substituents independently selected from $(C_1-C_4)$alkyl, aryl, halo, hydroxyl, nitro, amino, di-$(C_1-C_4)$ alkylamino $(C_1-C_4)$alkoxy, alkylenedioxy (as a substituent for aryl or heteroaryl), aryloxy, where the $(C_1-C_4)$alkyl or aryl moieties thereof are unsubstituted or optionally substituted by one or more of $(C_1-C_4)$alkyl (except for alkyl), halo, $(C_1-C_4)$haloalkyl, $(C_1-C_4)$alkoxy, $(C_1-C_4)$haloalkoxy, alkylenedioxy groups; in specific embodiments, $R^{a3}$ is a phenyl or phenylaminocarbonyl group, where the phenyl group or phenyl moiety of the phenylaminocarbonyl group is unsubstituted or substituted with one or more substituents independently selected from $(C_1-C_4)$alkyl, halo, hydroxyl, nitro, $(C_1-C_4)$alkoxy and alkylenedioxy; in more specific embodiments, $R^{a3}$ is a phenyl or phenylaminocarbonyl group, where the phenyl group or phenyl moiety of the phenylaminocarbonyl group is unsubstituted or substituted with one or more substituents independently selected from methyl, halo, hydroxyl, nitro, methoxy, and alkylenedioxy;

$R^d$, $R^e$ and each $R^b$ are independently H or $C_1-C_4$ alkyl; preferably $R^d$ and each $R^b$ are H; or a prodrug, pharmaceutically acceptable salt, pharmaceutically active metabolite, or pharmaceutically acceptable solvate of said compound.

Yet another specific embodiment of this invention comprises compounds having the formula V, wherein $R^{a4}$ is an aryloxy, heteroaryloxy, $(C_1-C_4)$alkoxy, $(C_3-C_8)$ cycloalkoxy, heterocycloalkyloxy, $(C_3-C_8)$cycloalkyl, heteroaryl or $(C_1-C_4)$alkoxycarbonyl group, wherein the aryloxy, heteroaryloxy, $(C_1-C_4)$alkoxy, $(C_3-C_8)$ cycloalkoxy, heterocycloalkyloxy, $(C_3-C_8)$cycloalkyl, heteroaryl or $(C_1-C_4)$alkoxycarbonyl group is unsubstituted or substituted with one or more substituents independently selected from $(C_1-C_4)$alkyl, aryl, $(C_3-C_8)$cycloalkyl, heterocycloalkyl, heteroaryl, halo, hydroxyl, $(C_1-C_4)$ alkoxy, alkylenedioxy (as a substituent for aryl or heteroaryl), aryloxy, $(C_3-C_8)$cycloalkoxy, heteroaryloxy and $(C_1-C_4)$alkoxycarbonyl, where the $(C_1-C_4)$alkyl, aryl, $(C_3-C_8)$cycloalkyl, heterocycloalkyl, heteroaryl moieties thereof are optionally substituted by one or more of $(C_1-C_4)$ alkyl (except for alkyl), halo, $(C_1-C_4)$haloalkyl, $(C_1-C_4)$ alkoxy, $(C_1-C_4)$haloalkoxy, alkylenedioxy, aryl or heteroaryl, where the aryl or heteroaryl is unsubstituted or substituted with one or more substituents independently selected from alkyl, haloalkyl, alkylenedioxy, nitro, amino, hydroxamino, alkylamino, dialkylamino, halo, hydroxyl, alkoxy, haloalkoxy, aryloxy, mercapto, alkylthio or arylthio groups; in specific embodiments, $R^{a4}$ is a phenoxy, or $(C_1-C_4)$alkoxycarbonyl group, wherein the phenyl moiety of the phenoxy group is unsubstituted or substituted with one or more substituents independently selected from halo and $(C_1-C_4)$alkoxy;

$R^d$ and $R^b$ are independently H or $C_1-C_4$ alkyl; preferably $R^d$ and each $R^b$ are H;

$R^e$ is H or $C_1-C_6$ alkyl; in specific embodiments $R^e$ is H or isobutyl, or a prodrug, pharmaceutically acceptable salt, pharmaceutically active metabolite, or pharmaceutically acceptable solvate of said compound.

In each of the above-described embodiments of the subject invention, $R^c$ is selected from —$CH_2CH_2C(O)NH_2$; —$CH_2CH_2C(O)NH$-alkyl; —$CH_2NHC(O)CH_3$; and

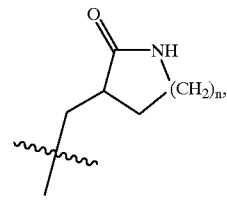

where n is 1 or 2; preferably, $R^c$ is —$CH_2CH_2C(O)NH_2$ or

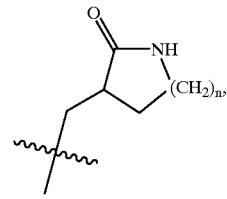

where n is 1; more preferably, $R^c$ is —$CH_2CH_2C(O)NH_2$ or

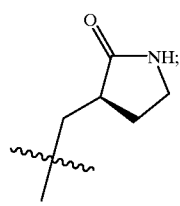

even more preferably, $R^c$ is

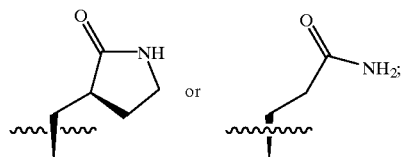

and $Z^1$ is H or $C_1$–$C_4$ alkyl and Z is —$CO_2$-alkyl, —$CO_2$-cycloalkyl, —$CO_2$-alkylaryl or —$CO_2$-alkylheterocycloaryl, or $Z^1$ and Z taken together with the atom to which they are attached form

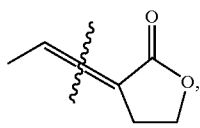

preferably, $Z^1$ is H and Z is —$CO_2CH_2CH_3$, —$CO_2(CH(CH_3)_2)$, —$CO_2(C(CH_3)_3)$, —$CO_2CH_2(C(CH_3)_3)$, —$CO_2$(cyclo-$C_5H_9$) or $Z^1$ and Z taken together with the atom to which they are attached form

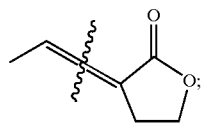

more preferably, $Z^1$ is H and Z is —$CO_2CH_2CH_3$ or $Z^1$ and Z taken together with the atom to which they are attached form

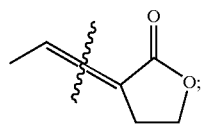

even more preferably, $Z^1$ is H and Z is —$CO_2CH_2CH_3$.

The compounds have antiviral activity against picornaviruses such as human rhinoviruses, human polioviruses, human coxsackieviruses, human echoviruses, human and bovine enteroviruses, encephalomyocarditis viruses, meningitis virus, foot and mouth viruses, hepatitis A virus, and others. Preferably, such compounds, pharmaceutically acceptable salts, prodrugs, active metabolites, and solvates have antipicornaviral activity, more preferably antirhinoviral activity, corresponding to an $EC_{50}$ less than or equal to 100 $\mu$M in the H1-HeLa cell culture assay, more preferably corresponding to an $EC_{50}$ less than or equal to 10 $\mu$M in the H1-HeLa cell culture assay.

Preferred embodiments of this invention comprise the compounds depicted by the formula:

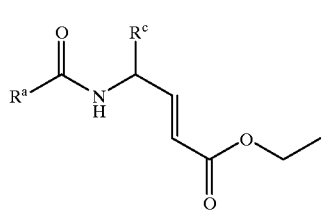

I-a where $R^a$ and $R^c$ are as defined above.

Other preferred embodiments of this invention comprise the compounds depicted by the formula:

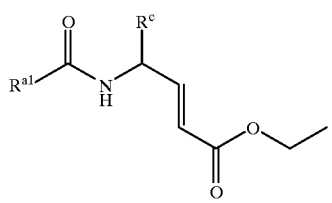

II-a where $R^{a1}$ and $R^c$ are as defined above.

Other preferred embodiments of this invention comprise the compounds depicted by the formula:

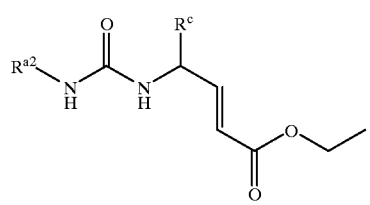

III-a where $R_{a2}$ and $R^c$ are as defined above.

Other preferred embodiments of this invention comprise the compounds depicted by the formula:

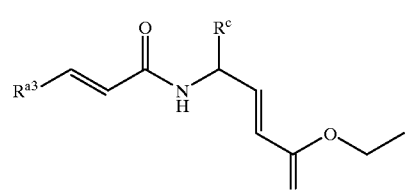

IV-a where $R^{a3}$ and $R^c$ are as defined above.

In other preferred embodiments of compounds of formula I, $R^a$ is selected from:

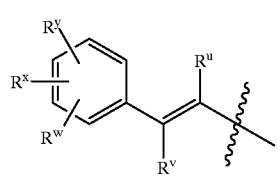

where $R^u$ and $R^v$ are selected from H, F, $CH_3$, and $C_2H_5$; and $R^w$, $R^x$, and $R^y$ are H or a substituent selected from lower alkyl, lower alkoxy, amino, halo, nitro, and hydroxy.

Yet other preferred embodiments of this invention comprise the compounds depicted by the formula:

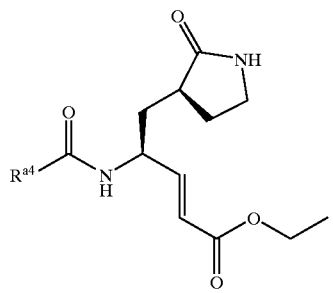

V-a where $R^{a4}$ is selected from a monosubstituted alkyl or alkoxy, where the substituent is aryl or alkyl. Particularly preferred is $R^{a4}$ is —O-aryl or -aryl, where aryl is phenyl, unsubstituted or substituted with one or more suitable substituents.

Examples of preferred compounds of formula I include:

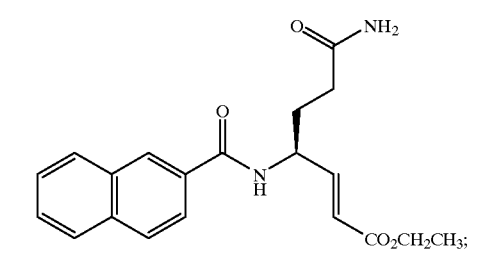

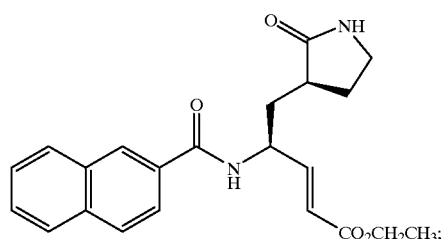

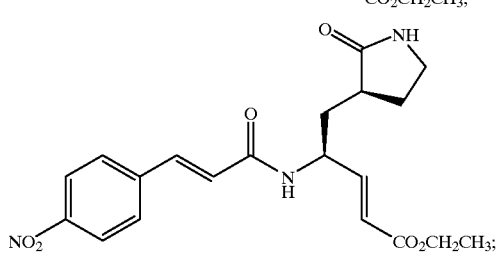

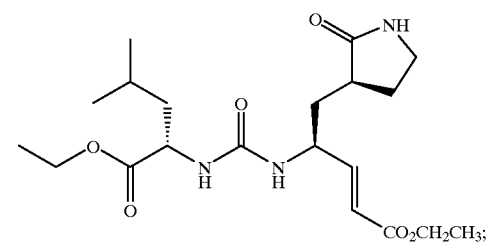

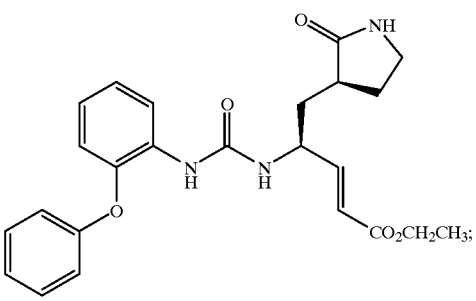

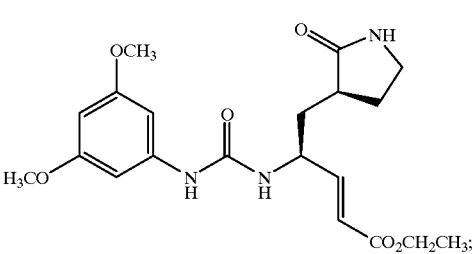

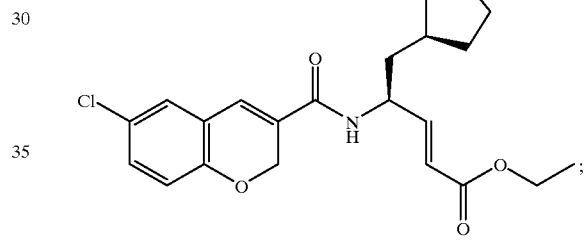

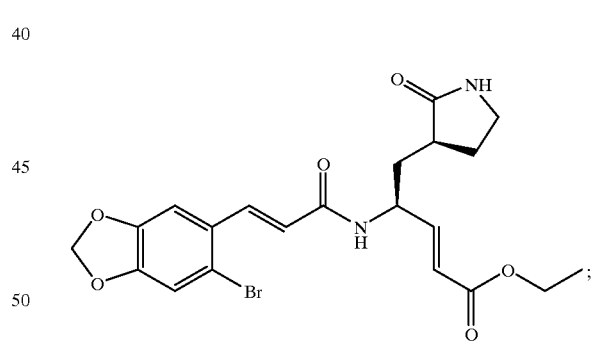

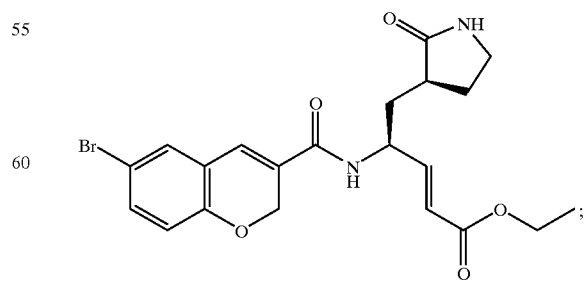

and

-continued

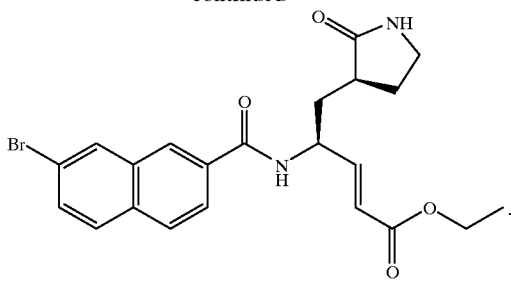

The present invention is also directed to a method of inhibiting picornaviral 3C protease activity, comprising contacting the protease with an effective amount of a compound of formula I, or a pharmaceutically acceptable salt, prodrug, pharmaceutically active metabolite, or solvate thereof. For example, picornaviral 3C protease activity may be inhibited in mammalian tissue by administering a compound of formula I or a pharmaceutically acceptable salt, prodrug, pharmaceutically active metabolite, or solvate thereof. More preferably, the present method is directed at inhibiting rhinoviral protease activity.

A "prodrug" is intended to mean a compound that is converted under physiological conditions or by solvolysis or metabolically to a specified compound that is pharmaceutically active. A prodrug may be a derivative of one of the compounds of this invention that contains a moiety, such as for example —$CO_2R$, —$PO(OR)_2$ or —$C\!=\!NR$, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for example, an amido, carboxylic acid, or hydroxyl moiety with a suitable reagent. A "pharmaceutically active metabolite" is intended to mean a pharmacologically active compound produced through metabolism in the body of a specified compound. Prodrugs and active metabolites of compounds of this invention of the above-described Formulas may be determined using techniques known in the art, for example, through metabolic studies. See, e.g., "Design of Prodrugs," (Bundgaard, ed.), 1985, Elsevier Publishers B. V., Amsterdam, The Netherlands. A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates (mesylates), propanesulfonates, naphthalene-1-sulfonates, naphthalene-2-sulfonates, and mandelates. A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, and solvates may exist in different crystal forms, all of which are intended to be within the scope of the present invention and specified formulas.

The activity of the inventive compounds as inhibitors of picornaviral 3C protease activity may be measured by any of the suitable methods known to those skilled in the art, including in vivo and in vitro assays. An example of a suitable assay for activity measurements is the antiviral H1-HeLa cell culture assay described herein.

Administration of the compounds of the formula I and their pharmaceutically acceptable prodrugs, salts, active metabolites, and solvates may be performed according to any of the accepted modes of administration available to those skilled in the art. Illustrative examples of suitable modes of administration include oral, nasal, parenteral, topical, transdermal, and rectal. Oral and intranasal deliveries are especially preferred.

An inventive compound of formula I or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use. In preferred embodiments, the inventive pharmaceutical compositions are delivered intranasally in the form of suspensions.

The compounds (active ingredients) may be formulated into solid oral dosage forms which may contain, but are not limited to, the following active ingredients: diluents (i.e., lactose, corn starch, microcrystalline cellulose), binders (i.e., povidone, hydroxypropyl methylcellulose), disintegrants, (i.e., crospovidone, croscarmellose sodium), lubricants (i.e., magnesium stearate, stearic acid), colorants (FD&C lakes or dyes). Alternatively, the compounds may be formulated into other oral dosage forms including liquids, suspensions, emulsions, or soft gelatin capsules, with each dosage form having a unique set of ingredients.

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a non-aqueous or aqueous liquid suspension.

A dose of the pharmaceutical composition contains at least a therapeutically effective amount of the active compound (i.e., a compound of formula I or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of picornaviral 3C protease activity, by any known or suitable method of administering the dose, including topically, for example, as an ointment or cream; orally; rectally, for example, as a suppository; parenterally by injection; or continuously by intravaginal, intranasal, intrabronchial, intraaural, or intraocular infusion. A "therapeutically effective amount" is intended to mean the amount of an inventive compound that, when administered to a mammal in need thereof, is sufficient to effect treatment for disease conditions alleviated by the inhibition of the activity of one or more picornaviral 3C proteases, such as human rhinoviruses, human poliovirus, human coxsackieviruses, encephalomyocarditis viruses, menigovirus, and hepatitis A virus. The amount of a given compound of the invention that will be therapeutically effective will vary depending upon factors such as the particular compound, the disease condition and the severity thereof, the identity of the mammal in need thereof, which amount may be routinely determined by artisans.

Syntheses

Examples of various preferred compounds of formula I are set forth below. The structures of the compounds of the following examples were confirmed by one or more of the following: proton magnetic resonance spectroscopy, infrared spectroscopy, elemental microanalysis, mass spectrometry, thin layer chromatography, melting-point determination, and boiling-point determination.

Proton magnetic resonance ($^1$H NMR) spectra were determined using a Bruker or a Varian UNITYplus 300 spectrometer operating at a field strength of 300 megahertz (MHz). Chemical shifts are reported in parts per million (ppm, δ) downfield from an internal tetramethylsilane standard. Alternatively, $^1$H NMR spectra were referenced to residual protic solvent signals as follows: $CHCl_3$=7.26 ppm; DMSO=2.49 ppm; $C_6HD_5$=7.15 ppm. Peak multiplicities are designated as follows: s=singlet; d=doublet; dd=doublet of doublets; t=triplet; q=quartet; br=broad resonance; and m=multiplet. Coupling constants are given in Hertz. Infrared absorption (IR) spectra were obtained using a Perkin-Elmer 1600 series FTIR spectrometer. Elemental microanalyses were performed by Atlantic Microlab Inc. (Norcross, Ga.); results of the microanalyses are stated within ±0.4% of the theoretical values. Flash column chromatography was performed using Silica gel 60 (Merck Art 9385). Analytical thin layer chromatography (TLC) was performed using precoated sheets of Silica 60 $F_{254}$ (Merck Art 5719). Melting points (abbreviated as mp) were determined on a Mel-Temp apparatus and are uncorrected. All reactions were performed in septum-sealed flasks under a slight positive pressure of argon, unless otherwise noted. All commercial reagents were used as received from their respective suppliers.

In addition, for convenience a number of abbreviations are used. Solvents are denoted $CH_3OH$ (methanol); DME (ethylene glycol dimethyl ether); DMF (N,N-dimethylformamide); DMSO (dimethylsulfoxide); $Et_2O$ (diethyl ether); EtOAc (ethyl acetate); EtOH (ethanol); and MTBE (tert-butyl methyl ether). Certain substituents are referred to as Ac (acetyl); Me (methyl); Ph (phenyl); and Tr (triphenylmethyl). Protecting groups are abbreviated Cbz (benzyloxycarbonyl) and Boc (tert-butoxycarbonyl).

Various reagents used were denoted BINAP (2,2'-bis(diphenylphosphino)-1,1'-binaphthyl); DBU (1,8-diazabicyclo[5.4.0]undec-7-ene); DCC (dicyclohexylcarbodiimide); DDQ (2,3-dichloro-5,6-dicyano-1,4-benzoquinone); DIBAH (diisobutyl aluminum hydride); DIEA (N,N-diisopropylethylamine); DMAP (4-dimethylaminopyridine); EDC (1-(3-dimethylaminopropyl)-3-ethylcarbodiimide hydrochloride); HATU (O-(7-azabenzotriazol-1-yl)-N,N,N',N'-tetramethyluronium hexafluorophosphate); HOBt (1-hydroxybenzotriazole hydrate); IBX (1,1-dihydro-1,2-benziodoxol-3(1H)-one); LiHMDS (lithium bis(trimethylsilyl)amide); Pd-C (10% palladium on carbon); PyBOP (benzotriazole-1-yl-oxy-tris-pyrrolidino-phosphonium hexafluorophosphate); TBAF (tert-butyl ammonium fluoride); TBSCl (tert-butyl dimethylsilyl chloride); and TFA (trifluoroacetic acid).

EXAMPLES

Example 1

Preparation of 4S-[(naphthalene-2-carbonyl)-amino]-5-(2-oxo-pyrrolidin-3S-yl)-pent-2-enoic acid ethyl ester

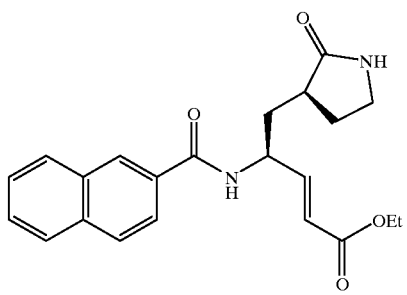

1

4S-Amino-5-(2-oxo-pyrrolidin-3S-yl)-pent-2-enoic acid ethyl ester (as disclosed in U.S. patent application Ser. No. 09/301,977 which is hereby incorporated by reference in its entirety) (30 mg, 0.13 mmol) in DMF (1 mL) was treated with diisopropylethyl amine (0.07 mL, 0.40 mmol), 2-naphthoic acid (22 mg, 0.13 mmol), and HATU (49 mg, 0.13 mmol), and held at room temperature for 1 h. The solution was washed with brine (5 mL), and extracted with EtOAc (10 mL). Evaporation yielded 34 mg of crude product. Purification by preparative reverse phase chromatography ($CH_3CN-H_2O$) yielded 20 mg (41%) of product 1. $^1$H NMR ($CDCl_3$) δ8.48 (1H, s), 8.01–7.85 (4H, m), 7.58–7.50 (2H, m), 6.98 (1H, dd, J=15.6, 5.3), 6.04 (1H, d, J=15.8), 4.85–4.78 (1H, m), 4.17 (2H, q, J=7.0), 3.39–3.34 (2H, m), 2.64–2.47 (2H, m), 2.17–2.06 (1H, m), 1.97–1.82 (3H, m), 1.34 (3H, t, J=7.0). MS (FAB) 381 (MH$^+$), 403 (MNa$^+$).

Example 2

Preparation of 4S-[(naphthalene-2-carbonyl)-amino]-5-(2-oxo-pyrrolidin-3-R-yl)-pent-2-enoic acid ethyl ester

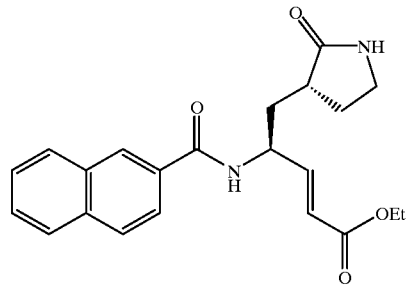

2

Compound 2 was prepared by the method described in Example 1, using 4S-amino-5-(2-oxo-pyrrolidin-3R-yl)-pent-2-enoic acid ethyl ester and 2-naphthoic acid as starting materials. $^1$H NMR (CDCl$_3$) δ9.18 (1H, d, J=7.1), 8.46 (1H, s), 8.05–7.83(4H, m), 7.58–7.45 (2H, m), 6.99 (1H, dd, J=15.6, 4.3), 6.37 (1H, s), 6.02 (1H, dd, J=15.6, 1.5), 5.18–5.08 (1H, m), 4.17 (2H, q, J=7.1), 3.40–3.30 (2H, m), 2.72–2.60 (H, m), 2.40–2.28 (1H, m), 2.20–2.00 (2H, m), 2.00–1.85 (1H, m), 1.28 (3H, t, J=7.1), MS (FAB) 381.1810 (MH$^+$, calcd. 381.1814), 403 (MNa$^+$).

Example 3

Preparation of 4S-[3-(3-bromo-phenyl)-acryloylamino]-5-(2-oxo-pyrrolidin-3S-yl)-pent-2-enoic acid ethyl ester

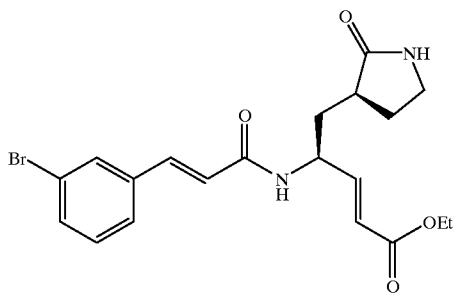

3

Compound 3 was prepared according to the method of Example 1, using 3-bromocinnamic acid. $^1$H NMR (CDCl$_3$) δ7.67 (1H, s), 7.53 (1H, d, J=15.6), 7.50–7.38 (2H, m), 7.22 (1H, t, J=7.8), 6.89 (1H, dd, J=15.6, 5.3), 6.47 (1H, d, J=15.7), 5.98 (1H, d, J=15.6), 4.74–4.64 (1H, m), 4.17 (2H, q, J=7.1), 3.42–3.35 (2H, m), 2.60–2.40 (2H, m), 2.10–1.70 (3H, m), 1.26 (3H, t, J=7.1). MS (FAB) 435 (MH$^+$), 457 (MNa$^+$).

Example 4

Preparation of N-[3-ethoxycarbonyl-1S-(2-oxo-pyrrolidin-3R-ylmethyl)-ally]-terephthalamic acid methyl ester

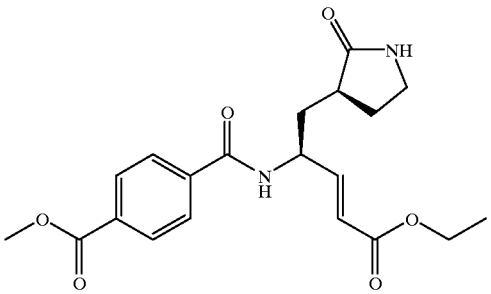

4

Compound 4 was prepared according to the method of Example 1, using terephthalic acid methyl ester. $^1$H NMR (CDCl$_3$) δ8.38 (1H, d, J=6.4), 8.10 (2H, d, J=8.5), 7.98 (2H, d, J=8.5), 6.92 (1H, dd, J=15.7, 5.5), 6.77 (1H, s), 6.01 (1H, dd, J=15.7, 1.4), 4.85–4.74 (1H, m), 4.17 (2H, q, J=7.1), 3.94 (3H, s), 3.50–3.40 (2H, m), 2.72–2.60 (1H, m), 2.58–2.42 (1H, m), 2.18–2.05 (1H, m), 2.02–1.80 (2H, m), 1.27 (3H, t, J=7.1), MS (FAB) 389.1709 (MH$^+$, calcd. 389.1713), 411 (MNa$^+$).

Example 5

Preparation of 4S-[3-(3,4-dimethoxy-phenyl)-acryloylamino]-5-(2-oxo-pyrrolidin-3S-yl)-pent-2-enoic acid ethyl ester

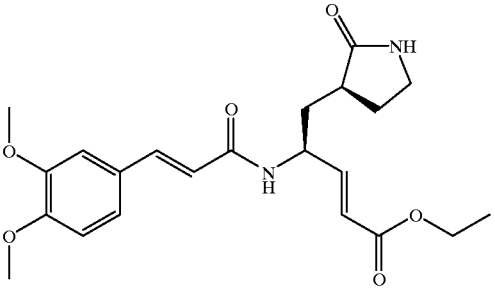

5

Compound 5 was prepared according to the method of Example 1, using 3,4-dimethoxycinnamic acid. $^1$H NMR (CDCl$_3$) δ7.58 (1H, d, J=7.0), 7.34 (1H, s), 7.15–7.00 (2H, m), 6.95–6.80 (2H, m), 6.37 (1H, d, J=15.7), 5.99 (1H, J=15.5), 5.60 (1H, s), 4.88–4.70 (1H, m), 4.17 (2H, q, J=7.1), 3.90 (6H, s), 3.48–3.30 (2H, m), 2.70–2.40 (2H, m), 2.10–1.55 (3H, m), 1.27 (3H, t, J=7.1). MS (FAB) 417.2008 (MH$^+$, calcd. 417.2026), 439 (MNa$^+$).

Example 6

Preparation of 4S-[(5-bromo-pyridine-3-carbonyl)-amino]-5-(2-oxo-pyrrolidin-3S-yl)-pent-2-enoic acid ethyl ester

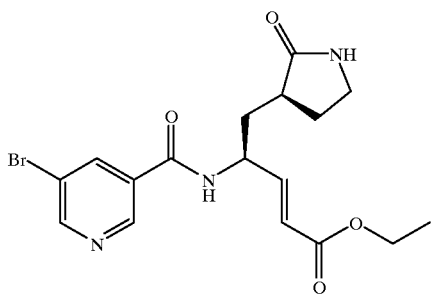

6

Compound 6 was prepared according to the method of Example 1, using 5-bromonicotinic acid. $^1$H NMR (CDCl$_3$) δ9.27 (1H, d, J=5.4), 9.12 (1H, s), 8.77 (1H, s), 8.45 (1H, s), 6.91 (1H, dd, J=15.6, 5.7), 6.15 (1H, s), 5.99 (1H, d, J=15.7), 4.72–4.66 (1H, m), 4.18 (2H, q, J=7.1), 3.42–3.38 (2H, m), 2.60–2.45 (2H, m), 2.17–1.80 (3H, m), 1.27 (3H, t, J=7.1). MS (ES) 410 (MH$^+$).

Example 7

Preparation of 4S-[(3-hydroxyquinoxaline-2-carbonyl)-amino]-5-(2-oxopyrrolidin-3S-yl)-pent-2-enoic acid ethyl ester

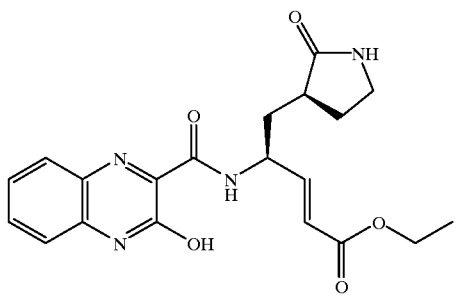

7

Compound 7 was prepared according to the method of Example 1, using 3-hydroxyquinoline-2-carboxylic acid. $^1$H NMR (CDCl$_3$) δ9.80 (1H, s), 7.98 (1H, d, J=7.1), 7.50–7.30 (4H, m), 6.90 (1H, dd, J=15.6, 5.3), 6.50 (1H, s), 6.01 (1H, d, J=15.6), 5.10–5.02 (1H, m), 4.17 (2H, q, J=7.1), 3.39–3.30 (2H, m), 2.60–2.47 (2H, m), 2.17–2.01 (1H, m), 1.97–1.82 (2H, m), 1.27 (3H, t, J=7.1). MS (ES) 399 (MH$^+$).

Example 8

Preparation of 4S-[(5-ethyl-1H-indole-2-carbonyl)-amino]-5-(2-oxo-pyrrolidin-3S-yl)-pent-2-enoic acid ethyl ester

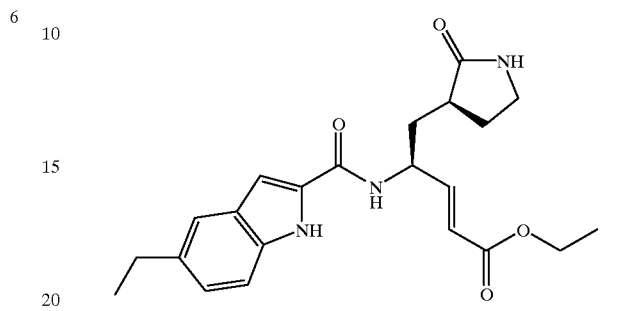

8

Compound 8 was prepared according to the method of Example 1, using 5-ethyl-1H-indole-2-carboxylic acid. $^1$H NMR (CDCl$_3$) δ9.15 (1H, s), 8.60 (1H, d, J=5.7), 7.44 (1H, s), 7.35–7.08 (3H, m), 6.95 (1H, dd, J=15.6, 5.7), 6.04 (1H, d, J=15.6), 5.93 (1H, s), 4.75–4.70 (1H, m), 4.17 (2H, q, J=7.1), 3.40–3.36 (2H, m), 2.73 (2H, q, J=7.5), 2.68–2.42 (2H, m), 2.14–1.81 (3H, m), 1.33–1.24 (6H, m). MS (FAB) 398 (MH$^+$), 420 (MNa$^+$).

Example 9

Preparation of 4S-(3-benzo[1,3]dioxol-5-yl-acryloylamino)-5-(2-oxo-pyrrolidin-3S-yl)-pent-2-enoic acid ethyl ester

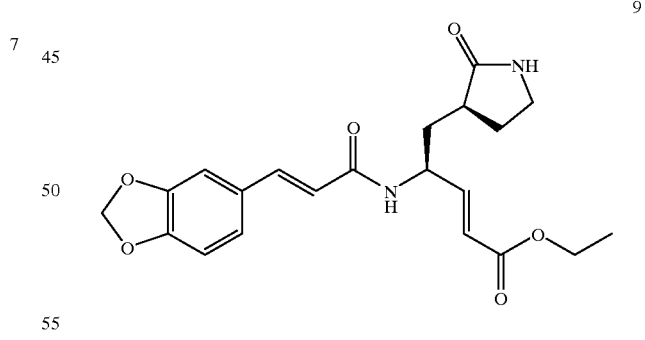

9

Compound 9 was prepared according to the method of Example 1, using 3,4-methylenedioxycinnamic acid. $^1$H NMR (CDCl$_3$) δ7.54 (1H, d, J=6.3), 7.51 (1H, d, J=15.1), 7.01 (1H, s), 6.97 (1H, d, J=8.1), 6.89 (1H, dd, J=15.7, 5.3), 6.78 (1H, d, J=7.9), 6.35 (1 H, d, J=15.6), 6.01–5.93 (4H, m), 4.74–4.72 (1H, m), 4.20 (2H, q, J=7.1), 3.37–3.34 (2H, m), 2.53–2.42 (2H, m), 2.04–1.70 (3H, m), 1.26 (3H, t, J=7.1). MS (FAB) 423.1545 (MNa$^+$, calcd. 423.1532), 423 (MNa$^+$).

Example 10

Preparation of 4-[(1H-benzoimidazole-2-carbonyl)-amino]-5-(2-oxo-pyrrolidin-3S-yl)-pent-2-enoic acid ethyl ester

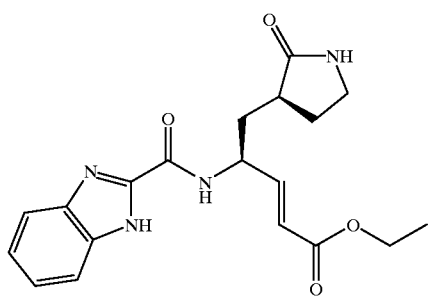

10

Compound 10 was prepared according to the method of Example 1, using 1H-benzoimidazole-2-carboxylic acid. $^1$H NMR (CDCl$_3$) δ8.60 (1H, s), 7.60–7.30 (5H, m), 6.90 (1H, dd, J=15.7, 5.7), 6.13 (1H, s), 6.05 (1H, d, J=15.7), 4.80–4.75 (1H, m), 4.10 (2H, q, J=7.1), 3.30–3.20 (2H, m), 2.50–1.70 (5H, m), 1.27 (3H, t, J=7.1). MS (FAB) 371.1706 (MH$^+$, calcd. 371.1719), 393 (MNa$^+$).

Example 11

Preparation of 4S-[3-(4-chloro-phenyl)-acryloylamino]-5-(2-oxo-pyrrolidin-3S-yl)-pent-2-enoic acid ethyl ester

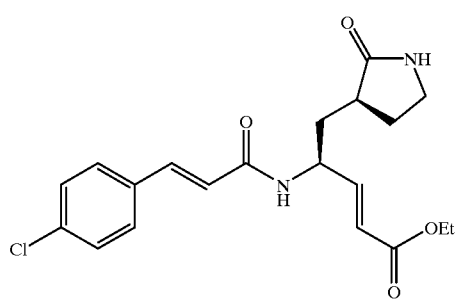

11

Compound 11 was prepared according to the method of Example 1, using 4-chlorocinnamic acid. $^1$H NMR (CDCl$_3$) δ7.59 (1H, s), 7.50 (1H, d, J=15.7), 7.38 (2H, d, J=8.8), 7.25 (2H, d, J=8.4), 6.79 (1H, dd, J=15.7, 5.3), 6.40 (1H, d, J=15.8), 5.90 (1H, dd, J=14.2, 1.4), 5.88–5.48 (1H, s), 5.69–5.60 (1H, m), 4.10 (2H, q, J=7.1), 3.35–3.27 (2H, m), 2.58–2.37 (2H, m), 1.99–1.65 (3H, m), 1.20 (3H, t, J=7.1). MS (FAB) 391.1429 (MH$^+$, calcd 391.1425), 413 (MNa$^+$).

Example 12

Preparation of 5-(2-oxo-pyrrolidin-3S-yl)-4S-(3-p-tolyl-acryloylamino)-pent-2-enoic acid ethyl ester

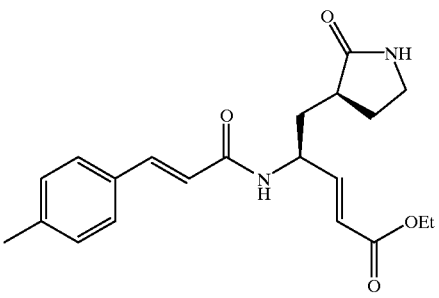

12

Compound 12 was prepared according to the method of Example 1, using 4-methylcinnamic acid. $^1$H NMR (CDCl$_3$) δ7.63 (1H, d, J=15.6), 7.43 (2H, d, J=8.7), 7.31 (1H, d, J=7.3), 7.18 (2H, d, J=8.4), 6.97 (1H, s), 6.88 (1H, d, J=15.1), 6.43 (1H, d, J=15.6), 5.99 (1H, d, J=15.7), 4.84–4.77 (1H, m), 4.19 (2H, q, J=7.1), 3.46–3.48 (2H, m), 2.68–2.47 (2H, m), 2.36 (3H, s), 2.11–1.71 (3H, m), 1.27 (3H, t, J=7.1). MS (FAB) 371.1967 (MH$^+$, calcd 371.1971) 393 (MNa$^+$).

Example 13

Preparation of 4S-[(3-acetyl-2-phenyl-thiazolidine-4-carbonyl)-amino]-5-(2-oxo-pyrrolidin-3S-yl)-pent-2-enoic acid ethyl ester

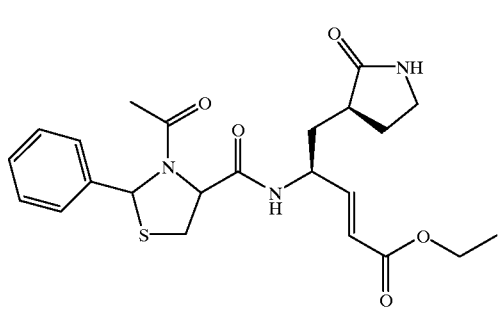

13

Compound 13 was prepared according to the method of Example 1, using 3-acetyl-2-phenylthiazolidine-4-carboxylic acid. $^1$H NMR (CDCl$_3$) δ8.07 (1H, d, J=7.0), 7.80–7.27 (5H, m), 7.10 (1H, d, J=16.0), 6.48 (1H, s), 6.20–6.05 (2H, m), 5.01 (1H, s), 4.80–4.75 (1H, m), 4.20 (2H, q, J=7.1), 3.70–3.30 (5H, m), 2.80–1.90 (4H, m), 2.15 (3H, s), 1.30 (3H, t, J=7.1). MS (FAB) 460.1894 (MH$^+$, calcd. 460.1906).

Example 14

Preparation of 4S-[(5-bromo-benzofuran-2-carbonyl)-amino]-5-(2-oxo-pyrrolidin-3S-yl)-pent-2-enoic acid ethyl ester

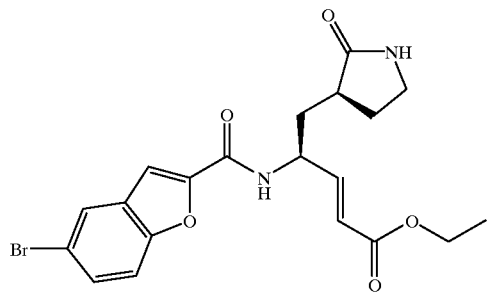

14

Compound 14 was prepared according to the method of Example 1, using 5-bromobenzofuran-2-carboxylic acid. $^1$H NMR (CDCl$_3$) δ7.85 (1H, d, J=7.1), 7.60 (1H, s), 7.40–7.20 (3H, m), 6.80 (1H, dd, J=15.6, 5.7), 5.90 (1H, d, J=15.7), 5.60 (1H, s), 4.75–4.72 (1H, m), 4.19 (2H, q, J=7.1), 3.30–3.20 (2H, m), 2.50–2.30 (2H, m), 2.10–1.60 (3H, m), 1.27 (3H, t, J=7.1). MS (FAB) 449.0696 (MH$^+$, calcd 449.0712), 471 (MNa$^+$).

Example 15

Preparation of 4S-[3-(4-nitro-phenyl)-acryloylamino]-5-(2-oxo-pyrrolidin-3S-yl)-pent-2-enoic acid ethyl ester

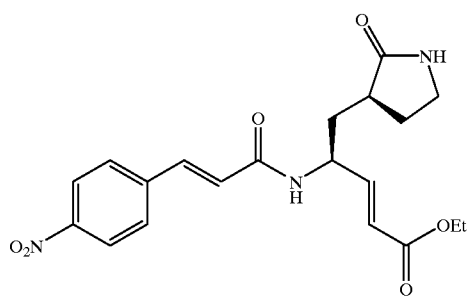

15

Compound 15 was prepared according to the method of Example 1, using 4-nitrocinnamic acid. $^1$H NMR (CDCl$_3$) δ8.29 (1H, d, J=6.1), 8.22 (2H, d, J=8.7), 7.67 (1H, d, J=14.9), 7.64 (2H, d, J=9.0), 6.88 (1H, dd, J=15.7, 5.3), 6.60 (1H, d, J=15.8), 5.98 (1H, dd, J=14.2, 1.4), 5.82 (1H, s), 4.70–4.60 (1H, m), 4.17 (2H, q, J=7.1), 3.43–3.37 (2H, m), 2.60–2.42 (2H, m), 2.05–1.75 (3H, m), 1.27 (3H, t, J=7.1). MS (FAB) 402.1649 (MH$^+$. calcd 402.1665), 424 (MNa$^+$).

Example 16

Preparation of 4S-[3-(methoxy-phenyl)-acryloylamino]-5-(2-oxo-pyrrolidin-3S-yl)-pent-2-enoic acid ethyl ester

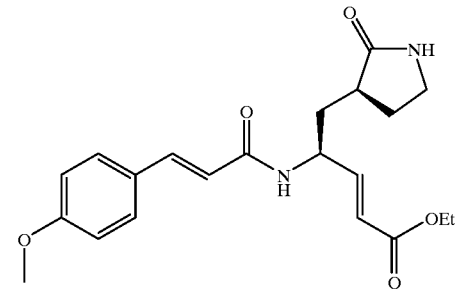

16

Compound 16 was prepared according to the method of Example 1, using 4-methoxycinnamic acid. $^1$H NMR (CDCl$_3$) δ7.58 (1H, d, J=15.6), 7.48 (1H, d, J=7.3), 7.44 (2H, d, J=8.7), 6.90 (1H, dd, J=15.7, 5.1), 6.87 (2H, d, J=8.4), 6.34 (1H, d, J=15.6), 6.07 (1H, s), 6.18 (1H, d, J=15.7), 4.80–4.65 (1H, m), 4.59 (2H, q, J=7.1), 4.11 (3H, s), 3.41–3.32 (2H, m), 2.58–2.24 (2H, m), 2.08–1.68 (3H, m), 1.25 (3H, t, J=7.1). MS (FAB) 387.1927 (MH$^+$, calcd 387.1920), 409 (MNa$^+$).

Example 17

Preparation of 4S-[3-(3-hydroxy-phenyl)-acryloylamino]-5-(2-oxo-pyrrolidin-3S-yl)-pent-2-enoic acid ethyl ester

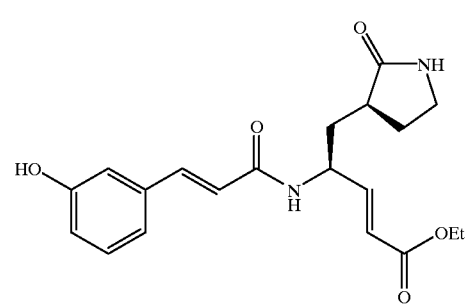

17

Compound 17 as prepared according to the method of Example 1, using 3-hydroxycinnamic acid as starting material. $^1$H NMR (CDCl$_3$) δ7.77 (1H, d, J=7.3), 7.57 (1H, d, J=15.6), 7.90 (1H, t, J=7.8), 7.10 (1H, s), 6.90–6.81 (2H, m), 6.44 (1H, d, J=5.4), 6.42 (1H, s), 5.95 (1H, dd, J=5.7, 1.1), 4.76–4.64 (1H, m), 4.13 (2H, q, J=7.2), 3.39–3.31 (2H, m), 2.58–2.37 (1H, m), 2.10–1.64 (3H, m), 1.23 (3H, t, J=7.1). MS (FAB) 373.1766 (MH$^+$, calcd. 373.1763), 395 (MNa$^+$).

Example 18

Preparation of 4S-[(6,7-dimethoxy-naphthalene-2-carbonyl)-amino]-5-(2-oxo-pyrrolidin-3S-yl)-pent-2-enoic acid ethyl ester

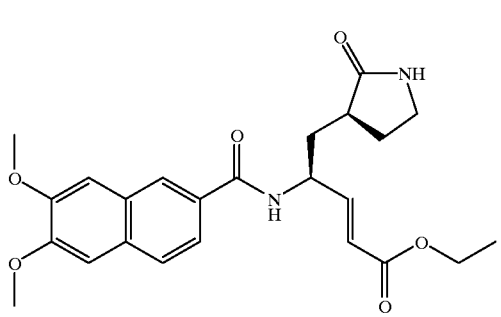

Compound 18 was prepared according to the method of Example 1, using 6,7-dimethoxy-2-naphthoic acid. $^1$H NMR (CDCl$_3$) δ8.30(1H, s), 8.16 (1H, d, J=6.5), 7.90–7.70 (2H, m), 7.21 (s, 1H), 7.13 (s, 1H), 6.95 (1H, dd, J=15.2, 5.2), 6.43 (1H, s), 6.03 (1H, dd, J=15.7, 1.4), 4.82–4.70 (1H, m), 4.17 (2H, q, J=7.1), 4.02 (3H, s), 4.00 (3H, s), 3.48–3.30 (2H, m), 2.72–2.60 (1H, m), 2.60–2.45 (1H, m), 2.20–2.05 (1H, m), 2.00–1.80 (2H, m), 1.27 (3H, t, J=7.1). MS (FAB) 441.2012 (MH$^+$, calcd. 441.2026), 463 (MNa$^+$).

Example 19

Preparation of 4S-[(5,6-dimethoxy-1-methyl-indole-2-carbonyl)-amino]-5-(2-oxo-pyrrolidin-3S-yl)-pent-2-enoic acid ethyl ester

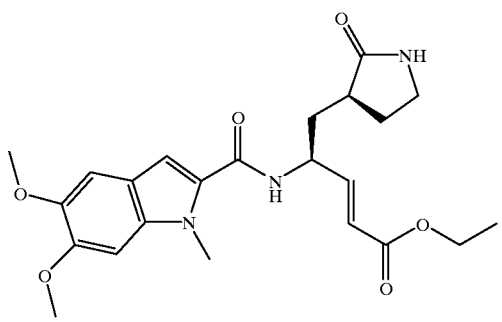

Compound 19 was prepared according to the method of Example 1, using 5,6-dimethoxy-2-indolecarboxylic acid. $^1$H NMR (CDCl$_3$) δ7.99 (1H, d, J=6.2), 7.03 (1H, s), 7.02 (1H, s), 6.95 (1H, dd, J=15.6, 5.3), 6.76 (1H, s), 6.37 (1H, s), 6.03 (1H, dd, J=15.6, 1.4), 4.80–4.70 (1H, m), 4.17 (2H, q, J=7.1), 4.03 (3H, s), 3.97 (3H, s), 3.91 (3H, s), 3.45–3.30 (2H, m), 2.70–2.60 (1H, m), 2.60–2.45 (1H, m), 2.20–1.70 (3H, m), 1.27(3H, t, J=7.1). MS (FAB) 444.2147 (MH$^+$, calcd 444.2135), 466 (MNa$^+$).

Example 20

Preparation of 4S-[(5-bromo-1H-indole-2-carbonyl)-amino]-5-(2-oxo-pyrrolidin-3S-yl)-pent-2-enoic acid

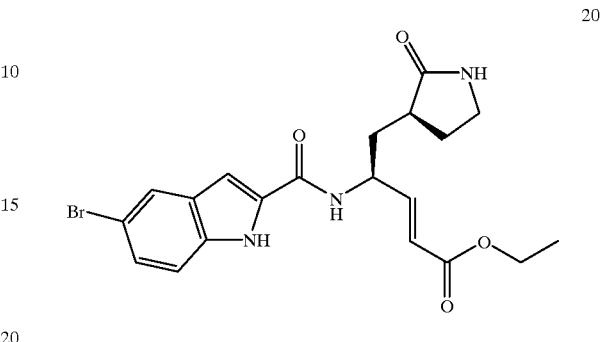

Compound 20 was prepared according to the method of Example 1, using 5-bromo-2-indolecarboxylic acid. $^1$H NMR (CDCl$_3$) δ9.94 (1H, s), 8.94 (1H, d, J=5.9), 7.73 (1H, s), 7.30 (2H, s), 7.07 (1H, d, J=1.8) 6.95 (1H, dd, J=15.6, 5.3), 6.42 (1H, s), 6.03 (1H, dd, J=15.6, 1.4), 4.80–4.65 (1H, m), 4.17 (2H, q, J=7.1), 3.45–3.35 (2H, m), 2.70–2.55 (1H, m), 2.50–2.38 (1H, m), 2.15–1.78 (3H, m), 1.27 (3H, t, J=7.1). MS (FAB) 448.0858 (MH$^+$, calcd 448.0872), 470 (MNa$^+$).

Example 21

Preparation of 4S-[(5-bromo-1-methyl-indole-2-carbonyl)-amino]-5-(2-oxo-pyrrolidin-3S-yl)-pent-2-enoic acid ethyl ester

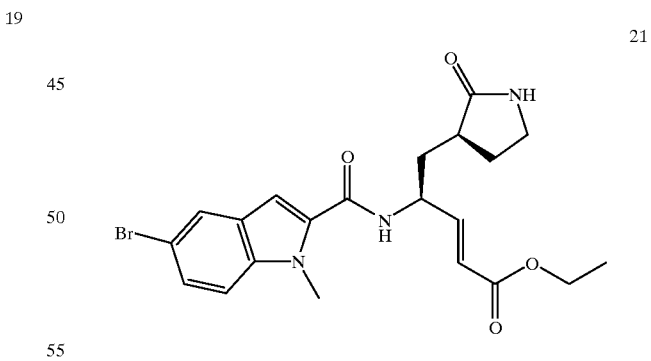

Compound 21 was prepared according to the method of Example 1, using 5-bromo-1-methyl-2-indolecarboxylic acid. $^1$H NMR (CDCl$_3$) δ8.69 (1H, d, J=5.8), 7.76 (1H, d, J=1.8), 7.37 (1H, dd, J=8.8, 1.9), 7.23 (1H, d, J=8.8), 7.07 (1H, s), 6.95 (1H, dd, J=15.6, 5.4), 6.03 (1H, dd, J=15.6, 1.4), 5.99 (1H, s), 4.72–4.60 (1H, m), 4.17 (2H, q, J=7.1), 4.04 (3H, s), 3.42–3.30 (2H, m), 2.65–2.40 (2H, m), 2.20–1.70 (3H, m), 1.27 (3H, t, J=7.1). MS (FAB) 462.1014 (MH$^+$, calcd 462.1028), 484 (MNa$^+$).

Example 22

Preparation of 4S-[(3-acetylamino-naphthalene-2-carbonyl)-amino]-5-(2-oxo-pyrrolidin-3S-yl)-pent-2-enoic acid ethyl ester

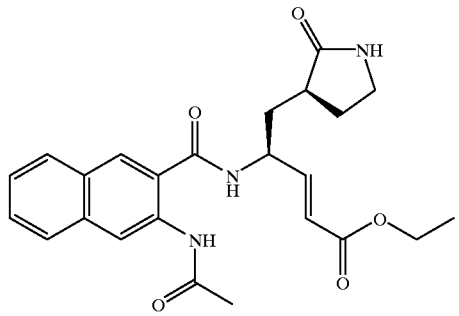

22

Compound 22 was prepared according to the method of Example 1, using 3-acetylamino-2-naphthoic acid. $^1$H NMR (CDCl$_3$) δ11.20 (1H, s), 9.30 (1H, d, J=5.4), 8.99 (1H, s), 8.31 (1H, s), 7.80 (2H, t, J=7.3), 6.04 (1H, d, J=15.6), 4.70–4.65 (1H, m), 4.18 (2H, q, J=7.1), 3.19–3.15 (2H, m), 2.57–2.52 (1H, m), 2.41–2.34 (1H, m), 2.22 (3H, s), 2.13–2.01 (1H, m), 1.88–1.79 (2H, m), 1.27 (3H, t, J=7.1). MS (FAB) 438.2018 (MH$^+$, calcd 438.2029), 460 (MNa$^+$).

Example 23

Preparation of 4S[3-(3-bromo-4-methyl-phenyl)-acryloylamino]-5-(2-oxo-pyrrolidin-3S-yl)-pent-2-enoic acid ethyl ester

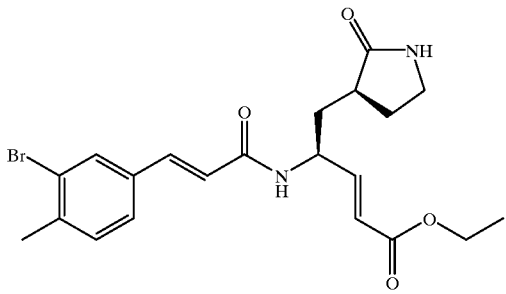

23

Compound 23 was prepared according to the method of Example 1, using 3-bromo-4-methylcinnamic acid. $^1$H NMR (CDCl$_3$) δ7.81 (1H, d, J=7.0), 7.65 (1H, s), 7.52 (1H, d, J=15.6), 7.35–7.20 (2H, m), 6.89 (1H, dd, J=15.6, 5.3), 6.46 (1H, d, J=15.7), 6.15 (1H, s), 5.95 (1H, d, J=15.6), 4.78–4.65 (1H, m), 4.17 (2H, q, J=7.1), 3.40–3.30 (2H, m), 2.60–2.35 (5H, m), 2.10–1.70 (3H, m), 1.27 (3H, t, J=7.1). MS (FAB) 449.1090 (MH$^+$, calcd 449.1076), 471 (MNa$^+$).

Example 24

Preparation of 4S-[3-(1S-ethoxycarbonyl-3-methyl-butyl)-ureido]-5-(2-oxo-pyrrolidin-3S-yl)-pent-2-enoic acid ethyl ester

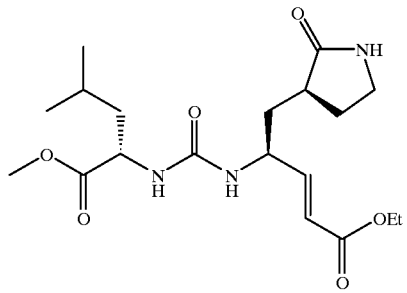

24

4S-Amino-5-(2-oxo-pyrrolidin-3S-yl)-pent-2-enoic acid ethyl ester (as disclosed in U.S. patent application Ser. No. 09/301,977 which is hereby incorporated by reference in its entirety) (17 mg, 0.074 mmol) in DMF (1 mL) was treated with ethyl-2-isocyanato-4-methyl valerate (0.05 mL, 0.15 mmol) and held at room temperature for 1 h. The solution was washed with brine (10 mL), extracted with EtOAc (20 mL), and dried (MgSO$_4$). Evaporation followed by preparative reverse phase chromatography (CH$_3$CN—H$_2$O) yielded 15 mg (50%) of product 24. $^1$H NMR (CDCl$_3$) δ6.86 (1H, dd, J=16.0, 4.9), 5.97 (1H, d, J=14.9), 4.55–4.40(2H,m), 4.28–4.10 (4H, m), 3.45–3.30 (2H, m), 2.60–2.38 (2H, m), 2.00–1.45 (6H, m), 1.32–1.23 (6H, m) 0.94 (6H, d, J=0.9). HRMS (FAB) 408.2041 (MH$^+$) calcd. 408.2029.

Example 25

Preparation of 6-carbamoyl-4S-[(naphthalene-2-carbonyl)-amino]-hex-2-enoic acid ethyl ester

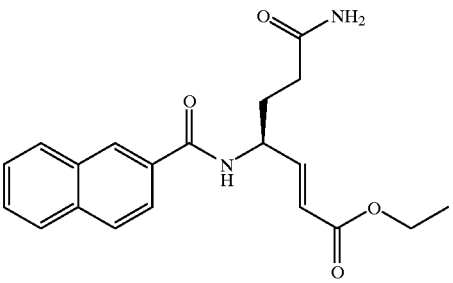

25

(a) Preparation of Functionalized Resin

FMOC-Rink polystyrene resin (2.40 g, 1.58 mmol) (Dragovich et al. *J. Med. Chem.* (1998) 41:2819) was treated with a 1:1 solution of DMF-piperidine (25 mL) to remove the FMOC. The slurry was agitated 15 minutes, then washed with DMF (3×10 mL), MeOH (3×10 mL), then CH$_2$Cl$_2$ (3×10 mL). The resin was then treated with a solution of FMOC-4-amino-hept-2-enedioic acid-1-ethyl ester (1.5 eq, 2.37 mmol, 1.00 g), DIEA (2 eq, 4.74 mmol, 0.82 mL), and HATU (1 eq, 2.37 mmol, 0.90 g) in DMF (25 mL). The resulting mixture was agitated 1 h, then washed with DMF (3×10 mL), MeOH (3×10 mL), then CH$_2$Cl$_2$ (3×10 mL). The FMOC was removed by treatment with a 2% DBU-DMF solution (25 mL), and agitated 1 h. The resin was washed with CH$_2$Cl$_2$ (3×10 mL). This resin was used for all subsequent compound preparations.

(b) Conversion to Compound 25

The functionalized resin prepared above (100 mg, 0.059 mmol) was suspended in a solution of DMF (5 mL) and DIEA (6 eq, 0.35 mmol, 0.07 mL), then treated with 2-naphthoic acid (3 eq, 0.18 mmol, 34 mg) and HATU (3 eq, 0.18 mmol, 68 mg), then agitated for 2 h. The resin was washed with CH$_2$Cl$_2$ (3×10 mL), then suspended in a 95:5 TFA-CH$_2$Cl$_2$ solution (10 mL) for 1 h, with vigorous stirring. The resin was removed by filtration, and the filtrate was evaporated. The resulting oil was purified by silica gel chromatography to yield 13 mg (63%) of product 25. $^1$H NMR (CDCl$_3$) δ8.41 (1H, s), 7.98–7.88 (4H, m), 7.62–7.53 (3H, m), 6.97 (1H, dd, J=15.8, 5.0), 6.03 (1H, d, J=15.8), 4.94–4.90 (1H, m), 4.19 (2H, q, J=7.0), 2.57–2.38 (2H, m), 2.17–2.11 (2H, m), 1.27 (3H, t, J=7.0). MS (FAB) 355 (MH$^+$), 377 (MNa$^+$).

Example 26

Preparation of 4S-[(benzo[b]thiophene-2-carbonyl)-amino]-6-carbamoyl-hex-2-enoic acid ethyl ester

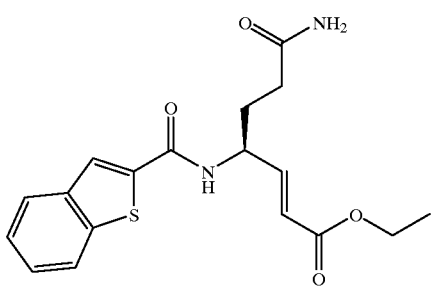

26

The functionalized resin prepared in Example 25(a) was converted to the product 26 by treatment with benzo[b]thiophene-2-carboxylic acid, as described in Example 25(b). $^1$H NMR (CDCl$_3$) δ7.86 (1H, s), 7.84–7.76 (3H, m), 7.41–7.37 (2H, m), 6.92 (1H, dd, J=15.8,2), 6.00 (1H, d, J=15.8), 4.90–4.70 (1H, m), 4.17 (2H, q, J=7.2), 2.55–2.30 (2H, m), 2.15–2.00 (2H, m), 1.26 (3H, t, J=7.2). MS (FAB 361 (MH$^+$), 383 (MNa$^+$).

Example 27

Preparation of 6-carbamoyl-4S-(4-dimethylamino-benzylamino)-hex-2-enoic acid ethyl ester

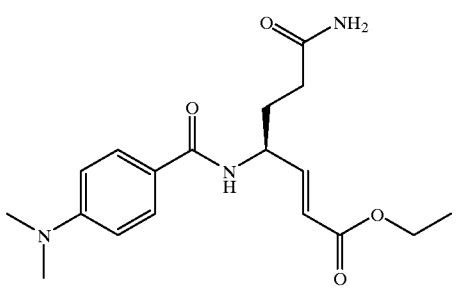

27

The functionalized resin prepared in Example 25(a) was converted to the product 27 by treatment with 4-dimethylaminobenzoic acid, as described in Example 25(b). $^1$H NMR (CDCl$_3$) δ7.74 (2H, d, J=8.8), 6.93 (1H, dd, J=15.6, 5.0), 5.97 (1H, d, J=15.4), 4.90–4.80 (1H, m), 4.17 (2H, q, J=7.0), 3.02, (6H, s), 2.50–2.30 (2H, m), 2.20–2.00 (2H, m), 1.26 (3H, t, J=7.0). MS (FAB) 386 (MH$^+$), 408 (MNa$^+$).

Example 28

Preparation of 6-carbamoyl-4S-[(quinoxaline-2-carboxyl)-amino]-hex-2-enoic acid ethyl ester

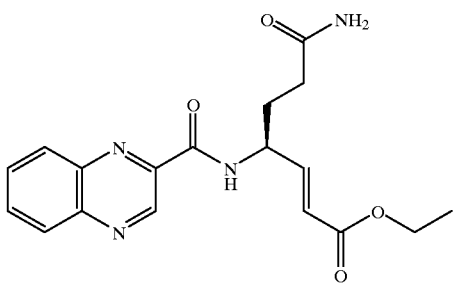

28

Compound 28 was prepared by the method of Example 25, using quinoxaline-2-carboxylic acid. $^1$H NMR (CDCl$_3$) δ9.62 (1H, s), 8.38–8.13 (3H, m), 7.95–7.82 (2H, m), 6.95 (1H, dd, J=15.6, 5.7), 6.03 (1H, d, J=15.6), 5.95 (1H, s), 5.58 (1H, s), 5.05–4.90 (1H, m), 4.17 (2H, q, J=7.0), 2.50–2.30 (2H, m), 2.20–2.00 (2H, m), 1.25 (3H, t, J=7.1). MS (FAB) 357 (MH$^+$), 379 (MNa$^+$).

Example 29

Preparation of 6-carbamoyl-4S-(3-phenyl-acryloylamino)-hex-2-enoic acid ethyl ester

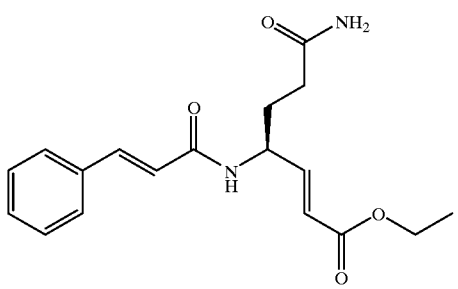

29

Compound 29 was prepared by the method of Example 25, using cinnamic acid. $^1$H NMR (CD$_3$OD) δ7.72–7.58 (3H, m), 7.50–7.38 (3H, m), 6.92 (1H, dd, J=15.6, 5.7), 6.70 (1H, d, J=15.6), 6.02 (1H, d, J=15.6), 4.80–4.65 (1H, m), 4.17 (2H, q, J=7.1), 2.40–2.30 (2H, m), 2.20–1.80 (2H, m), 1.25 (3H, t, J=7.1). MS (FAB) 331 (MH$^+$), 353 (MNa$^+$).

Example 30

Preparation of 4S-[3-(3-bromophenyl)-acryloylamino]-6-carbamoyl-hex-2-enoic acid ethyl ester

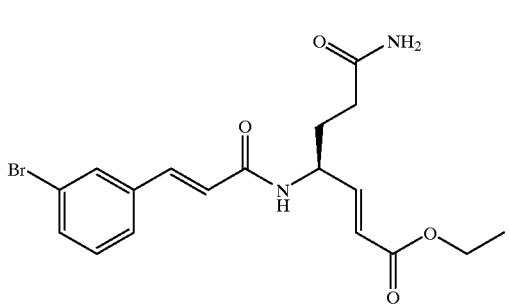

Compound 30 was prepared by the method of Example 25, using 3-bromocinnamic acid. $^1$H NMR (CDCl$_3$) δ7.80–7.20 (5H, m), 6.82 (1H, dd, J=15.6, 5.3), 6.46 (1H, d, J=15.8), 5.91 (1H, d, J=15.8), 4.75–4.60 (1H, m), 4.14 (2H, q, J=7.4), 2.40–2.20 (2H, m), 2.00–1.80 (2H, m), 1.23 (3H, t, J=7.2). MS (FAB) 409 (MH$^+$), 433 (MNa$^+$).

Example 31

Preparation of 6-carbamoyl-4S-[(quinoline-2-carbonyl)-amino]-hex-2-enoic acid ethyl ester

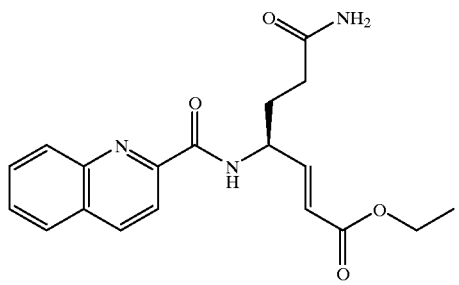

Compound 31 was prepared by the method of Example 25, using quinoline-2-carboxylic acid. $^1$H NMR (CD$_3$OD) δ8.40–8.10 (3H,m), 7.90–7.60 (3H,m), 6.95 (1H, dd, J=15.6, 5.3), 6.03 (1H, d, J=15.6), 5.00–4.85 (1H, m), 4.18 (2H, q, J=7.1), 2.40–2.20 (2H, m), 2.00–1.80 (2H,m), 1.23 (3H, t, J=7.1). MS (FAB) 356 (MH$^+$), 378 (MNa$^+$).

Example 32

Preparation of 6-carbamoyl-4S-[(5-methyl-2-phenyl-2H-[1,2,3]triazole-4-carbonyl)-amino]-hex-2-enoic acid ethyl ester

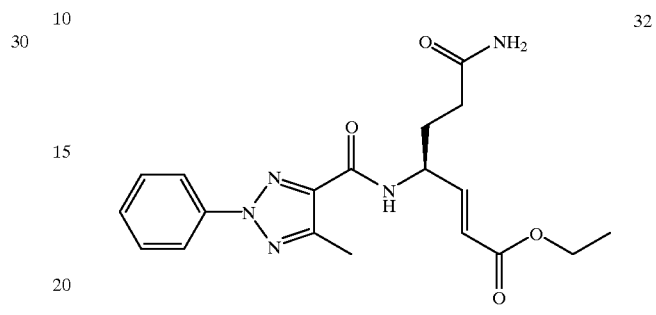

Compound 32 was prepared by the method of Example 25, using 5-methyl-2-phenyl-2H-[1,2,3]triazole-4-carboxylic acid. $^1$H NMR(CD$_3$OD) δ7.38–7.20 (5H, m), 6.90 (1H, dd, J=15.6, 5.3), 5.85 (1H, d, J=15.6), 4.75–4.60 (1H, m), 4.18 (2H, q, J 7.1), 2.40–2.20 (2H, m), 2.00–1.80 (2H, m), 1.40–1.20 (6H, m). MS (FAB) 386 (MH$^+$), 408 (MNa$^+$).

Example 33

Preparation of 4S-[(2-benzyl-5-tert-butyl-2H-pyrazole-3-carbonyl)-amino]-6-carbamoyl-hex-2-enoic acid ethyl ester

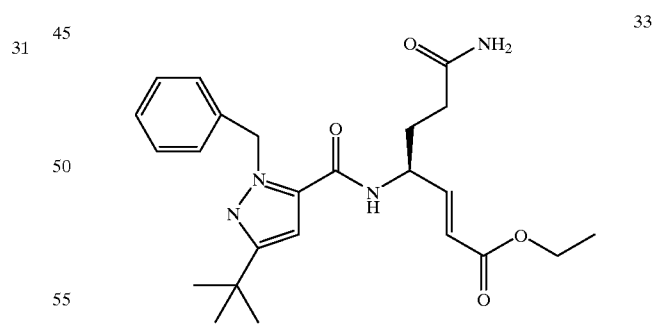

Compound 33 was prepared by the method of Example 25, using 2-benzyl-5-tert-butyl-2H-pyrazole-3-carboxylic acid. $^1$H NMR (CDCl$_3$) δ8.23 (1H,s), 8.10 (1H, d, J=7.0), 7.90–7.40 (7H, m), 6.90 (1H, dd, J=15.6, 5.3), 5.95 (1H, d, J=15.6), 4.85–4.70 (1H, m), 4.18 (2H, q, J=7.1), 2.83 (6H, s), 2.40–2.20 (2H, m), 2.10–1.90 (2H, m), 1.25 (3H, t, J=7.1). MS (FAB) 441 (MH$^+$), 463 (MNa$^+$).

Example 34

Preparation of 4S-benzylamino-6-carbamoyl-hex-2-enoic acid ethyl ester

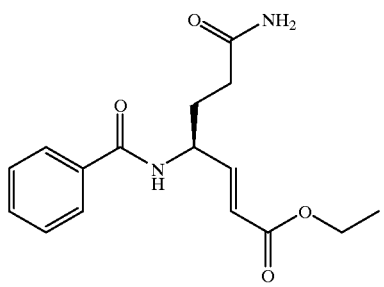

Compound 34 was prepared by the method of Example 25, using benzoic acid. $^1$H NMR (CDCl$_3$) δ8.00–7.90 (2H, m), 7.80–7.40 (4H, m), 6.95 (1H, dd, J=15.6, 5.5), 5.98 (1H, d, J=15.6), 5.95 (1H, s), 5.52 (1H, s), 4.18 (2H, q, J=7.2), 2.60–2.35 (2H, m), 2.20–2.10 (2H, m), 1.25 (3H, t, J=7.1). MS (FAB) 305 (MH$^+$), 327 (MNa$^+$).

Example 35

Preparation of 6-carbamoyl-4S-(3,4-dichloro-benzoylamino)-hex-2-enoic acid ethyl ester

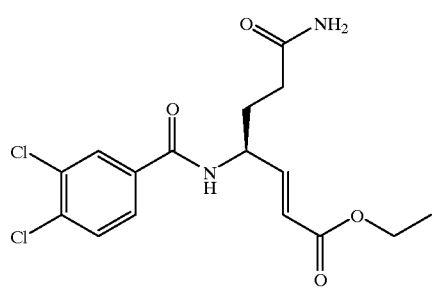

Compound 35 was prepared by the method of Example 25, using 3,4-dichlorobenzoic acid. $^1$H NMR (CDCl$_3$) δ8.18 (1H, d, J=5.2), 8.03 (1H, s), 7.75 (1H, d, J=7.5), 7.52 (1H, d, J=8.0), 6.90 (1H, dd, J=15.6, 5.5), 5.98 (1H, d, J=15.5), 5.80 (1H, s), 5.63 (1H, s), 4.85–4.70 (1H, m), 4.15 (2H, q, J=7.0), 2.60–2.35 (2H, m), 2.20–2.10 (2H, m), 1.25 (3H, t, J=7.1). MS (FAB) 373 (MH$^+$), 395 (MNa$^+$).

Example 36

Preparation of benzoic acid-2-[1S-2-carbamoyl-ethyl)-3-ethoxycarbonyl-allylcarbamoyl]-benzyl ester

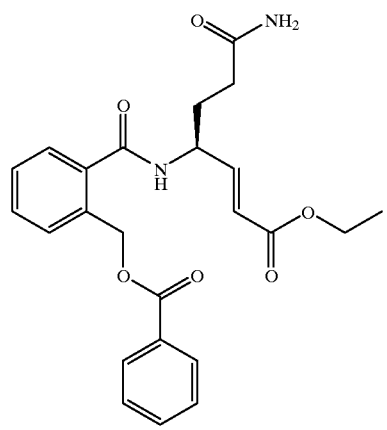

Compound 36 was prepared by the method of Example 25, using 2-benzoyloxymethylbenzoic acid. $^1$H NMR (CDCl$_3$) δ8.18 (2H, m), 7.65–7.30 (7H, m), 7.15 (1H, d, J=6.4), 6.95 (1H, dd, J=15.6, 5.5), 6.18 (1H, s), 6.03 (1H, d, J=15.6), 5.72 (1H, d, J=12.0), 5.57 (1H, s), 5.56 (1H, d, J=12.0), 4.95–4.78 (1H, m), 4.21 (2H, q, J=7.1), 2.50–2.25 (2H, m), 2.20–1.90 (2H, m), 1.28 (3H, t, J=7.1). MS (FAB) 439 (MH$^+$), 461 (MNa$^+$).

Example 37

Preparation of 6-carbamoyl-4S-(2-phenethyl-benzoylamino)-hex-2-enoic acid ethyl ester

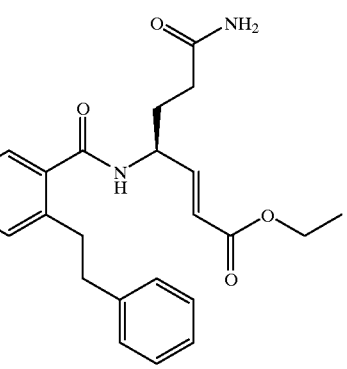

Compound 37 was prepared by the method of Example 25, using 2-phenethylbenzoic acid. $^1$H NMR (CDCl$_3$) δ7.42–7.10 (9H, m), 6.85 (1H, dd, J=15.5, 5.4), 6.42 (1H, d, J=6.0), 5.95 (1H, d, J=15.6), 5.90 (1H, s), 5.60 (1H, s), 4.85–4.75 (1H, m), 4.18 (2H, q, J=7.1), 3.18–2.90 (4H, m), 2.40–2.28 (2H, m), 2.10–1.90 (2H, m), 1.26 (3H, t, J=7.1). MS (FAB) 409 (MH$^+$), 431 (MNa$^+$).

Example 38

Preparation of 6-carbamyl-4S-[(1H-indole-2-carbonyl)-amino]-hex-2-enoic acid ethyl ester

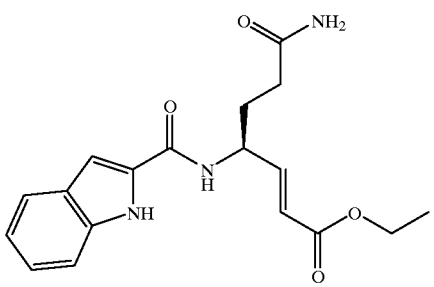

Compound 38 was prepared by the method of Example 25, using indole-2-carboxylic acid. $^1$H NMR (CDCl$_3$) δ9.24 (1H, s), 7.85–7.10 (6H, m), 6.95 (1H, dd, J=15.6, 5.5), 6.03 (1H, d, J=15.6), 5.68 (1H, s), 5.48 (1H, s), 4.82–4.79 (1H, m), 4.21 (2H, q, J=7.1), 2.40–2.35 (2H, m), 2.20–2.00 (2H, m), 1.25 (3H, t, J=7.1), MS (ES) 344 (MH$^+$), 356 (MNa$^+$).

Example 39

Preparation of 4S-[(5-Fluoro-1H-indole-2-carbonyl)-amino]-5-(2-oxo-pyrrolidin-3S-yl)-pent-2-enoic acid ethyl ester

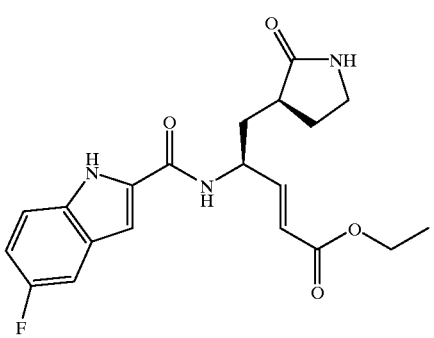

Compound 39 was prepared according to the method of Example 1, using as starting material 5-fluoro-2-indole carboxylic acid. $^1$H NMR (CDCl$_3$) δ9.83 (1H, s), 8.69 (1H, d, J=6.2), 7.40–7.34 (1H, m), 7.29–7.25 (1H, m), 7.11 (1H, s), 7.07–7.00 (1H, m), 6.94 (1H, dd, J=16.2, 5.4), 6.77 (1H, s), 6.03 (1H, d, J=15.6), 4.79–4.73 (1H, m), 4.18 (2H, q, J=7.1), 3.46–3.40 (2H, m), 2.70–2.66 (1H, m), 2.51–2.46 (1H, m), 2.19–1.82 (3H, m), 1.27 (3H, t, J=7.1). MS (FAB) 388.1666 (MH$^+$, calcd 388.1673), 410 (MNa$^+$).

Example 40

Preparation of 4S-[(5-Chloro-1H-indole-2-carbonyl)-amino]-5-(2-oxo-pyrrolidin-3S-yl)-pent-2-enoic acid ethyl ester

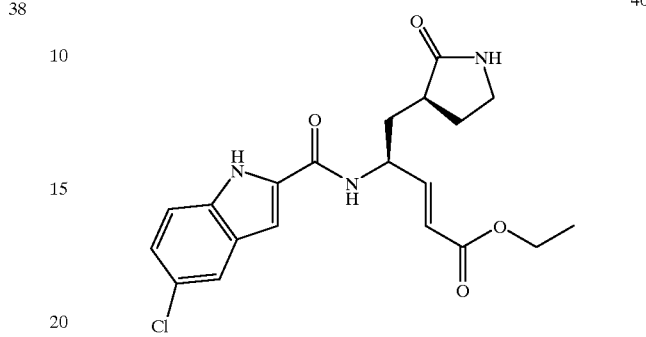

Compound 40 was prepared according to the method of Example 1, using as starting material 5-chloro-2-indole carboxylic acid. $^1$H NMR (CDCl$_3$) δ10.22 (1H, s), 8.99 (1H, d, J=5.9), 7.54 (1H, s), 7.34 (1H, d, J=8.7), 7.17 (1H, d, J=9.1), 7.09 (1H, s), 6.96 (1H, dd, J=15.9, ), 6.58 (1H, s), 6.04 (1H, d, J=15.6), 4.76–4.70 (1H, m), 4.17 (2H, q, J=7.2), 3.39–3.34 (2H, m), 2.63–2.60 (1H, m), 2.46–2.41 (1H, m), 2.10–2.04 (1H, m), 1.94–1.85 (2H, m), 1.25 (3H, t, J=7.2). MS (FAB) 404.1392 (MH$^+$, calcd. 404.1377), 426 (MNa$^+$).

Example 41

Preparation of 4S-[(5-Methoxy-1H-indole-2-carbonyl)-amino]-5-(2-oxo-pyrrolidin-3S-yl)-pent-2-enoic acid ethyl ester

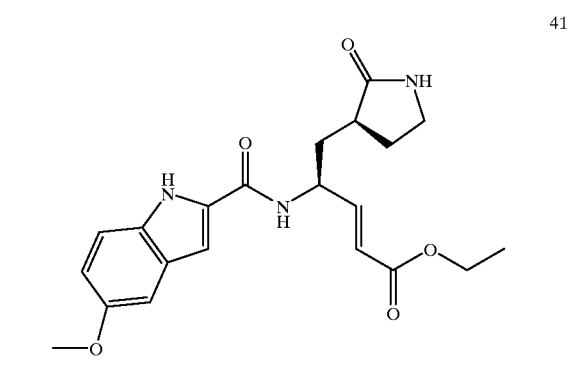

Compound 41 was prepared according to the method of Example 1, using as starting material 5-methoxy-2-indole carboxylic acid. $^1$H NMR (CDCl$_3$) δ9.15 (1H, s), 8.79 (1H, d, J=5.8), 7.31 (1H, d, J=8.9), 7.07 (1H, s), 7.06 (1H, s), 6.99–6.92 (2H, m), 6.04 (1H, d, J=15.6), 5.86 (1H, s), 4.73–4.67 (1H, m), 4.17 (2H, q, J=7.2), 3.84 (3H, s), 3.42–3.37 (2H, m), 2.63–2.57 (1H, m), 2.52–2.45 (1H, m), 2.12–1.82 (3H, m), 1.26 (3H, t, J=7.1). MS (FAB) 400.1882 (MH$^+$, calcd. 400.1872), 422 (MNa$^+$).

Example 42

Preparation of 4S-[(7-Nitro-1H-indole-2-carbonyl)-amino]-5-(2-oxo-pyrrolidin-3S-yl)-pent-2-enoic acid ethyl ester

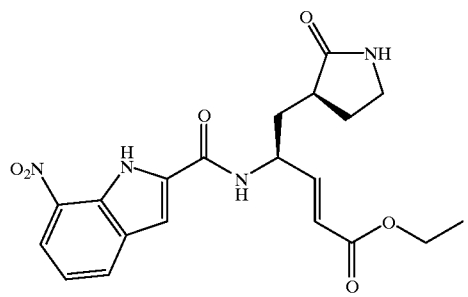

42

Compound 42 was prepared according to the method of Example 1, using as starting material 7-nitro-2-indole carboxylic acid. $^1$H NMR (CDCl$_3$) δ10.55 (1H, s), 9.09 (1H, d, J=5.6), 8.26 (1H, d, J=9.1), 8.02 (1H, d, J=7.8), 7.24 (1H, t, J=7.9), 6.94 (1H, dd, J=15.6, 5.7), 6.22 (1H, s), 6.05 (1H, d, J=15.6), 4.76–4.70 (1H, m), 4.19 (2H, q, J=7.1), 3.50–3.39 (2H, m), 2.70–2.64 (1H, m), 2.55–2.48 (1H, m), 2.14–1.86 (3H, m), 1.27 (3H, t, J=7.1). MS (FAB) 415.1636 (MH$^+$, calcd. 415.1618), 437 (MNa$^+$).

Example 43

Preparation of 4-[(5-Methyl-1H-indole-2-carbonyl)-amino]-5-(2-oxo-pyrrolidin-3-yl)-pent-2-enoic acid ethyl ester

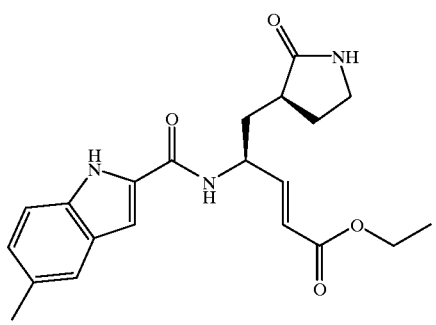

43

Compound 43 was prepared according to the method of Example 1, using as starting material 5-methyl-2-indole carboxylic acid. $^1$H NMR (CDCl$_3$) δ9.36 (1H, s), 8.52 (1H, d, J=6.3), 7.42 (1H, s), 7.32 (1H, d, J=8.3), 7.11 (1H, d, J=8.4), 7.05 (1H, s), 6.95 (1H, dd, J=15.6, 5.4), 6.07 (1H, s), 6.04 (1H, d, J=16.4), 4.77–4.75 (1H, m), 4.18 (2H, q, J=7.2), 3.50–3.39 (2H, m), 2.67–2.64 (1H, m), 2.46–2.43 (1H, m), 2.43 (3H, s), 2.11–2.07 (1H, m), 1.98–1.83 (2H, m), 1.27 (3H, t, J=7.1). MS (FAB) 384.1216 (MH$^+$, calcd. 384.1923), 406 (MNa$^+$).

Example 44

Preparation of 4S-[(6-Chloro-2H-chromene-3-carbonyl)-amino]-5-(2-oxo-pyrrolidin-3S-yl)-pent-2-enoic acid ethyl ester

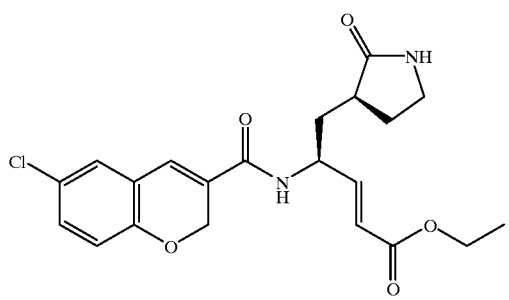

44

Compound 44 was prepared according to the method of Example 1, using as starting material 6-chloro-2H-chromene-3-carboxylic acid. $^1$H NMR (CDCl$_3$) δ8.61 (1H, d, J=5.1), 7.18–7.09 (3H, m), 6.86 (1H, dd, J=15.6, 5.6), 6.76 (1H, d, J=8.2), 5.96 (1H, d, J=15.6), 5.88 (1H, s), 5.03 (2H, s), 4.60–4.50 (1H, m), 4.18 (2H, q, J=7.2), 3.43–3.36 (2H, m), 2.59–2.40 (2H, m), 2.04–1.76 (3H, m), 1.27 (3H, t). MS (FAB) 419.1361 (MH$^+$, calcd 419.1374), 441 (MNa$^+$).

Example 45

Preparation of 4S-[(2-Methyl-5-phenyl-furan-3-carbonyl)-amino]-5-(2-oxo-pyrrolidin-3S-yl)-pent-2-enoic acid ethyl ester

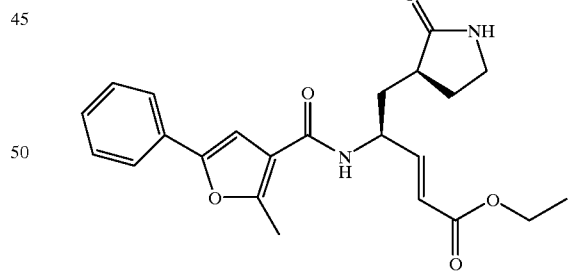

45

Compound 45 was prepared according to the method of Example 1, using as starting material 2-methyl-5-phenyl-furan-3-carboxylic acid. $^1$H NMR (CDCl$_3$) δ8.16 (1H, d, J=5.8), 7.69–7.62 (2H, m), 7.42–7.34 (2H, m), 7.29–7.22 (1H, m), 6.93 (1H, s), 6.92 (1H, dd, J=15.6, 5.3), 6.01 (1H, d, J=5.6), 5.68 (1H, s), 4.74–4.63 (1H, m), 4.18 (2H, q, J=7.1), 3.42–3.34 (2H, m), 2.68 (3H, s), 2.62–2.42 (2H, m), 2.10–1.77 (3H, m), 1.27 (3H, t). MS (FAB) 411.1929 (MH$^+$, calcd 411.1920), 433 (MNa$^+$).

Example 46

Preparation of 4S-[(6-Benzyloxy-5-methoxy-1H-indole-2-carbonyl)-amino]-5-(2-oxo-pyrrolidin-3S-yl)-pent-2-enoic acid ethyl ester

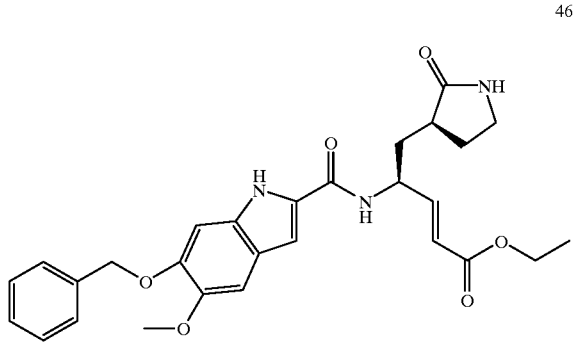

Compound 46 was prepared according to the method of Example 1, using as starting material 6-benzyloxy-5-methoxy-2-indole carboxylic acid. $^1$H NMR (CDCl$_3$) δ9.19 (1H, s), 8.66 (1H, d, J=5.8), 7.45–6.87 (9H, m), 6.02 (1H, d, J=15.8), 5.90 (1H, s), 5.14 (2H, s), 4.71–4.67 (1H, m), 4.16 (2H, q, J=7.1), 3.89 (3H, s), 3.49–3.36 (2H, m), 2.58–2.53 (1H, m), 2.47–2.42 (1H, m), 2.11–1.80 (3H, m), 1.25 (3H, t, J=7.1). MS (FAB) 506.2308 (MH$^+$, calcd. 506.2291), 528 (MNa$^+$).

Example 47

Preparation of 4S-[(1H-Indole-2-carbonyl)-amino]-5-(2-oxo-pyrrolidin-3S-yl)-pent-2-enoic acid ethyl ester

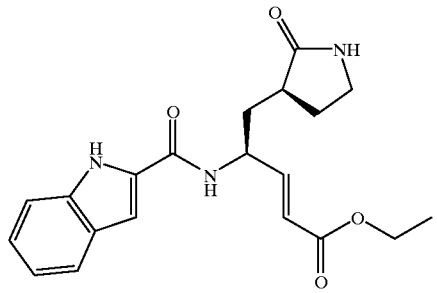

Compound 47 was prepared according to the method of Example 1, using as starting material 2-indole carboxylic acid. $^1$H NMR (CDCl$_3$) δ9.38 (1H, s), 8.83 (1H, d, J=5.7), 7.65 (1H, d, J=5.8), 7.42 (1H, d, J=5.8), 7.26 (1H, t, J=5.1), 7.15 (1H, s), 7.12 (1H, t, J=5.1), 6.96 (1H, dd, J=16.0, 5.4), 6.08 (1H, s), 6.04 (1H, d, J=17.0), 4.75–4.69 (1H, m), 4.17 (2H, q, J=7.1), 3.41–3.36 (2H, m), 2.63–2.51 (1H, m), 2.51–2.43 (1H, m), 2.18–1.82 (3H, m), 1.26 (3H, t, J=7.1). MS (FAB) 370.1760 (MH$^+$, calcd. 370.1767), 392 (MNa$^+$).

Example 48

Preparation of 4S-[3-(3-Bromo-4-fluoro-phenyl)-acryloylamino]-5-(2-oxo-pyrrolidin-3S-yl)-pent-2-enoic acid ethyl ester

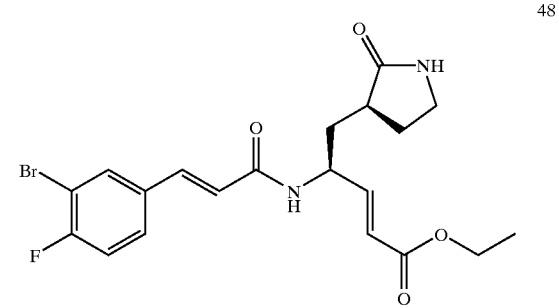

Compound 48 was prepared according to the method of Example 1, using as starting material 3-bromo-4-fluorocinnamic acid. $^1$H NMR (CDCl$_3$) δ8.02 (1H, d, J=6.6), 7.71 (1H, d, J=8.6), 7.52 (1H, d, J=15.6), 7.42–7.39 (1H, m), 7.11 (1H, t, J=8.3), 6.88 (1H, dd, J=15.6, 5.4), 6.41 (1H, d, J=15.6), 5.97 (1H, d, J=15.7), 5.94 (1H, s), 4.75–4.61 (1H, m), 4.17 (2H, q, J=7.1), 3.41–3.37 (2H, m), 2.59–2.45 (2H, m), 2.17–1.82 (3H, m), 1.27 (3H, t, J=7.2). MS (FAB) 453.0812 (MH$^+$, calcd. 453.0825), 475 (MNa$^+$).

Example 49

Preparation of 4S-[3-(6-Bromo-benzo[1,3]dioxol-5-yl)-acryloylamino]-5-(2-oxo-pyrrolidin-3S-yl)-pent-2-enoic acid ethyl ester

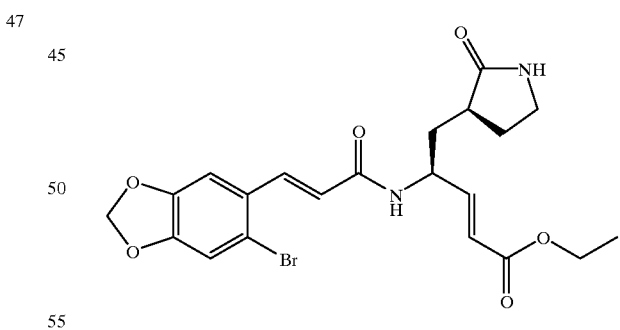

Compound 49 was prepared according to the method of Example 1, using as starting material 2-bromo-3,4-methylenedioxycinnamic acid. $^1$H NMR (CDCl$_3$) δ7.91 (1H, d, J=15.5), 7.78 (1H, d, J=6.8), 7.05 (1H, s), 7.03 (1H, s), 6.89 (1H, dd, J=1.56, 5.4), 6.29 (1H, d, J=15.5,), 6.03 (2H, s), 6.01, (1H, s), 5.98 (1H, d, J=14.5), 4.72–4.67 (1H, m), 4.16 (2H, q, J=7.1), 3.49–3.36 (2H, m), 2.56–2.43 (2H, m), 2.17–1.82 (3H, m), 1.28 (3H, t, J=7.1). MS (FAB) 479.0807 (MH$^+$, calcd 479.0818), 501 (MNa$^+$).

Example 50

Preparation of 5-(2-Oxo-pyrrolidin-3S-yl)-4S-[3-(2,4,6-trimethylphenylcarbamoyl)-acryloylamino]-pent-2-enoic acid ethyl ester

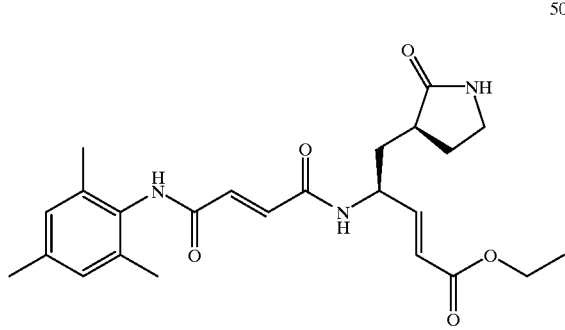

50

Compound 50 was prepared according to the method of Example 1, using as starting material 2,4,6-trimethylphenyl maleamic acid. ¹H NMR (CDCl₃) δ6.97–6.80 (3H, m), 6.38–6.24 (2H, m), 6.06–5.93 (2H, m), 4.58–4.63 (1H, m), 4.19 (2H, q, J=7.1), 3.52–3.36 (2H, m), 2.26 (3H, s), 2.18 (6H, s), 2.12–1.78 (5H, m), 1.29 (3H, t, J=7.1). MS (FAB) 442.2329 (MH⁺, calcd. 442.2342).

Example 51

Preparation of 4S-[(6-Methyl-naphthalene-2-carbonyl)-amino]-5-(2-oxo-pyrrolidin-3S-yl)-pent-2-enoic acid ethyl ester

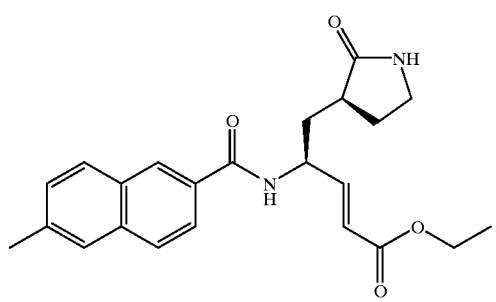

51

Compound 51 was prepared according to the method of Example 1, using as starting material 6-methyl-2-naphthoic acid. ¹H NMR (CDCl₃) δ8.42 (1H, s), 7.95 (1H, dd, J=8.6, 1.7), 7.84 (1H, d, J=8.4), 7.79 (1H, d, J=8.6), 7.63 (1H, s), 7.36 (1H, dd, J=8.6, 1.4), 6.97 (1H, dd, J=15.6, 5.3), 6.01 (1H, d, J=15.6), 5.99 (1H, s), 4.90–4.78 (1H, m), 4.17 (2H, q, J=7.1), 3.43–3.30 (2H, m), 2.70–2.60 (2H, m), 2.52 (3H, s), 2.20–2.05 (1H, m), 2.00–1.80 (2H, m), 1.26 (3H, t, J=1.7). MS (FAB) 395.1964 (MH⁺, calcd. 395.1971), 417 (MNa⁺).

Example 52

Preparation of 4S-[(6-Bromo-2H-chromene-3-carbonyl)-amino]-5-(2-oxo-pyrrolidin-3S-yl)-pent-2-enoic acid ethyl ester

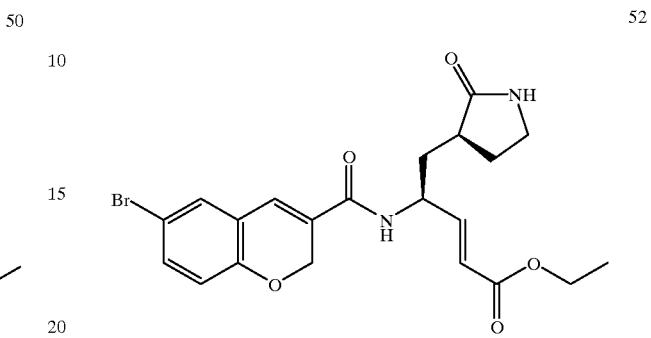

52

Compound 52 was prepared according to the method of Example 1, using as starting material 6-bromo-2H-chromene-3-carboxylic acid. ¹H NMR (CDCl₃) δ8.72 (1H, d, J=5.2), 7.28–7.23 (2H, m), 7.16 (1H, s), 6.86 (1H, dd, J=15.6, 5.6), 6.72 (1H, d, J=9.1), 5.96 (1H, dd, J=5.6, 1.4), 5.02 (d, J=1.2), 4.60–4.49 (1H, m), 4.17 (2H, q, J=7.1), 3.43–3.36 (2H, m), 2.59–2.40 (2H, m), 2.04–1.76 (3H, m), 1.27 (3H, t, J=7.1). MS (FAB) 463.0883(MH⁺, calcd 463.0869), 485 (MNa⁺).

Example 53

Preparation of 4S-[(7-Bromo-naphthalene-2-carbonyl)-amino]-5-(2-oxo-pyrrolidin-3S-yl)-pent-2-enoic acid ethyl ester

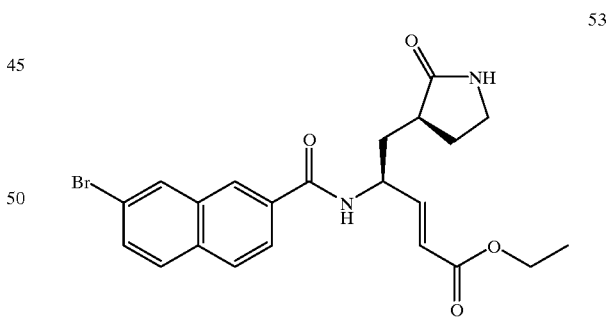

53

Compound 53 was prepared according to the method of Example 1, using as starting material 7-bromo-2-naphthoic acid. ¹H NMR (CDCl₃) δ8.82 (1H, d, J=5.7), 8.39 (1H, s), 8.09 (1H, d, J=1.6), 8.02 (1H, dd, J=8.6, 1.6), 7.85 (1H, d, J=8.6), 7.73 (1H, d, J=8.7), 7.61 (1H, dd, J=8.7, 1.9), 6.96 (1H, dd, J=15.6, 5.4), 6.06 (1H, s), 6.03 (1H, d, J=15.6), 4.85–4.70 (1H, m), 4.17 (2H, q, J=7.1), 3.45–3.30 (2H, m), 2.70–2.40 (2H, m), 2.20–1.80 (3H, m), 1.27 (3H, t, J=7.1). MS (FAB) 459.0906 (MH⁺, calcd. 459.0919), 481 (MNa⁺).

Example 54

Preparation of 4S-[(7-Hydroxy-naphthalene-2-carbonyl)-amino]-5-(2-oxo-pyrrolidin-3S-yl)-pent-2-enoic acid ethyl ester

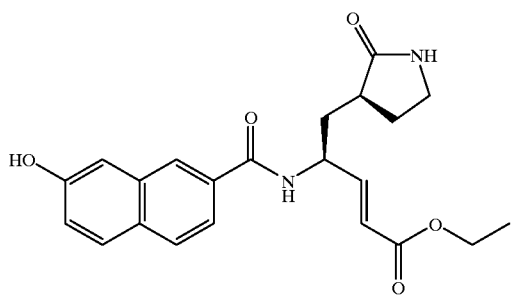

54

Compound 54 was prepared according to the method of Example 1, using as starting material 7-hydroxy-2-naphthoic acid. $^1$H NMR (CDCl$_3$) δ8.35 (1H, d, J=6.9), 8.19 (1H, s), 7.74 (1H, d, J=9.7), 7.70 (1H, d, J=8.6), 7.64 (1H, d, J=8.8), 7.22 (1H, s), 7.15 (1H, d, J=8.8), 6.96 (1H, dd, J=15.6, 5.3), 6.58 (1H, s), 6.03 (1H, d, J=15.6), 4.90–4.73 (1H, m), 4.17 (2H, q, J=7.1), 3.40–3.20 (2H, m), 2.65–2.30 (2H, m), 2.20–2.10 (1H, m), 1.90–1.70 (2H, m), 1.22 (3H, t, J=7.1). MS (FAB) 397.1777 (MH$^+$, calcd. 397.1763), 419 (MNa$^+$).

Example 55

Preparation of 5-(2-oxo-pyrrolidin-3S-yl)-4S-[3-(2-phenoxy-phenyl)-ureido]-pent-2-enoic acid ethyl ester

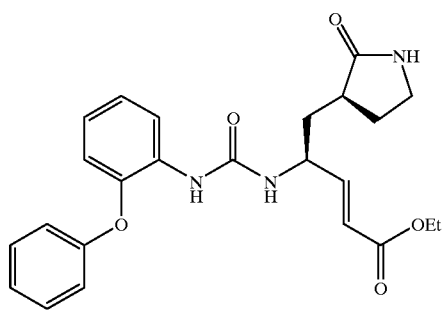

55

Compound 55 was prepared according to the method of Example 24, using 2-phenoxyphenyl isocyanate. $^1$H NMR (CDCl$_3$) δ8.22 (1H, d, J=6.8), 7.67 (1H, s), 7.48–7.38 (2H, m), 7.16–7.03 (2H, m), 7.03–6.94 (2H, m), 6.94–6.78 (4H, m), 5.97 (1H, dd, J=15.7, 1.4), 5.46 (1H, s), 4.61–4.48 (1H, m), 4.17 (2H, q, J=7.1), 3.28–3.12 (2H, m), 2.60–2.20 (2H, m), 1.92–1.70 (2H, m), 1.65–1.50 (1H, m), 1.27 (3H, t, J=7.1). MS (FAB) 412.2434 (MH$^+$, calcd 412.2448), 434 (MNa$^+$).

Example 56

Preparation of 4S-(3-naphthalen-1-yl)-5-(2-oxo-pyrrolidin-3S-yl)-pent-2-enoic acid ethyl ester

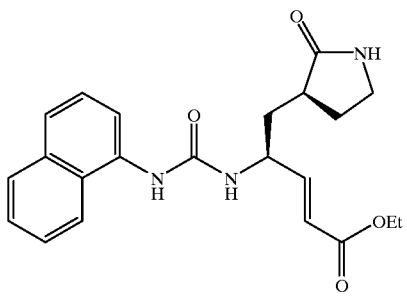

56

Compound 56 was prepared according to the method of Example 24, using 1-naphthyl isocyanate. $^1$H NMR (CDCl$_3$) δ8.05–7.97 (2H, m), 7.84–7.82 (2H, m), 7.63 (1H, d, J=8.2), 7.59–7.40 (4H, m), 6.88 (1H, dd, J=15.7, 5.1), 5.98 (1H, dd, J=15.7, 1.5), 5.82 (1H, S), 4.70–4.60 (1H, m), 4.17 (2H, q, J=7.1), 3.35–3.28 (2H, m), 2.60–2.40 (2H, m), 2.00–1.75 (2H, m), 1.68–1.56 (1H, m), 1.27 (3H, t, J=7.1). MS (FAB) 396.1912 (MH$^+$, calcd. 396.1923), 418 (MNa$^+$).

Example 57

Preparation of 4S-[3-(3,5-dimethoxy-phenyl)ureido]-5-(2-oxo-pyrrolidin-3S-yl)-pent-2-enoic acid ethyl ester

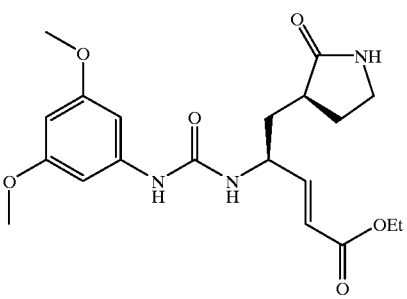

57

Compound 57 was prepared according to the method of Example 24, using 3,5-dimethoxyphenyl isocyanate. $^1$H NMR (CDCl$_3$) 6.89 (1H, dd, J=15.6, 5.0), 6.64 (2H, s), 6.14 (1H, s), 6.0 (1H, dd, J=15.6, 1.5), 5.86 (1H, s), 4.62–4.51 (1H, m), 4.17 (2H, q, J=7.1), 3.8 (6H, s), 3.43–3.34 (2H, m), 2.63–2.43 (2H, m), 2.00–1.80 (2H, m), 1.75–1.63 (1H, m), 1.28 (3H, t, J=7.1). MS (FAB) 406.1964 (MH$^+$, calcd. 406.1978), 428 (MNa$^+$).

Example 58

Preparation of 4S-[3-(3,5-dimethyl-phenyl)-ureido]-5-(2-oxo-pyrrolidin-3S-yl)-pent-2-enoic acid ethyl ester

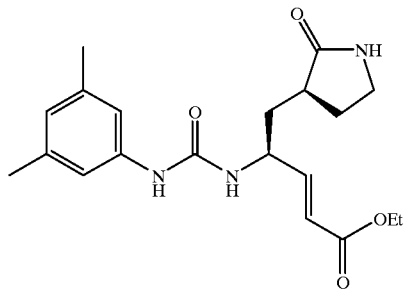

Compound 58 was prepared according to the method of Example 24, using 3,5-dimethylphenyl isocyanate. $^1$H NMR (CDCl$_3$) δ6.99 (2H, s), 6.88 (1H, dd, J=15.6, 5.1), 6.65 (1H, s), 5.98 (1H, dd, J=15.7, 1.4), 5.89 (1H, s), 4.61–4.52 (1H, m), 4.17 (2H, q, J=7.1), 3.40–3.32 (2H, m), 2.63–2.42 (2H, m), 2.25 (6H, s), 1.99–1.80 (2H, m), 1.71–1.60 (1H, m), 1.27 (3H, t, J=7.1). MS (FAB) 374.2072 (MH$^+$, calcd.374.2080), 396 (MNa$^+$).

Example 59

Preparation of 6-carbamoyl-4S-[3-(1-ethoxycarbonyl-3-methylbutyl)-ureido]-hex-2-enoic acid ethyl ester

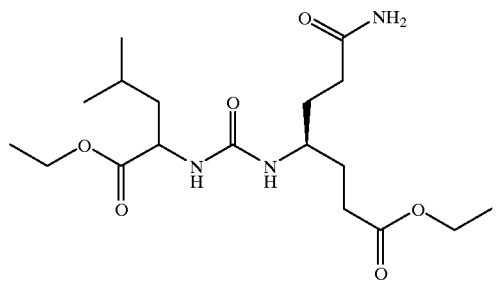

The functionalized resin prepared in Example 25(a) (100 mg, 0.059 mmol) in DMF (5 mL) was treated with ethyl-2-isocyanato-4-methyl valerate (3 eq, 0.18 mmol, 33 mg), and agitated for 2 h. The resin was washed with CH$_2$Cl$_2$ (3×10 mL), then suspended in a 95:5 TFA-CH$_2$Cl$_2$ solution (10 mL) for 1 h, with vigorous stirring. The resin was removed by filtration, and the filtrate was evaporated. The resulting oil was purified by silica gel chromatography to yield 16.1 mg (73%) of product 59. $^1$H NMR (CDCl$_3$) δ6.87 (1H, dd, J=15.8, 4.8), 5.94 (1H, d, J=16.5), 4.54–4.38 (1H, m), 4.25–4.14 (1H, m), 4.22–4.10 (4H, m), 2.40–1.40 (7H, m), 1.28 (6H, t, J=7.4), 0.95 (6H, d, J=6.3), MS (FAB) 386 (MH$^+$), 408 (MNa$^+$).

Example 60

Preparation of 4S-[2-(3-methoxy-phenoxy)-acetylamino]-5-(2-oxo-pyrrolidin-3S-yl)-pent-2-enoic acid ethyl ester

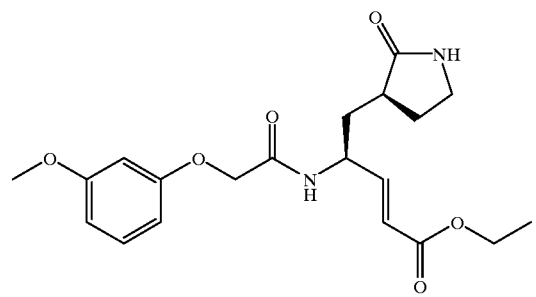

Compound 60 was prepared according to the method of Example 1, using 3-methoxyphenoxyacetic acid. $^1$H NMR (CDCl$_3$) δ7.30 (1H, d, J=8.4), 7.22 (1H, t, J=8.5), 6.87 (1H, dd, J=15.7, 5.7), 6.60–6.52 (3H, m), 5.90 (1H, d, J=15.7), 5.70 (1H, s), 4.79–4.73 (1H, m), 4.53 (2H, ABq, J=15.0), 4.19 (2H, q, J=7.1), 3.79 (3H, s), 3.35–3.30 (2H, m), 2.44–2.33 (2H, m), 2.16–2.06 (1H, m), 1.86–1.65 (2H, m), 1.28 (3H, t, J=7.1), MS (FAB) 391.1865 (MH$^+$, calcd 391.1869), 413 (MNa$^+$).

Example 61

Preparation of 4S-[2-(3-chloro-phenoxy)-acetylamino]-5-(2-oxo-pyrrolidin-3S-yl)-pent-2-enoic acid ethyl ester

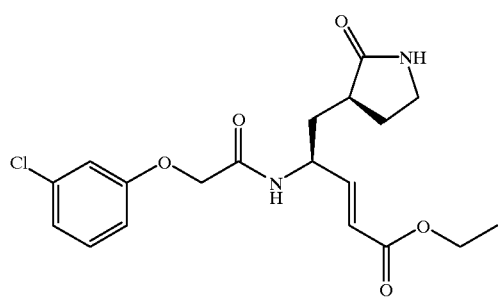

Compound 61 was prepared according to the method of Example 1, using 3-chlorophenoxyacetic acid. $^1$H NMR (CDCl$_3$) δ7.63 (1H, d, J=7.7), 7.25 (1H, t, J=8.1), 7.03–6.82 (4H, m), 5.94 (1H, d, J=15.6), 5.77 (1H, s), 4.75–4.72 (1H, m), 4.52 (2H, ABq, J=14.8), 4.19 (2H, q, J=7.1), 3.35–3.30 (2H, m), 2.44–2.32 (2H, m), 2.12–2.02 (1H, m), 1.87–1.65 (2H, m), 1.28 (3H, t, J=7.1). MS (ES) 371 (MH$^+$).

Example 62

Preparation of 4S-[2-(3,4-dichloro-phenoxy)-acetylamino]-5-(2-oxo-pyrrolidin-3S-yl)-pent-2-enoic acid ethyl ester

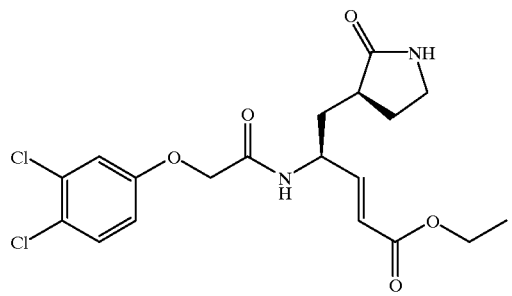

Compound 62 was prepared according to the method of Example 1, using 3,4-dichlorophenoxyacetic acid. $^1$H NMR (CDCl$_3$) δ7.84 (1H, d, J=7.2), 7.37 (1H, d, J=8.8), 7.10 (1H, s), 6.86 (1H, d, J=9.2), 6.84 (1H, dd, J=15.6, 5.9), 5.90 (1H, d, J=17.1), 5.64 (1H, s), 4.72–4.65 (1H, m), 4.51 (2H, ABq, J=14.7), 4.19 (2H, q, J=7.1), 3.36–3.31 (2H, m), 2.44–2.32 (2H, m), 2.10–1.69 (3H, m), 1.30 (3H, t, J=7.1). MS (FAB) 429.0971 (MH$^+$, calcd 429.0984).

Example 63

Preparation of 4S-[2-(3-chloro-phenyl)-acetylamino]-5-(2-oxo-pyrrolidin-3S-yl)-pent-2-enoic acid ethyl ester

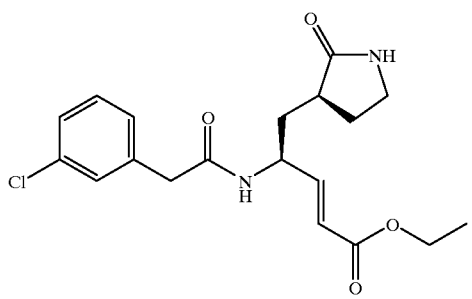

Compound 63 was prepared according to the method of Example 1, using 3-chlorophenylacetic acid. $^1$H NMR (CDCl$_3$) δ7.44 (1H, d, J=7.01), 7.30–7.15 (4H, m), 6.80 (1H, d, J=15.7, 5.4), 6.00 (1H, s), 5.84 (1H, dd, J=15.6, 1.5), 4.61–4.50 (1H, m), 4.17 (2H, q, J=7.1), 3.52 (2H, s), 3.38–3.28 (2H, m), 2.42–2.28 (2H, m), 2.00–1.70 (2H, m), 1.70–1.60 (1H, m), 1.27 (3H, t, J=7.1). MS (FAB) 379.1419 (MH$^+$, calcd. 379.1425), 401 (MNa$^+$).

Example 64

Preparation of 4S-[3-(2,5-dibromo-phenyl)-acryloylamino]-5-(2-oxo-pyrrolidin-3S-yl)-pent-2-enoic acid ethyl ester

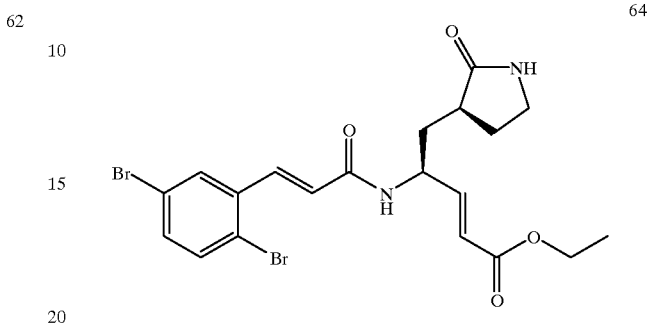

Compound 64 was prepared according to the method of Example 1, using 2,5-dibromocinnamic acid. $^1$H NMR (CDCl$_3$) δ8.15 (1H, d, J=6.4), 7.92 (1H, d, J=15.6), 7.71 (1H, s), 7.47 (1H, d, J=8.6), 7.32 (1H, d, J=8.6), 6.93 (1H, dd, J=15.6, 5.4), 6.43 (1H, d, J=15.6), 6.03 (1H, d; J=15.6), 5.62 (1H, s), 4.68–4.63 (1H, m), 4.22 (2H, d, J=7.1), 3.42–3.37 (2H, m), 2.54–2.44 (1H, m), 2.05–1.58 (4H, m), 1.30 (3H, t, J=7.1), MS (FAB) 515.0021 (MH$^+$, calcd. 515.0005).

Example 65

Preparation of 4S-[(6-hydroxy-naphthalene-2-carbonyl)-amino]-5-(2-oxo-pyrrolidin-3S-yl)-pent-2-enoic acid ethyl ester

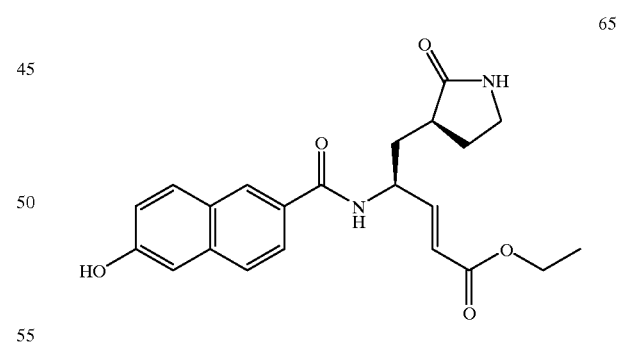

Compound 65 was prepared according to the method of Example 1, using 6-hydroxy-2-naphthoic acid. $^1$H NMR (CD$_3$OD) δ8.34 (1H, s), 7.86 (2H, d, J,=8.9), 7.73 (1H, d, J=8.7), 7.16 (1H, s), 7.15 (1H, t, J=6.4), 7.05 (1H, dd, J=15.7, 5,5), 6.04 (1H, d, J=15.7), 4.22 (2H, d, J=7.2), 3.36–3.29 (2H, m), 2.58–2.54 (1H, m), 2.54–2.42 (1H, m), 2.24–2.14 (1H, m), 1.95–1.88 (1H, m), 1.80–1.75 (1H, m), 1.27 (3H, t, J=7.0), MS (FAB) 397.1775 (MH$^+$, calcd. 397.1763).

Example 66

Preparation of 4S-[(6-bromo-7-methyl-2H-chromene-3-carbonyl)amino]-5-(2-oxo-pyrrolidin-3S-yl)-pent-2-enoic acid ethyl ester

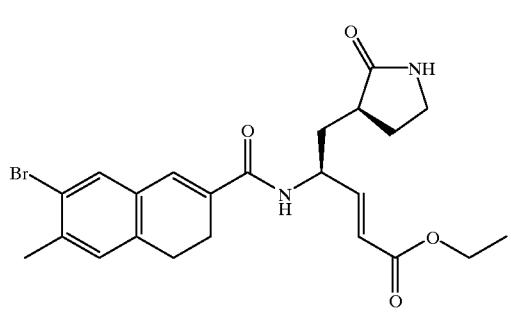

66

Compound 66 was prepared according to the method of Example 1, using 6-bromo-7-methyl-2H-chromen-3-carboxylic acid. $^1$H NMR (CDCl$_3$) δ8.35 (1H, d, J=7.1), 7.20 (1H, s), 7.10 (1H, s), 6.79 (1H, dd, J=15.7, 5.5), 6.66 (1H, s), 5.86 (1H, dd, J=15.7, 1.5), 4.89 (2H, d, J=1.3), 4.65–4.51 (1H, m), 4.10 (2H, q, J=7.1); 3.35–3.25 (2H, m), 2.50–2.28 (2H, m), 2.25 (3H, s), 2.02–1.87 (1H, m), 1.83–1.70 (1H, m), 1.65–1.55 (1H, m), 1.19 (3H, t, J=7.2). MS (FAB) 477.1043 (MH$^+$, calcd. 477.1025).

Example 67

Preparation of 4S-[(2H-chromene-3-carbonyl)-amino]-5-(2-oxopyrrolidin-3S-yl)-pent-2-enoic acid ethyl ester

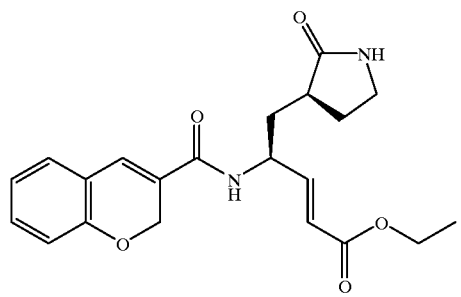

67

Compound 67 was prepared according to the method of Example 1, using 2H-chromene-3-carboxylic acid. $^1$H NMR (CDCl$_3$) δ8.46 (1H, d, J=5.4), 7.23–7.12 (3H, m), 6.94–6.81 (3H, m), 5.97 (1H, dd, J=15.6, 1.4), 5.62 (1H, s), 5.03 (1H, d, J=1.2), 4.64–4.53 (1H, m), 4.17 (2H, q, J=7.2), 3.42–3.38 (2H, m), 2.58–2.40 (2H, m), 2.03–1.74 (3H, m), 1.27 (3H, t, J=7.2) MS (FAB) 385.1774 (MH$^+$, calcd. 385.1763).

Example 68

Preparation of 4S-[(4-bromo-6-methyl-naphthalene-2-carbonyl)amino]-5-(2-oxo-pyrrolidin-3S-yl)-pent-2-enoic acid ethyl ester

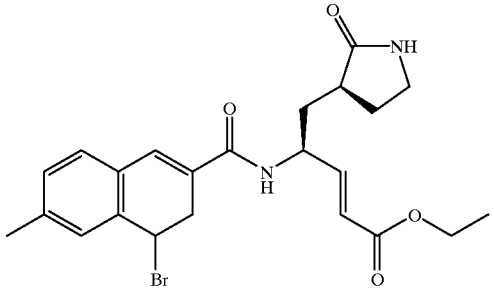

68

Compound 68 was prepared according to the method of Example 1, using 4-bromo-6-methyl-2-naphthoic acid. $^1$H NMR (CDCl$_3$) δ8.78 (1H, s), 8.69 (1H, s), 8.02 (1H, d, J=8.3), 7.80 (1H, d, J=8.4), 7.68 (1H, s), 7.59 (1H, s), 7.01 (1H, dd, J=15.5, 4.3), 6.08 (1H, d, J=15.5), 5.91 (1H, s), 4.81 (1H, s), 4.21 (2H, q, J=7.1), 3.49 (2H, d, J=8.8), 2.63–2.54 (2H, m), 2.50 (31rl, s), 2.17–1.84 (2H, m), 1.24 (3H, t, J=7.0). MS (FAB) 473.1068 (MH$^+$, calcd. 473.1076)

Example 69

Preparation of 4S-[(3-amino-naphthalene-2-carbonyl)-amino]-5-(2-oxo-pyrrolidin-3S-yl)-pent-2-enoic acid ethyl ester

69

Compound 69 was prepared according to the method of Example 1, using 3-amino-2-naphthoic acid. $^1$H NMR (CDCl$_3$) δ9.31 (brs 1H), 9.08 (brs, 1H), 8.39 (s, 1H), 8.23 (s, 1H), 7.88–7.24 (m, 4H), 7.15 (brs 1H), 7.02 (dd, 1H, J=15.7, 5.4) 1.6.12 (d, 1H, J=15.5), 5.86 (brs 1H), 4.74–4.70 (m, 1H), 4.20 (q, 2H, J=7.1), 3.31–3.28 (m, 2H), 2.62–1.64 (m, 5H), 1.30 (t, 3H, J=7.1), MS (FAB) 396.1913 (MH$^+$, calcd. 396.1923).

BIOCHEMICAL AND BIOLOGICAL EVALUATION

Results of biochemical and biological tests conducted using various compounds of the invention are described below.

Inhibition of Rhinovirus 3C Protease Activity

Stock solutions (50 mM, in DMSO) of various compounds were prepared; dilutions were in the same solvent.

Recombinant rhinovirus 3C proteases (see Birch et al., "Purification of recombinant human rhinovirus 14 3C protease expressed in *Escherichia coli*," *Protein Expr. Pur.* 1995, 6(5), 609–618) from serotypes 14, 16, and 2 were prepared by the following standard chromatographic procedures: (1) ion exchange using Q Sepharose Fast Flow from Pharmacia; (2) affinity chromatography using Affi-Gel Blue from Biorad; and (3) sizing using Sephadex G-100 from Pharmacia. Each assay sample contained 2% DMSO, 50 mM tris pH 7.6, 1 mM EDTA, a test compound at the indicated concentration, approximately 1 μM substrate, and 50–100 nM protease. The $k_{obs/I}$ values were obtained from reactions initiated by addition of enzyme rather than substrate. RVP activity was measured in the fluorescence resonance energy transfer assay. The substrate was (N-terminal) DABCYL-(Gly-Arg-Ala-Val-Phe-Gln-Gly-Pro-Val-Gly)-EDANS. In the uncleaved peptide, the EDANS fluorescence was quenched by the proximal DABCYL group. When the peptide was cleaved, the quenching was relieved, and activity was measured as an increase in fluorescence signal. Data were analyzed using standard non-linear fitting programs (Enzfit), and are shown in the Table below. In the Table, unless otherwise indicated, all data are for rhinovirus 3C protease from HRV serotype-14 (produced from the infectious cDNA clone constructed by Dr. Robert Rueckert, Institute for Molecular Virology, University of Wisconsin, Madison, Wis.). The data in the column designated $k_{obs}/[I]$ were measured from progress curves in enzyme start experiments.

Antirhinoviral H1-HeLa Cell Culture Assay

In this cell protection assay, the ability of compounds to protect cells against HRV infection was measured by the XTT dye reduction method, which is described in Weislow et al., *J. Natl. Cancer Inst.* 1989, vol. 81, 577–586.

H1-HeLa cells were infected with HRV-14 at a multiplicity of infection (m.o.i.) of 0.13 (virus particles/cell) or mock-infected with medium only. Infected or mock-infected cells were resuspended at $8 \times 10^5$ cells per mL, and incubated with appropriate concentrations of the compounds to be tested. Two days later, XTT/PMS was added to test plates and the amount of formazan produced was quantified spectrophotometrically at 450/650 nm. The $EC_{50}$ value was calculated as the concentration of compound that increased the percentage of formazan production in compound-treated, virus-infected cells to 50% of that produced by compound-free, mock-infected cells. The 50% cytotoxic dose ($CC_{50}$) was calculated as the concentration of compound that decreased the percentage of formazan produced in compound-treated, mock-infected cells to 50% of that produced by compound-free, mock-infected cells.

All strains of human rhinovirus (HRV) for use in this assay were purchased from American Type Culture Collection (ATCC), except for HRV serotype-14 (produced from the infectious cDNA clone constructed by Dr. Robert Rueckert, Institute for Molecular Virology, University of Wisconsin, Madison, Wis.). HRV stocks were propagated and viral assays were performed in H1-HeLa cells (ATCC). Cells were grown in minimal essential medium with 10% fetal bovine serum, available from Life Technologies (Gaithersburg, Md.).

The compounds were tested against control compounds WIN 51711, WIN 52084, and WIN 54954 (obtained from Sterling-Winthrop Pharmaceuticals), Pirodavir (obtained from Janssen Pharmaceuticals), and Pleconaril (prepared according to the method described in Diana et al., *J. Med. Chem* 1995, vol. 38, 1355). Antiviral data obtained for the test compounds are shown in the Table, where all data are for HRV serotype-14 unless otherwise noted in parentheses. The designation "ND" indicates that a value was not determined for that compound.

Protease Inhibition and Antiviral Activity of Formula I Compounds

| Compound No. | Protease Inhibition $k_{obs}/I$ ($M^{-1}sec^{-1}$) | Cell Protection $EC_{50}$ (μM) | Toxicity $CC_{50}$ (μM) |
|---|---|---|---|
| 1 | 1090 (HRV-14) | 0.15 | >100 |
|   | 110 (HRV-2) | 1.35 |   |
| 2 | 400 | — | — |
| 3 | 2560 | 1.4 | >10 |
| 4 | 258 | — | — |
| 5 | 173 | — | — |
| 6 | 79 | — | — |
| 7 | 36 | — | — |
| 8 | 980 | 2.67 | >10 |
| 9 | 1958 | 1.81 | >10 |
| 10 | 55 | — | — |
| 11 | 750 | — | — |
| 12 | 990 | 2.77 | >10 |
| 13 | 169 | — | — |
| 14 | 219 | — | — |
| 15 | 2021 | 1.53 | >10 |
| 16 | 664 | — | — |
| 17 | 315 | — | — |
| 18 | 262 | — | — |
| 19 | 1230 | 1.36 | >10 |
| 20 | 1369 | 4.39 | >10 |
| 21 | 1317 | 3.07 | 17.78 |
| 22 | 581, 673 | — | — |
| 23 | 4080 | 1.29 | >10 |
| 24 | 1050 | 4.6 | >10 |
| 25 | 150 | 0.6 | >100 |
|   |   | 22 (HRV-1A) |   |
|   |   | 35 (HRV-10) |   |
| 26 | 95 | 1.5 | >100 |
|   |   | 59 (HRV-1A) |   |
|   |   | 12.4 (HRV-10) |   |
| 27 | 45 | 3.9 | >100 |
| 28 | 64 | 14.1 | >100 |
| 29 | 62 | 31.6 | >100 |
| 30 | 345 | 3.2 | >100 |
| 31 | 110 | 7.1 | >100 |
| 32 | 83 | 1.8 | >100 |
| 33 | 27 | 12.6 | >100 |
| 34 | 10 | >100 | >100 |
| 35 | 35 | >100 | 100 |
| 36 | 10 | >100 | >100 |
| 37 | 6 | >100 | >100 |
| 38 | 71 | 1.0 | >100 |
| 39 | 615 | — | — |
| 40 | 1270 | — | — |
| 41 | 2190 | 2.36 | >100 |
| 42 | 272 | — | — |
| 43 | 3458 | 2.14 | >100 |
| 44 | 19700 (HRV-14) | .16 (HRV-14) | >100 |
|   | 800 (HRV-89) | 5.1 (HRV-1A) |   |
|   | 2200 (HRV-16) | 0.459 (HRV-10) |   |
|   | 385 (HRV-2) | .645 (HRV-2) |   |
| 45 | 4745 | 1.94 | >100 |
| 46 | 1830 | — | — |
| 47 | 283 | — | — |
| 48 | 2857 | 0.625 | >100 |
| 49 | 14400 | 2.512 (HRV-1A) | >100 |
|   |   | 0.316 (HRV-10) |   |
|   |   | 0.49 (HRV-14) |   |
| 50 | 225 | — | — |
| 51 | 5020 | 0.880 | >100 |
| 52 | 25000 | 5.065 (HRV-1A) | 65 |
|   | 372 (HRV-2) | 0.546 (HRV-10) |   |
|   |   | 0.175 (HRV-14) |   |
| 53 | 31400 | 4.180 (HRV-1A) | 56.2 |
|   | 385 (HRV-2) | 0.546 (HRV-10) |   |
|   |   | 0.184 (HRV-14) |   |
|   |   | 0.422 (HRV-2) |   |

-continued

Protease Inhibition and Antiviral Activity of Formula I Compounds

| Compound No. | Protease Inhibition $k_{obs}/I$ ($M^{-1}sec^{-1}$) | Cell Protection $EC_{50}$ ($\mu M$) | Toxicity $CC_{50}$ ($\mu M$) |
| --- | --- | --- | --- |
| 54 | 220 | — | — |
|    | 35 (HRV-2) |    |    |
| 55 | 200 | — | — |
| 56 | 117 | >10 | >10 |
| 57 | 388 | >10 | >10 |
| 58 | 185 | — | — |
| 59 | 400 | 19.6 | >100 |
| 60 | 77 | — | — |
| 61 | 103 | — | — |
| 62 | 134 | 6.1 | >10 |
| 63 | 7 | — | — |
| 64 | 6850 |  |  |
| 65 | 570 |  |  |
| 66 | 25000 |  |  |
| 67 | 886 | 1.191 | >100 |
| 68 | 2660 | 13.03 | >100 |
| 69 | 142 |  |  |
| WIN 51711 | — | 0.78 | >60 |
| WIN 52084 | — | 0.07 | >10 |
| WIN 54954 | — | 2.13 | >63 |
| Pirodavir | — | 0.03 | >10 |
| Pleconaril | — | 0.01 | >10 |

While the invention has been described in terms of preferred embodiments and specific examples, those skilled in the art will recognize through routine experimentation that various changes and modifications can be made without departing from the spirit and scope of the invention. Thus, the invention should be understood as not being limited by the foregoing detailed description, but as being defined by the appended claims and their equivalents.

What is claimed is:

1. A compound of formula:

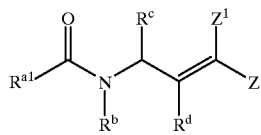

wherein:
$R^{a1}$ is a heterocycloalkyl, or heteroaryl group, provided that $R^{a1}$ is not a substituted pyrrolidinyl, where the heterocycloalkyl, or heteroaryl group is unsubstituted or substituted with one or more suitable substituents;
$R^c$ is a substituent having the formula:

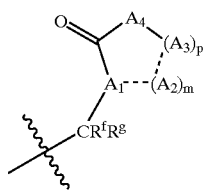

wherein:
$R^f$ and $R^g$ are each independently H or lower alkyl;
m is 1;
p is 1;
$A_1$ is CH;
$A_2$ is $C(R^h)(R^i)$, where each $R^h$, and $R^i$ is independently H or a lower alkyl group;

each $A_3$ present is $C(R^h)(R^i)$; where each $R^h$ and $R^i$ is independently H or lower alkyl;

when p is 1, $A_4$ is $N(R^k)$, where each $R^k$ is H, alkyl, aryl, or acyl;

where each dotted line in the ring depicts a single bond;

$R^d$ is H, halogen, hydroxyl or an alkyl, alkoxy or alkylthio group, where the alkyl, alkoxy or alkylthio group is unsubstituted or substituted with one or more suitable substituents;

$R^b$ is H or an alkyl group, unsubstituted or substituted with one or more suitable substituents;

Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)R"— $CO_2R"$—CN, —C(O)NR"R°, —C(O)NR"OR°, —C(S)R", —C(S)OR"—C(S)NR"R°, —C(=NR")R°, —C(=NR")OR°, —$NO_2$, —SOR°, —$SO_2R"$, —$SO_2NR"R°$, —$SO_2(NR")(OR°)$, —SONR", —$SO_3R"$, —PO(OR")$_2$, —PO(OR")(OR°), —PO(NR"R°)(OR$^p$), —PO(NR"R°)(NR$^p$R$^q$), —C(O)NR"NR°R$^p$, or —C(S)NR"NR°R$^p$, where R", R°, R$^p$ and R$^q$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the R", R°, R$^p$ and R$^q$, taken together with the atoms to which they are bonded, form a heterocycloalkyl group, which may be optionally substituted, or Z and $R^d$, together with the atoms to which they are bonded, form a cycloalkyl or heterocycloalkyl group, where Z and $R^d$ are as defined above except for moieties that cannot form the cycloalkyl or heterocycloalkyl group, or Z and $Z^1$, together with the atoms to which they are bonded, form a cycloalkyl or heterocycloalkyl group, where Z and $Z^1$ are as defined above (except for moieties that cannot form the cycloalkyl or heterocycloalkyl group);

or a prodrug, pharmaceutically acceptable salt, pharmaceutically active metabolite, or pharmaceutically acceptable solvate thereof.

2. A compound, prodrug, pharmaceutically acceptable salt, pharmaceutically active metabolite, or pharmaceutically acceptable solvate according to claim 1 having the formula:

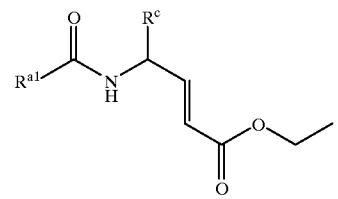

wherein $R^{a1}$ is as defined in claim 1; and $R^c$ is

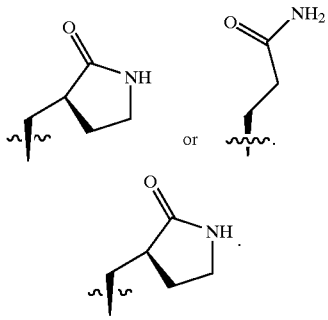

3. A compound, prodrug, pharmaceutically acceptable salt, pharmaceutically active metabolite, or pharmaceutically acceptable solvate according to claims 1 or 2, wherein $R^{a1}$ is a heterocycloalkyl, or heteroaryl group, wherein the heterocycloalkyl, or heteroaryl group is unsubstituted or substituted with one or more substituents independently selected from $(C_1-C_4)$alkyl, aryl$(C_1-C_4)$alkyl, aryl, $(C_3-C_8)$ cycloalkyl, heterocycloalkyl, heteroaryl, halo, hydroxyl, nitro, amino, $(C_1-C_4)$alkylamino, di-$(C_1-C_4)$alkylamino, aryl$(C_1-C_4)$alkoxy, aryloxy$(C_1-C_4)$alkyl; alkylenedioxy, aryloxy, $(C_3-C_8)$cycloalkoxy, heteroaryloxy, $(C_1-C_4)$ haloalkyl, $(C_1-C_4)$alkoxy, $(C_1-C_4)$haloalkoxy, hydroxamino, $(C_1-C_4)$alkoxycarbonyl, $(C_1-C_4)$ alkylcarbonylamino, $(C_1-C_4)$alkylcarbonyl, mercapto, alkylthio or arylthio, where the $(C_1-C_4)$alkyl and $(C_3-C_8)$ cycloalkyl moieties thereof are optionally substituted by one or more of $(C_1-C_4)$alkyl (except for alkyl), halo, $(C_1-C_4)$ haloalkyl, $(C_1-C_4)$alkoxy, $(C_1-C_4)$haloalkoxy and the heterocycloalkyl, aryl or heteroaryl moieties thereof are unsubstituted or are optionally substituted by one or more substituents independently selected from alkyl, haloalkyl, alkylenedioxy, nitro, amino, hydroxamino, alkylamino, dialkylamino, halo, hydroxyl, alkoxy, haloalkoxy, aryloxy, mercapto, alkylthio or arylthio groups.

4. A compound, prodrug, pharmaceutically acceptable salt, pharmaceutically active metabolite, or pharmaceutically acceptable solvate according to claims 1 or 2, wherein $R^{a1}$ is a pyrazolyl, indolyl, chromenyl, benzofuranyl, benzothienyl, benzimidazolyl, triazolyl, quinolyl, thiazolidinyl, or quinoxalinyl group, where the pyrazolyl, indolyl, chromenyl, benzofuranyl, benzothienyl, benzimidazolyl, triazolyl, quinolyl, thiazolidinyl, or quinoxalinyl group is unsubstituted or substituted with one or more substituents independently selected from $(C_1-C_4)$alkyl, aryl $(C_1-C_4)$alkyl, aryl, halo, hydroxyl, nitro, amino, $(C_1-C_4)$ alkylamino, di-$(C_1-C_4)$alkylamino, $(C_1-C_4)$alkoxy, aryl $(C_1-C_4)$alkoxy, aryloxy$(C_1-C_4)$alkyl, methylenedioxy, aryloxy, $(C_1-C_4)$haloalkyl, $(C_1-C_4)$haloalkoxy, $(C_1-C_4)$ alkoxycarbonyl, $(C_1-C_4)$alkylcarbonylamino, or $(C_1-C_4)$ alkylcarbonyl, where the $(C_1-C_4)$alkyl moieties thereof are optionally substituted by one or more of halo, $(C_1-C_4)$ alkoxy or $(C_1-C_4)$haloalkoxy and the aryl moieties thereof are unsubstituted or are optionally substituted by one or more substituents independently selected from alkyl, haloalkyl, alkylenedioxy, nitro, amino, alkylamino, dialkylamino, halo, hydroxyl, alkoxy, haloalkoxy or aryloxy groups.

5. A compound, prodrug, pharmaceutically acceptable salt, pharmaceutically active metabolite, or pharmaceutically acceptable solvate according to claims 1 or 2, wherein $R^{a1}$ is a is a pyrazolyl, indolyl, N-methylindolyl, chromenyl, benzofuranyl, benzothienyl, benzimidazolyl, , N-methylbenzimidazolyl, triazolyl, quinolyl, thiazolidinyl, or quinoxalinyl group, where the pyrazolyl, indolyl, chromenyl, benzofuranyl, benzothienyl, benzimidazolyl, triazolyl, quinolyl, thiazolidinyl, or quinoxalinyl group is unsubstituted or substituted with one or more substituents independently selected from methyl, ethyl, benzyl, phenethyl, phenyl, naphthyl, halo, hydroxyl, nitro, amino, methylamino, di-methylamino, methoxy, benzyloxy, methylenedioxy, $(C_1-C_4)$haloalkyl, $(C_1-C_4)$haloalkoxy, methoxycarbonyl, methylcarbonylamino, benzoyloxymethylene (phenylcarbonyloxymethyl-) or methylcarbonyl.

6. A compound, prodrug, pharmaceutically acceptable salt, pharmaceutically active metabolite, or pharmaceutically acceptable solvate according to claim 1, wherein:

$A_1$ is CH;

$A_2$ is $C(R^h)(R^i)$; where each $R^h$, and $R^i$ is independently H or lower alkyl;

each $A_3$ is $C(R^h)(R^i)$; where each $R^h$, and $R^i$ is independently H or lower alkyl;

when p is 1, $A_4$ is $N(R^k)$, each $R^k$ is H, alkyl, aryl, or acyl; where each dotted line in the ring depicts a single bond;

Z and $Z^1$ are independently H, F, an unsubstituted or substituted alkyl group, cycloalkyl group, heterocycloalkyl group, aryl group or heteroaryl group, —C(O) $R^n$, —$CO_2R^n$, —CN, —C(O)NR″R°, —C(O)NR″OR°, —C(S)R″, —C(S)NR″R°, —$NO_2$, —SOR°, —$SO_2R″$, —$SO_2NR″R°$, —$SO_2(NR″)(OR°)$, —SONR″, —$SO_3R″$, —$PO(OR″)_2$, —PO(OR″)(OR°), —PO (NR″R°)(OR$^p$), —PO(NR″R°)(NR$^p$R$^q$), —C(O) NR″NR°R$^p$, or —C(S)NR″NR°R$^p$, where each R″, R°, R$^p$ and R$^q$ are independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the R″, R°, R$^p$ and R$^q$, taken together with the atoms to which they are bonded, form a heterocycloalkyl group, which may be optionally substituted, form a heterocycloalkyl group, provided that Z and $Z^1$ are not both H;

or Z and R$^d$, together with the atoms to which they are bonded, form a cycloalkyl or heterocycloalkyl group, where Z and R$^d$ are as defined above except for moieties that cannot form the cycloalkyl or heterocycloalkyl group;

or Z and $Z^1$, together with the atoms to which they are bonded, form a cycloalkyl or heterocycloalkyl group, where Z and $Z^1$ are as defined above except for moieties that cannot form the cycloalkyl or heterocycloalkyl group.

7. A pharmaceutical composition comprising:

a therapeutically effective amount of at least one antipicornaviral agent selected from compounds, prodrugs, pharmaceutically acceptable salts, pharmaceutically active metabolites, and pharmaceutically acceptable solvates defined in claim 1; and a pharmaceutically acceptable carrier, diluent, vehicle, or excipient.

8. A method of treating a mammalian disease condition mediated by picornaviral protease activity, comprising administering to a mammal in need thereof a therapeutically effective amount of at least one compound, prodrug, pharmaceutically acceptable salt, pharmaceutically active metabolite, or pharmaceutically acceptable solvate defined in claim 1.

9. A method of inhibiting the activity of a picornaviral 3C protease, comprising contacting the picornaviral 3C protease with an effective amount of at least one compound, prodrug, pharmaceutically acceptable salt, pharmaceutically active metabolite, or pharmaceutically acceptable solvate defined in claim 1.

10. The method as defined in claim 9, wherein the picornaviral 3C protease is a rhinoviral protease.

11. A compound selected from the group:

4S-[(5-bromo-pyridine-3-carbonyl)-amino]-5-(2-oxo-pyrrolidin-3S-yl)-pent-2-enoic acid ethyl ester;

4S-[(3-hydroxyquinoxaline-2-carbonyl)-amino]-5-(2-oxopyrrolidin-3S-yl)-pent-2-enoic acid ethyl ester;

4S-[(5-ethyl-1H-indole-2-carbonyl)-amino]-5-(2-oxo-pyrrolidin-3S-yl)-pent-2-enoic acid ethyl ester;

4S-(3-benzo[1,3]dioxol-5-yl-acryloylamino)-5-(2-oxo-pyrrolidin-3S-yl)-pent-2-enoic acid ethyl ester;

4-[(1H-benzoimidazole-2-carbonyl)-amino]-5-(2-oxo-pyrrolidin-3S-yl)-pent-2-enoic acid ethyl ester;

4S-[(3-acetyl-2-phenyl-thiazolidine-4-carbonyl)-amino]-5-(2-oxo-pyrrolidin-3S-yl)-pent-2-enoic acid ethyl ester;

4S-[(5-bromo-benzofuran-2-carbonyl)-amino]-5-(2-oxo-pyrrolidin-3S-yl)-pent-2-enoic acid ethyl ester;

4S-[(5,6-dimethoxy-1-methyl-indole-2-carbonyl)-amino]-5-(2-oxo-pyrrolidin-3S-yl)-pent-2-enoic acid ethyl ester;

4S-[(5-bromo-1H-indole-2-carbonyl)-amino]-5-(2-oxo-pyrrolidin-3S-yl)-pent-2-enoic acid;

4S-[(5-bromo-1-methyl-indole-2-carbonyl)-amino]-5-(2-oxo-pyrrolidin-3S-yl)-pent-2-enoic acid ethyl ester;

4S-[(benzo[b]thiophene-2-carbonyl)-amino]-6-carbamoyl-hex-2-enoic acid ethyl ester;

6-carbamoyl-4S-[(quinoxaline-2-carboxyl)-amino]-hex-2-enoic acid ethyl ester;

6-carbamoyl-4S-[(quinoline-2-carbonyl)-amino]-hex-2-enoic acid ethyl ester;

6-carbamoyl-4S-[(5-methyl-2-phenyl-2H-[1,2,3]triazole-4-carbonyl)-amino]-hex-2-enoic acid ethyl ester;

4S-[(2-benzyl-5-tert-butyl-2H-pyrazole-3-carbonyl)-amino]-6-carbamoyl-hex-2-enoic acid ethyl ester;

6-carbamyl-4S-[(1H-indole-2-carbonyl)-amino]-hex-2-enoic acid ethyl ester;]

4S-[(5-fluoro-1H-indole-2-carbonyl)-amino]-5-(2-oxo-pyrrolidin-3S-yl)-pent-2-enoic acid ethyl ester;

4S-[(5-chloro-1H-indole-2-carbonyl)-amino]-5-(2-oxo-pyrrolidin-3S-yl)-pent-2-enoic acid ethyl ester;

4S-[(5-methoxy-1H-indole-2-carbonyl)-amino]-5-(2-oxo-pyrrolidin-3S-yl)-pent-2-enoic acid ethyl ester;

4S-[(7-nitro-1H-indole-2-carbonyl)-amino]-5-(2-oxo-pyrrolidin-3S-yl)-pent-2-enoic acid ethyl ester;

4-[(5-methyl-1H-indole-2-carbonyl)-amino]-5-(2-oxo-pyrrolidin-3-yl)-pent-2-enoic acid ethyl ester;

4S-[(6-chloro-2H-chromene-3-carbonyl)-amino]-5-(2-oxo-pyrrolidin-3S-yl)-pent-2-enoic acid ethyl ester;

4S-[(2-methyl-5-phenyl-furan-3-carbonyl)-amino]-5-(2-oxo-pyrrolidin-3S-yl)-pent-2-enoic acid ethyl ester;

4S-[(6-benzyloxy-5-methoxy-1H-indole-2-carbonyl)-amino]-5-(2-oxo-pyrrolidin-3S-yl)-pent-2-enoic acid ethyl ester;

4S-[(1H-indole-2-carbonyl)-amino]-5-(2-oxo-pyrrolidin-3S-yl)-pent-2-enoic acid ethyl ester;

4S-[3-(6-bromo-benzo[1,3]dioxol-5-yl)-acryloylamino]-5-(2-oxo-pyrrolidin-3S-yl)-pent-2-enoic acid ethyl ester;

4S-[(6-bromo-2H-chromene-3-carbonyl)-amino]-5-(2-oxo-pyrrolidin-3S-yl)-pent-2-enoic acid ethyl ester;

and 4S-[(2H-chromene-3-carbonyl)-amino]-5-2-oxopyrrolidin-3S-yl)-pent-2-enoic acid ethyl ester;

or a prodrug, pharmaceutically acceptable salt, pharmaceutically active metabolite, or pharmaceutically acceptable solvate thereof.

* * * * *